(12) United States Patent  (10) Patent No.: US 9,204,647 B2
Gross et al.  (45) Date of Patent: Dec. 8, 2015

(54) PYRAZOLE COMPOUNDS FOR CONTROLLING INVERTEBRATE PESTS

(71) Applicant: BASF SE, Ludwigshafen (DE)

(72) Inventors: Steffen Gross, Ludwigshafen (DE); Delphine Breuninger, Bobenheim-Roxheim (DE); Henricus Maria Martinus Bastiaans, Usingen (DE); Wolfgang von Deyn, Neustadt (DE); Michael Puhl, Lampertheim (DE); Karsten Koerber, Eppelheim (DE); Douglas D. Anspaugh, Apex, NC (US); Deborah L. Culberston, Fuquay Varina, NC (US); Hassan Oloumi-Sadeghi, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/073,369

(22) Filed: Nov. 6, 2013

(65) Prior Publication Data

US 2014/0068820 A1  Mar. 6, 2014

Related U.S. Application Data

(62) Division of application No. 12/674,991, filed as application No. PCT/EP2008/061136 on Aug. 26, 2008, now Pat. No. 8,642,597.

(60) Provisional application No. 60/968,109, filed on Aug. 27, 2007.

(51) Int. Cl.
*A01N 43/40* (2006.01)
*A61K 31/4439* (2006.01)
(Continued)

(52) U.S. Cl.
CPC ............... *A01N 43/64* (2013.01); *A01N 43/56* (2013.01); *A01N 43/707* (2013.01); *A01N 43/74* (2013.01); *A01N 47/18* (2013.01); *C07D 401/12* (2013.01); *C07D 401/14* (2013.01); *C07D 417/14* (2013.01)

(58) Field of Classification Search
CPC ..... A01N 43/53; A01N 43/64; A01N 43/707; A01N 43/74; A01N 47/18; C07D 401/12; C07D 401/14; C07D 417/14
See application file for complete search history.

(56) References Cited

U.S. PATENT DOCUMENTS 5,360,799 A  11/1994  Bachy et al.
6,747,041 B1  6/2004  Katsuhira et al.
(Continued)

FOREIGN PATENT DOCUMENTS

CA  2 026 131  3/1991
CN  1711255  12/2005
(Continued)

OTHER PUBLICATIONS

Office Action dated Oct. 11, 2013, from U.S. Appl. No. 13/382,225, filed Jan. 4, 2012.

(Continued)

Primary Examiner — Kyle Purdy
(74) Attorney, Agent, or Firm — Brinks Gilson & Lione

(57) ABSTRACT

The present invention relates to novel pyrazole compounds of the formulae I and II, to their salts and their N-oxides which can be used for combating or controlling invertebrate pests, in particular arthropod pests. The invention also relates to a method for controlling invertebrate pests by using these compounds. The present invention also relates to seed and to an agricultural and veterinary composition comprising said compounds.

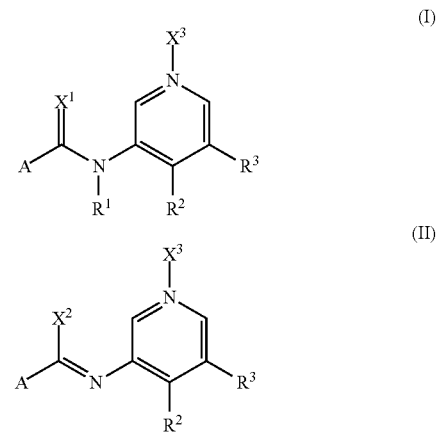

wherein
A is a pyrazole radical of the formulae A1, A2 or A3

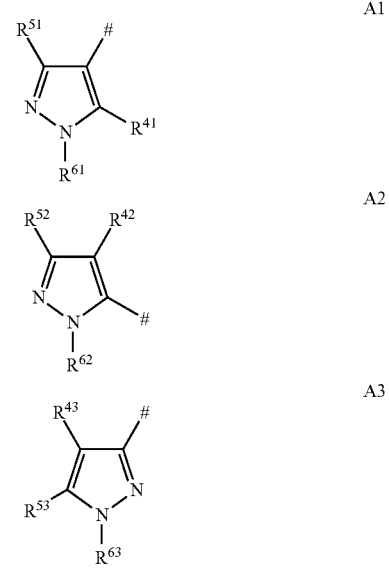

denotes the binding site to the remainder of formulae I or II;
$X^1$ is S, O or $NR^{1a}$;
$X^2$ is $OR^{2a}$, $NR^{2b}R^{2c}$, $S(O)_mR^{2d}$;
$X^3$ is a lone pair or oxygen;
$R^1$, $R^2$ and $R^3$ are, inter alia, hydrogen,
and wherein $R^{41}$, $R^{42}$, $R^{43}$, $R^{51}$, $R^{52}$, $R^{53}$, $R^{61}$, $R^{62}$, $R^{63}$, are as defined in claim 1.

32 Claims, No Drawings

(51) Int. Cl.

| | | |
|---|---|---|
| A01N 43/707 | (2006.01) | |
| C07D 401/12 | (2006.01) | |
| C07D 401/14 | (2006.01) | |
| A01P 7/00 | (2006.01) | |
| A01N 43/64 | (2006.01) | |
| A01N 43/56 | (2006.01) | |
| A01N 43/74 | (2006.01) | |
| A01N 47/18 | (2006.01) | |
| C07D 417/14 | (2006.01) | |

(56) References Cited

U.S. PATENT DOCUMENTS

| | | |
|---|---|---|
| 2006/0069132 A1 | 3/2006 | Armet et al. |
| 2007/0203148 A1 | 8/2007 | Dunkel et al. |
| 2007/0275980 A1 | 11/2007 | Yoshida et al. |
| 2008/0033513 A1 | 2/2008 | Man et al. |
| 2008/0058389 A1 | 3/2008 | Dunkel et al. |
| 2009/0163516 A1 | 6/2009 | Dunkel et al. |
| 2009/0176844 A1 | 7/2009 | Dunkel et al. |
| 2009/0247586 A1 | 10/2009 | Dunkel et al. |
| 2009/0286800 A1 | 11/2009 | Cheruvallath et al. |

FOREIGN PATENT DOCUMENTS

| | | |
|---|---|---|
| CN | 1927838 | 3/2007 |
| CN | 101 062 916 | 10/2007 |
| CN | 101062919 | 10/2007 |
| EP | 0 419 944 | 4/1991 |
| EP | 0573883 | 12/1993 |
| EP | 0606175 | 7/1994 |
| EP | 0 891 975 | 1/1999 |
| EP | 1 188 745 | 3/2002 |
| EP | 2 263 455 | 12/2010 |
| JP | 10195072 | 7/1998 |
| JP | 2001159610 | 6/2001 |
| JP | 2001348378 | 12/2001 |
| JP | 2004/269515 | 9/2004 |
| JP | 2004331541 | 11/2004 |
| JP | 2005/532367 | 10/2005 |
| JP | 2006/520373 | 9/2006 |
| JP | 2007/77106 | 3/2007 |
| JP | 2008/285482 | 11/2008 |
| WO | WO 98/54154 | 12/1998 |
| WO | WO 99/48868 | 9/1999 |
| WO | WO 00/29398 | 5/2000 |
| WO | WO 01/00575 | 1/2001 |
| WO | WO 02/070483 | 9/2002 |
| WO | WO 02/094791 | 11/2002 |
| WO | WO 03/037900 | 5/2003 |
| WO | WO 03/106427 | 12/2003 |
| WO | WO 2004/017908 | 3/2004 |
| WO | WO 2004/035545 | 4/2004 |
| WO | WO 2004/046129 | 6/2004 |
| WO | WO 2004/076458 | 9/2004 |
| WO | WO 2004/080999 | 9/2004 |
| WO | WO 2004/106324 | 12/2004 |
| WO | WO 2005/040152 | 5/2005 |
| WO | WO 2005/073165 | 8/2005 |
| WO | WO 2005/074686 | 8/2005 |
| WO | WO 2005/075411 | 8/2005 |
| WO | WO 2006/015860 | 2/2006 |
| WO | WO 2006/045522 | 5/2006 |
| WO | WO 2006/074445 | 7/2006 |
| WO | WO 2006/133926 | 12/2006 |
| WO | WO 2007/046548 | 4/2007 |
| WO | WO 2007/046550 | 4/2007 |
| WO | WO 2007/065664 | 6/2007 |
| WO | WO 2007/068373 | 6/2007 |
| WO | WO 2007/068375 | 6/2007 |
| WO | WO 2007/068377 | 6/2007 |
| WO | WO 2007/085188 | 8/2007 |
| WO | WO 2007/121687 | 11/2007 |
| WO | WO 2007/139856 | 12/2007 |
| WO | WO 2007/139860 | 12/2007 |
| WO | WO 2008/116898 | 10/2008 |
| WO | WO 2009/027393 | 3/2009 |
| WO | WO 2009/086303 | 7/2009 |
| WO | WO 2010/017047 | 2/2010 |
| WO | WO 2010/023277 | 3/2010 |
| WO | WO 2010/034737 | 4/2010 |
| WO | WO 2010/034738 | 4/2010 |
| WO | WO 2011/003793 | 1/2011 |
| WO | WO 2011/003796 | 1/2011 |
| WO | WO 2011/009804 | 1/2011 |

OTHER PUBLICATIONS

Office Action dated Feb. 25, 2014, from U.S. Appl. No. 13/382,225, filed Jan. 4, 2012.

Office Action dated Dec. 23, 2013 from U.S. Appl. No. 13/386,473, filed Jan. 23, 2012.

Shelton, M.D., "Effects of Weeds on the Diversity and Abundance of Insects in Soybeans", Environmental Entomology, Apr. 1983, p. 296-298, vol. 12, No. 2.

Bayhan, E., et al. "Effect of temperature on development, mortality, fecundity, and reproduction of Aphis rumicis L. (Homoptera:Aphididae) on broadleaf dock (*Rumex obtusifolius*) and Swiss chard (*Beta vulgaris vulgaris* var. *cida*)", J. Pest. Sci, 2006, p. 57-61, vol. 79.

Final Office Action dated Dec. 9, 2014 from U.S. Appl. No. 13/386,473.

International Search Report completed Jul. 15, 2009, in International Application No. PCT/EP2008/061136, filed Aug. 26, 2008.

Preliminary Report on Patentability from corresponding International Application No. PCT/EP2008/061136, filed Aug. 26, 2008.

Milyutin, A.V., et al. "Synthesis properties and biological activity of 3/pyridylamides of 4/aryl/2/hydroxy/4/oxo/2/butenic (Aroylpyruvic) acids", Pharmaceutical Chemistry Journal, 1997, p. 30/33, vol. 31, No. 1.

Persson, Tobias, et al., "Pyrazole carboxamides and carboxylic acids as protein kinase inhibitors in aberrant eukaryotic signal transduction: induction of growth arrest in MCF/7 cancer cells", Organic & Biomolecular Chemistry, 2007, pp. 3963/3970, vol. 5.

Sharlow et al., "Development and Implementation of a Miniaturized High/Throughput Time/Resolved Fluorescence Energy Transfer Assay to Identify Small Molecule Inhibitors of Polo/Like Kinase 1," ASSAY and Drug Development Technologies, vol. 5, No. 6, (2007), pp. 723/735.

Office Action dated May 8, 2013, from U.S. Appl. No. 13/386,473, filed Jan. 23, 2012.

U.S. Environmental Protection Agency, "Insect Repellents: Use and Effectiveness", <http://cfpub.epa.gov/oppref/insect/>, Updated Apr. 10, 2013, p. 1/2.

Merriam/Webster, "Pest", <http://www.merriam/webster.com/dictionary/pest>, © 2013, p. 1/4.

National Wildlife Federation, "Invertebrates", <http://www.nwf.org/wildlife/wildlife/library/invertebrates.aspx>, © 1996/2012, p. 1/ 2.

Pest Control Methods, "Pest control methods: Natural vs. Chemical", <http://www.pestcontrolmethods.org/>, © 2012, p. 1/4.

Britannica Online Encyclopedia, "Arthropod", <http://www.britannica.com/EBchecked/topic/36943/arthropod>, 2013, p. 1 /5.

Texas A&M Agrilife Extension, "Order Homoptera", <https://insects.tamu.edu/fieldguide/orders/homoptera.html>, 1999, p. 1.

Cranshaw et al., "Spider Mites", Colorado State University Extension, Fact Sheet No. 5.507, Insect Series: Home and Garden, Nov. 2006, p. 1/3.

Technicide, "Pest Control", <http://technicide.com/Pest/Control>, © 2006, p. 1/2.

Buzzle, "Wasp Insect Control: Wasp Traps and Repellent", <http://www.buzzle.com/articles/wasp/insect/control/wasp/traps/and/repellent.htrnb/, Dec. 8, 2007, p. 1/2.

PYRAZOLE COMPOUNDS FOR CONTROLLING INVERTEBRATE PESTS

This application is a Divisional of U.S. application Ser. No. 12/674,991 filed Feb. 24, 2010, which is a National Stage application of International Application No. PCT/EP2008/061136, filed Aug. 26, 2008, which claims the benefit of U.S. Provisional Application No. 60/968,109 filed Aug. 27, 2007, the entire contents of which is hereby incorporated herein by reference.

The present invention relates to novel pyrazole compounds which can be used for combating or controlling invertebrate pests, in particular arthropod pests. The invention also relates to a method for controlling invertebrate pests by using these compounds. The present invention also relates to seed and to an agricultural and veterinary composition comprising said compounds.

BACKGROUND OF INVENTION

Invertebrate pests and in particular arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

WO 2003/106427 describes N-arylamides of pyrazole carboxylic acids, wherein the pyrazole ring carries a 2-pyridyl radical in the ortho-position of the carboxamide group. The compounds are mentioned to be useful for combating invertebrate pests.

WO 2004/046129 describes 2-((1-arylpyrazol-5-yl)carbonylamino substituted benzoic amide compounds, which are mentioned to be useful for combating invertebrate pests.

JP 2007-77106 describes N-arylamides of 1-(3-chloropyridine-2-yl)-pyrazol-5-ylcarboxylic acid, which are mentioned to be useful for combating invertebrate pests.

CN 1927838 describes aromatic and heteroaromatic N-pyridinylcarboxamides useful as agrochemical bactericides and fungicides.

It is an object of the present invention to provide compounds that have a good pesticidal activity, in particular insecticidal activity, and show a broad activity spectrum against a large number of different invertebrate pests, especially against difficult to control insects.

It has been found that these objectives can be achieved by compounds of the formulae I and II below and by their salts, in particular their agriculturally or veterinarily acceptable salts.

In a first aspect the present invention relates the use controlling invertebrate pests which method comprises treating the pests, their food supply, their habitat or their breeding ground or a plant, seed, soil, area, material or environment in which the pests are growing or may grow, or the materials, plants, seeds, soils, surfaces or spaces to be protected from pest attack or infestation with a pesticidally effective amount of a pyrazole compound of the formulae I or II or a salt or N-oxide thereof:

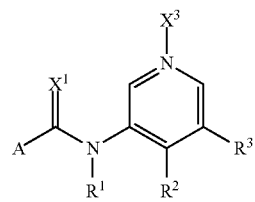

(I)

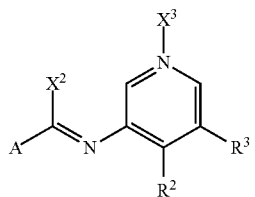

(II)

wherein
A is a pyrazole radical of the formulae A1, A2 or A3

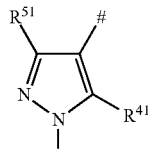

A1

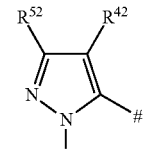

A2

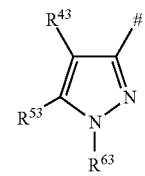

A3 denotes the binding site to the remainder of formulae I or II;
$X^1$ is S, O or $NR^{1a}$;
$X^2$ is $OR^{2a}$, $NR^{2b}R^{2c}$, $S(O)_mR^{2d}$;
$X^3$ is a lone pair or oxygen;
$R^1$ is hydrogen, CN, $C_1$-$C_{10}$-alkyl, $C_1$-$C_{10}$-haloalkyl, $C_3$-$C_{10}$-cycdoalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_4$-alkylen-CN, $OR^a$, $C_1$-$C_4$-alkylen-$OR^a$, $C(Y)R^b$, $C_1$-$C_4$-alkylen-$C(Y)R^b$, $C(Y)OR^c$, $C_1$-$C_4$-alkylen-$C(Y)OR^c$, $S(O)_2R^d$, $NR^eR^f$, $C_1$-$C_4$-alkylen-$NR^eR^f$, $C(Y)NR^gR^h$, $C_1$-$C_4$-alkylen-$C(Y)NR^gR^h$, $S(O)_mNR^eR^f$, $C(Y)NR^iNR^eR^f$, phenyl, hetaryl, phenyl-$C_1$-$C_4$-alkyl and hetaryl-$C_1$-$C_4$-alkyl wherein the aromatic ring of the four last mentioned radicals may be unsubstituted or may carry 1, 2, 3, 4 or 5 identical or different substituents $R^x$;
$R^2$ is hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsufinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$R^3$ is hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsufinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

m is 0, 1 or 2;

$R^{41}$, $R^{42}$, $R^{43}$ are selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, phenyl, phenyl$C_1$-$C_4$-alkyl, phenoxy-$C_1$-$C_4$-alkyl, 5-membered hetaryl and heterocyclyl$C_1$-$C_4$-alkyl wherein heterocyclyl and the aromatic ring of the 5 last mentioned radicals may be unsubstituted or may carry 1, 2, 3, 4 or 5 identical or different substituents $R^x$;

$R^{51}$ is selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, phenyl, phenyl$C_1$-$C_4$-alkyl, phenoxy-$C_1$-$C_4$-alkyl, 5-membered hetaryl and heterocyclyl$C_1$-$C_4$-alkyl wherein heterocyclyl and the aromatic ring of the 5 last mentioned radicals may be unsubstituted or may carry 1, 2, 3, 4 or 5 identical or different substituents $R^x$;

$R^{52}$, $R^{53}$ are selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, heterocyclyl, phenyl, phenyl-$C_1$-$C_4$-alkyl, phenoxy-$C_1$-$C_4$-alkyl and heterocyclyl-$C_1$-$C_4$-alkyl wherein heterocycyl and the aromatic ring of the 5 last mentioned radicals may be unsubstituted or may carry 1, 2, 3, 4 or 5 identical or different substituents $R^x$;

$R^{61}$, $R^{63}$ are selected from the group consisting of hydrogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, heterocyclyl, phenyl, phenyl-$C_1$-$C_4$-alkyl, phenoxy-$C_1$-$C_4$-alkyl and heterocyl-$C_1$-$C_4$-alkyl wherein the heterocyclyl and aromatic ring of the 5 last mentioned radicals may be unsubstituted or may carry 1, 2, 3, 4 or 5 identical or different substituents $R^x$;

$R^{62}$ is selected from the group consisting of hydrogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$;

Y is O or S;

$R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2a}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2b}$, $R^{2c}$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2d}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ is selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy$C_1$-$C_4$-alkyl, $R^y$ are independently of each other selected from $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl and $C_1$-$C_{10}$-alkylcarbonyl.

In a second aspect, the present invention provides a method for controlling invertebrate pests which method comprises treating the pests, their food supply, their habitat or their breeding ground or a plant, plant propagation material (such as seed), soil, area, material or environment in which the pests are growing or may grow, or the materials, plants, plant propagation materials (such as seeds), soils, surfaces or spaces to be protected from pest attack or infestation with a pesticidally effective amount of a pyrazole compound of the formulae I or II or a salt or N-oxide thereof or with a pesticidally effective amount of an agricultural composition containing at least one pyrazole compound of the formulae I or II or a salt or N-oxide thereof.

In a third aspect, the present invention provides a method for protecting seed and/or the plants which grow therefrom, against infestation by invertebrate pests, which method comprises treating the seed with a pesticidally effective amount of a compound of the formulae I or II or an agriculturally acceptable salt or N-oxide thereof. A further object of the present invention is seed, comprising at least one compound of formulae I or II and/or an agriculturally acceptable salt or N-oxide thereof.

The invention further provides a method for treating or protecting an animal from infestation or infection by parasites which comprises bringing the animal in contact with a parasiticidally effective amount of a compound of the formulae I or II or a veterinally acceptable salt or N-oxide thereof as defined above. Bringing the animal in contact with the compound I or II, its salt or the veterinary composition of the invention means applying or administering it to the animal.

So far, the compounds of the formulae I and II and their salts have not yet been described, except for compounds of the formula I, wherein A is of the formula A2, $X^1$ is O, $R^1$, $R^2$, $R^3$, $R^{42}$ and $R^{62}$ are each hydrogen, and $R^{53}$ is 2-hydroxyphenyl, 2-hydroxy-5-methylphenyl, 2-hydroxy-5-ethylphenyl, 2-hydroxy-5-chlorophenyl, 2-hydroxy-4,5-dimethylphenyl, 2-hydroxy-3,4-dimethylphenyl or 2-hydroxy-3,5-dimethylphenyl, A is of the formula A3, $X^1$ is O, $R^1$, $R^2$, $R^3$, $R^{43}$ and $R^{63}$ are each hydrogen, and $R^{53}$ is phenyl, 4-fluorophenyl, 4-methoxyphenyl, 4-bromophenyl, 4-chlorophenyl, 4-methylphenyl, 4-ethoxyphenyl, 2,4-dimethylphenyl, 2-hydroxyphenyl, 2-hydroxy-5-methylphenyl, 2-hydroxy-5-ethylphenyl, 2-hydroxy-5-chlorophenyl, 2-hydroxy-4,5-dimethylphenyl, 2-hydroxy-3,4-dimethylphenyl or 2-hydroxy-3,5-dimethylphenyl, $X^1$ is O, $R^1$, $R^2$ and $R^3$ are each hydrogen and A is 1-(phenylmethyl)-3-nitropyrazol-5-yl, 1-methylpyrazol-5-yl, 1-methyl-4-chloropyrazol-5-yl, 1-ethyl-4-bromopyrazol-3-yl, 1-ethyl-3-methylpyrazol-4-yl, 1-methyl-3-trifluormethylpyrazol-4-yl, 1-phenyl-5-benzoylaminopyrazol-4-yl, 1-(4-chlorophenyl)-3-phenylaminocarbonyl-5-methylpyrazol-4-yl, 1-phenyl-5-[(4-methylphenyl)carbonyl]aminopyrazol-4-yl, 4-iodopyrazol-3-yl, 1-methylpyrazol-3-yl, 5-chloro-1-methylpyrazol-3-yl, 5-nitropyrazol-3-yl, 1-(4-chlorophenyl)-5-trifluoromethylpyrazol-4-yl, 1-phenyl-3-thiophen-2-ylpyrazol-4-yl, 1-phenyl-3,5-dimethylpyrazol-4-yl, 4-bromo-5-nitropyrazol-3-yl or 5-cyclopropyl-1-(1,1-dioxotetrahydrothiophen-3-yl)-1H-pyrazol-3-yl;

and except for the following compounds:
1-(4-Chlorophenyl)-5-trifluoromethyl-1H-pyrazole-4-carboxylic acid pyridin-3-ylamide,
1-Phenyl-3-thiophen-2-yl-1H-pyrazole-4-carboxylic acid pyridin-3-ylamide,
3,5-Dimethyl-1-phenyl-1H-pyrazole-4-carboxylic acid pyridin-3-ylamide, Therefore, the novel pyrazole compounds of the formulae I and II and their salts, in particular their agriculturally or veterinarily acceptable salts, and their N-oxides are also part of the invention.

Another object of the present invention is an agricultural composition containing at least one novel pyrazole compound of the formulae I or II as defined above and/or an agriculturally acceptable salt or an N-oxide thereof and at least one liquid or solid carrier.

Another object of the present invention is a veterinary composition containing at least one novel pyrazole compound of the formulae I or II as defined above and/or a veterinarily acceptable salt or an N-oxide thereof and at least one veterinarily acceptable liquid or solid carrier.

The present invention further relates to plant propagation material, such as seed, comprising at least one compound of formulae I or II as defined herein.

The present invention further relates to the use of compounds of formulae I or II as defined herein for controlling invertebrate pests.

In the compounds of formulae I or II the substituents on A or the pyridyl ring may contain one or more centers of chirality. In this case the compounds of the formulae I or II can be present in the form of different enantiomers or diastereomers, depending on the substituents. In caseof the formula II, the compound II may also exist as a cis- or trans-isomer with respect to the N=C axis. The present invention relates to every possible stereoisomer of the compounds of general formulae I or II, i.e. to single enantiomers or diastereomers, as well as to mixtures thereof.

The compounds of formulae I or II may be amorphous or may exist in one or more different crystalline states (polymorphs) which may have a different macroscopic properties such as stability or show different biological properties such as activities.

The present invention includes both amorphous and crystalline compounds of formulae I or II, mixtures of different crystalline states of the respective compound I or II, as well as amorphous or crystalline salts thereof.

Salts of the compounds of the formulae I or II are preferably agriculturally and veterinarily acceptable salts. They can be formed in a customary method, e.g. by reacting the compound with an acid of the anion in question if the compound of formula I has a basic functionality or by reacting an acidic compound of formulae I or II with a suitable base.

Agriculturally useful salts of the compounds I and II encompass especially the salts of those cations or the acid addition salts of those acids whose cations and anions, respectively, have no adverse effect on the pesticidal action of the compounds I or II. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formulae (I) and (II) with an acid of the corresponding anion, preferably of hydrochloric acid, hydrobromic acid, sulfuric acid, phosphoric acid or nitric acid.

Veterinarily acceptable salts of the compounds of formula (I) encompass especially the salts of those cations or the acid addition salts which are known and accepted in the art for the formation of salts for veterinary use. Suitable acid addition salts, e.g. formed by compounds of formulae I or II containing a basic nitrogen atom, e.g. an amino group, include salts with inorganic acids, for example hydrochlorids, sulphates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The term "N-oxide" includes any compound of the formulae I or II which, apart from the pyridine nitrogen that carries the moiety $X^3$, has at least one tertiary nitrogen atom that is oxidized to an N-oxide moiety.

The term "invertebrate pest" as used herein encompasses animal populations, such as insects, arachnids and nematodes, which may attack plants thereby causing substantial damage to the plants attacked, as well as ectoparasites which may infest animals, e.g. mammals, birds or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat. Protoc. 2007; 2(5):1225-35., Curr. Opin. Chem. Biol. 2006 October; 10(5): 487-91. Epub 2006 Aug. 28., Biomaterials. 2001 March; 22(5):405-17, Bioconjug Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfiekld summer rape (Canola) being tolerant to imidazolinones, e.g. imazamox. Genetic engineering methods have been used to render cultivated plants, such as soybean, cotton, cornm, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora* infestans derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxyalkyl, alkylamino, dialkylamino, alkylcarbonyl, alkylthio, alkylsulfinyl and alkylsulfonyl denotes in each case a straight-chain or branched alkyl group having usually from 1 to 10 carbon atoms, frequently from 1 to 6 carbon atoms, preferably 1 to 4 carbon atoms. Examples of an alkyl group are methyl, ethyl, n-propyl, iso-propyl, n-butyl, 2-butyl, iso-butyl, tertbutyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-oxtyl, 1-methyloctyl, 2-methylheptyl, 1-ethylhexyl, 2-ethylhexyl, 1,2-dimethylhexyl, 1-propylpentyl and 2-propylpentyl.

The term "haloalkyl" as used herein and in the haloalkyl moieties of haloalkylthio and haloalkylsulfonyl, denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, heptafluoroisopropyl and the like.

The term "alkoxy" as used herein denotes in each case a straight-chain or branched alkyl group which is bound via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloyx, 2-methylpentyloxy, 3-methylpentyloxy, 4-methylpentyloxy, 1,1-dimethylbutyloyx, 1,2-dimethylbutyloxy, 1,3-dimethylbutyloxy, 2,2-dimethylbutyloxy, 2,3-dimethylbutyloyx, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylpentyloxy, n-oxtyloxy, 1-methyloctyloxy, 2-methylheptyloxy, 1-ethylhexyloxy, 2-ethylhexyloxy, 1,2-dimethylhexyloxy, 1-propylpentoxy and 2-propylpentyloxy.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and the like.

The term "cycloalkyl" as used herein and in the cycloalkyl moieties of $C_3$-$C_{10}$-cycloalkylmethyl denotes in each case a mono- or bicyclic cycloaliphatic radical having usually from 3 to 10 C atoms or 3 to 6 C atoms, such as cyclopropyl, cyclobutyl, cyclopentyl, cyclohexyl, cycloheptyl, cyclooctyl, bicycio[2.1.1]hexyl, bicyclo[3.1.1]heptyl, bicyclo[2.2.1] heptyl, and bicyclo[2.2.2]octyl.

The term "halocycloalkyl" as used herein and in the halocycloalkyl moieties of $C_3$-$C_{10}$-halocycloalkyl-methyl denotes in each case a mono- or bicyclic cycloaliphatic radical having usually from 3 to 10 C atoms or 3 to 6 C atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "alkenyl" as used herein denotes in each case a singly unsaturated hydrocarbon radical having usually 2 to 10, e.g. 2, 3, 4, 5, 6, 7 or 8 C-atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 10, e.g. 2, 3, 4, 5, 6, 7 or 8 C-atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "$C_1$-$C_4$-alkoxy-$C_1$-$C_4$-alkyl" as used herein refers to $C_1$-$C_4$-alkyl wherein 1 carbon atom carries a $C_1$-$C_4$-alkoxy radical as mentioned above. Examples are $CH_2OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkylthio "(alkylsulfanyl: alkyl-S—)" as used herein refers to a straight-chain or branched saturated alkyl group having 1 to 10 carbon atoms, preferably 1 to 4 carbon atoms (=$C_1$-$C_4$-alkylthio) (as mentioned above) which is attached via a sulfur atom.

The term "haloalkylthio" as used herein refers to a alkylthio group as mentioned above wherein the hydrogen atoms are partially or fully substituted by fluorine, chlorine, bromine and/or iodine.

The term "alkylsulfinyl" (alkylsulfoxyl: $C_1$-$C_6$-alkyl-S(=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl) bonded through the sulfur atom of the sulfinyl group at any position in the alkyl group.

The term "haloalkylsulfinyl" as used herein refers to a alkylsulfinyl group as mentioned above wherein the hydrogen atoms are partially or fully substituted by fluorine, chlorine, bromine and/or iodine.

The term "alkylsulfonyl" (alkyl-S(=O)$_2$—) as used herein refers to a straight-chain or branched saturated alkyl group having 1 to 10 carbon atoms, preferably 1 to 4 carbon atoms (=$C_1$-$C_4$-alkylsulfonyl) (as mentioned above) which is bonded via the sulfur atom of the sulfonyl group at any position in the alkyl group.

The term "haloalkylsulfonyl" as used herein refers to a alkylsulfonyl group as mentioned above wherein the hydrogen atoms are partially or fully substituted by fluorine, chlorine, bromine and/or iodine.

The term "heterocyclyl" includes in general 5-, 6-, 7- or 8-membered monoheterocyclic radicals and 8 to 10 membered bicyclic heterocyclic radicals, the mono- and bicyclic radicals may be saturated, unsaturated or aromatic (=hetaryl). The mono- and bicyclic heterocyclic radicals as usually comprise 1, 2, 3 or 4 heteroatoms selected from N, O and S as ring members.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

Examples of saturated or unsaturated membered heterocyclic rings comprise saturated or unsaturated, non-aromatic heterocyclic rings, such as pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, dihydrothiopyranyl, tetrahydrothiopyranyl, morpholinyl, thiazinyl and the like. Examples for heterocyclic ring also comprising 1 or 2 carbonyl groups as ring members comprise pyrrolidin-2-only, pyrrolidin-2,5-dionyl, imidazolidin-2-only, oxazolidin-2-only, thiazolidin-2-only and the like.

The terms "phenyl-$C_1$-$C_4$-alkyl" and "phenoxy-$C_1$-$C_4$-alkyl" refers to phenyl or phenoxy, respectively, which are bound via a $C_1$-$C_4$-alkyl group, in particular a methyl group (=hetarylmethyl), to the remainder of the molecule, examples including benzyl, 1-phenylethyl, 2-phenylethyl, 2-phenoxyethyl etc.

The terms "heterocyclyl-$C_1$-$C_4$-alkyl" and "hetaryl-$C_1$-$C_4$-alkyl" refers to heterocycyl or hetaryl, respectively, as defined above which are bound via a $C_1$-$C_4$-alkyl group, in particular a methyl group (=heterocyclylmethyl or hetarylmethyl, respectively), to the remainder of the molecule.

The remarks made below as to preferred embodiments of the variables of the compounds of the formulae I or II, of the features of the use and method according to the invention and of the composition of the invention are valid on their own as well as preferably—in combination with each other.

A preferred embodiment of the invention relates to pyrazole compounds of the formula I, to their salts, to their N-oxides and to the methods and uses of such compounds. Amongst the compounds of the formula I, preference is given to those compounds, wherein $X^1$ in formula I is oxygen, sulphur or a moiety N—$R^{1a}$. Particular preference is given to those compounds of the formula I wherein $X^1$ is oxygen.

In the compounds of the formula I, wherein X is $NR^{1a}$, a particular embodiment relates to those compounds, wherein $R^{1a}$ is $C_1$-$C_6$-alkyl, $C_1$-$C_6$-haloalkyl, $C_3$-$C_6$-cycloalkyl, $C_3$-$C_6$-cycloalkylmethyl, $C_3$-$C_6$-halocycloalkyl, $C_2$-$C_6$-alkenyl, $C_2$-$C_6$-haloalkenyl, $C_2$-$C_6$-alkynyl, $C_1$-$C_4$-alkoxy-$C_1$-$C_6$-alkyl, phenyl, hetaryl, phenyl-$C_1$-$C_4$-alkyl and hetarylC$_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, or a moiety $OR^a$. In particular, $R^{1a}$ is $C_1$-$C_6$-alkyl, $C_3$-$C_6$-cycloalkylmethyl, $C_3$-$C_6$-alkenyl, $C_3$-$C_6$-alkynyl, $C_1$-$C_4$-alkoxyC$_1$-$C_4$-alkyl or a moiety $OR^a$, wherein Ra is as defined above and in particular selected from $C_1$-$C_6$-alkyl, $C_3$-$C_6$-cycloalkylmethyl, $C_3$-$C_6$-alkenyl, $C_3$-$C_6$-alkynyl and $C_1$-$C_4$-alkoxy-$C_1$-$C_4$-alkyl.

Amongst the compounds of the formula I, preference is given to those compounds, wherein $R^1$ is hydrogen, CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_4$-alkoxy-$C_1$-$C_{10}$-alkyl, $C_1$-$C_4$-alkylene-CN, $OR^a$, $C(Y)R^b$, $C(Y)OR^c$ or $S(O)_2R^d$. More preference ist given to compounds of formula I, wherein $R^1$ is hydrogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_4$-alkoxy-$C_1$-$C_{10}$-alkyl or $C_1$-$C_4$-alkylene-CN, in particular hydrogen, $C_1$-$C_3$-alkyl or $C_1$-$C_4$-alkylene-CN, in particular hydrogen, methyl or ethyl.

Another embodiment of the invention relates to pyrazole compounds of the formula II, to their salts, to their N-oxides and to the methods and uses of such compounds. In the compounds of the formula II, preference is given to those compounds, wherein $X^2$ in formula II is $OR^{2a}$ or $SR^{2a}$. In these compounds $R^{2a}$ is preferably $C_1$-$C_6$-alkyl, $C_3$-$C_6$-alkenyl, $C_3$-$C_6$-alkynyl, $C_3$-$C_6$-cycloalkylmethyl or $C_1$-$C_4$-alkoxy-$C_1$-$C_{10}$-alkyl. Another embodiment relates to compounds of the formula I, wherein $X^2$ is $NR^{2b}R^{2c}$. In these compounds $R^{2b}$ and $R^C$ are preferably selected, independently of each other, from $C_1$-$C_6$-alkyl, $C_3$-$C_6$-cycloalkylmethyl or $C_1$-$C_4$-alkoxy-$C_1$-$C_{10}$-alkyl or $R^{2b}$ and $R^{2c}$, together with the nitrogen atom to which they are attached, form a saturated, nitrogenbound 5- or 6-membered heterocycle which may comprise a further heteroatom selected from O, S and N, e.g. $NR^{2b}R^{2c}$ being 1-pyrrolidinyl, 1-piperidinyl, 1-piperazinyl, 4-morpholinyl or 4-thiomorpholinyl.

In the methods and uses and amongst the compounds according to the present invention, preference is given to the compounds, methods and uses, wherein $R^2$ in formulae I and II is selected from hydrogen, methyl, difluoromethyl, trifluoromethyl, methoxy, difluoromethoxy and trifluoromethoxy.

In the methods and uses and amongst the compounds according to the present invention, preference is given to the compounds, methods and uses, wherein $R^3$ in formulae I and II is selected from hydrogen, methyl, difluoromethyl, trifluoromethyl, methoxy, difluoromethoxy and trifluoromethoxy.

In particular, at least one of the radicals $R^2$ or $R^3$ in formulae I and II is hydrogen. A very preferred embodiment of the invention relates to compounds of the formulae I and II and to their salts, wherein both $R^2$ and $R^3$ are hydrogen.

Another preferred embodiment of the invention relates to compounds of the formulae I and II and to their salts and to their N-oxides, wherein $R^2$ is hydrogen and $R^3$ is selected from hydrogen, methyl, difluoromethyl, trifluoromethyl, methoxy, difluoromethoxy and trifluoromethoxy. Another preferred embodiment of the invention relates to compounds of the formulae I and II and to their salts, wherein $R^3$ is hydrogen and $R^2$ is selected from hydrogen, methyl, difluoromethyl, trifluoromethyl, methoxy, difluoromethoxy and trifluoromethoxy.

A preferred embodiment of the invention relates to pyrazole compounds of the formulae I and II, to their salts, to their N-oxides and to the methods and uses of such compounds, wherein A is a radical A1. Amongst these, preference is given to compounds of the formula I, wherein $X^1$, $R^1$, $R^2$ and $R^3$ are as defined above and in particular have one of the preferred meanings.

In the pyrazole compounds of the formulae I and II, wherein A is a radical A1, $R^{41}$ and $R^{51}$ are preferably selected, independently of each other, from independently selected from hydrogen, halogen, CN, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$. In particular, $R^{41}$ and $R^{51}$ are selected, independently of each other, from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl, and more preferably from hydrogen, halogen, CN, $CH_3$, $CH_2F$, $CHF_2$ and $CF_3$.

Preferably, at least one or both of the radicals $R^{41}$ and $R^{51}$ are hydrogen. In particular, either $R^{41}$ or $R^{51}$ is selected from halogen, CN, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$, while the remaining radical $R^{41}$ or $R^{51}$ is hydrogen or halogen, in particular hydrogen. More preferably, either $R^{41}$ or $R^{51}$ is selected from halogen, CN, $C_1$-$C_4$-alkyl, $C_1$-$C_4$-haloalkyl, $C_3$-$C_6$-cycloalkyl and $C_3$-$C_6$-halocycloalkyl, and most preferably from halogen, CN, $CH_3$, $CH_2F$, $CHF_2$ and $CF_3$, while the remaining radical $R^{41}$ or $R^{51}$ is hydrogen.

In the pyrazole compounds of the formulae I and II, wherein A is a radical A1, $R^{61}$ is preferably selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy$C_1$-$C_{10}$-alkyl, phenyl, benzyl, phenoxy-methyl, 5- or 6-membered hetaryl, 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{61}$ is $C_1$-$C_4$-alkyl or $C_1$-$C_4$-haloalkyl, in particular methyl, ethyl, n-propyl, isopropyl, difluoromethyl, trifluoromethyl, 2-fluoroethyl, 2,2-difluoroethyl and 2,2,2-trifluoroethyl. Likewise preferred are compounds of the formulae I and II, wherein A is a radical A1, wherein $R^{41}$ and $R^{51}$ are as defined herein and wherein $R^{61}$ is selected from phenyl, benzyl and 5- or 6-membered hetaryl, in particular pyridyl, pyrazolyl, imidazolyl, oxazolyl, thiazolyl, isoxazolyl, isothiazolyl, 1,2,4-thiadiazolyl, 1,3,4-thiadiazolyl, 1,2,3-triazolyl, 1,2,4-triazolyl or tetrazolyl, wherein the aromatic moiety in phenyl, benzyl and 5- or 6-membered hetaryl is unsubstituted or may carry 1, 2 or 3 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

Examples of suitable radicals A1 are the radicals for the formulae A1.a, A1.b, A1.c, A1.d, A1.e, A1.f, A1.g, A1.h, A1.i, A1.k, A1.l, A1.m, A1.n, A1.o, A1.p, A1.q, A1.r, A1.s, A1.t, A1.u, A1.v, A1.w, A1.x, A1.y and A1.z, wherein $R^{61}$ is as defined in one row of table A1 (radicals A1.a1-A1.a81 to A1.z1-A1.z81):

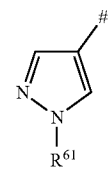

A1.a

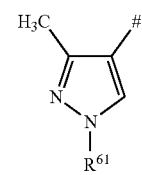

A1.b

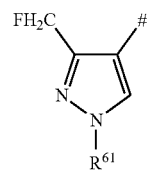

A1.c

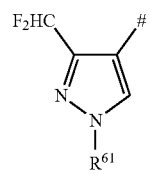

A1.d

| | |
|---|---|
| 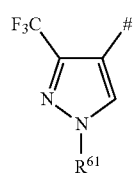 A1.e | 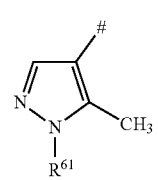 A1.o |
| 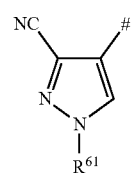 A1.f | 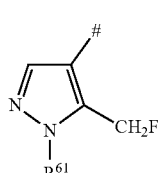 A1.p |
| 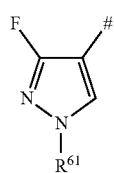 A1.g | 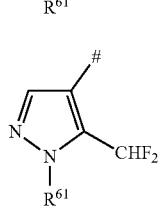 A1.q |
| 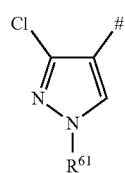 A1.h | 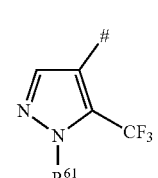 A1.r |
| 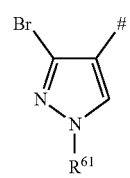 A1.i | 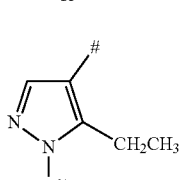 A1.s |
| 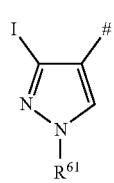 A1.k | 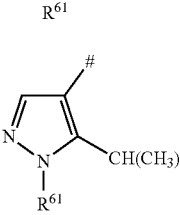 A1.t |
| 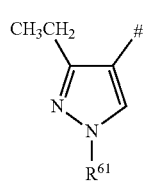 A1.l | 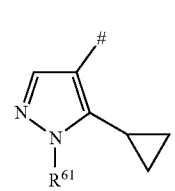 A1.u |
| 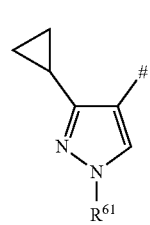 A1.m | 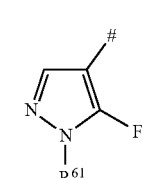 A1.v |
| 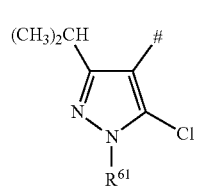 A1.n | 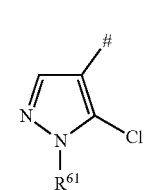 A1.w |

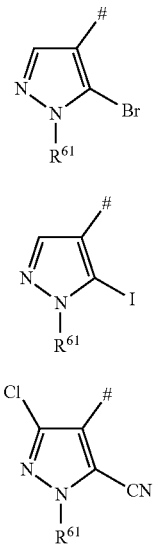

TABLE A1

| | $R^{61}/R^{52}$ |
|---|---|
| 1 | H |
| 2 | CH$_3$ |
| 3 | CH$_2$CH$_3$ |
| 4 | CH$_2$CH$_2$CH$_3$ |
| 5 | CH(CH$_3$)$_2$ |
| 6 | CH$_2$CF$_3$ |
| 7 | C(CH$_3$)$_3$ |
| 8 | C$_6$H$_5$ |
| 9 | 4-Cl—C$_6$H$_4$ |
| 10 | 4-F—C$_6$H$_4$ |
| 11 | 2,4-Cl$_2$—C$_6$H$_3$ |
| 12 | 4-(CH$_3$O)—C$_6$H$_4$ |
| 13 | 2-pyridyl |
| 14 | 5-chloro-2-pyridyl |
| 15 | CH$_2$—C$_6$H$_5$ |
| 16 | 4-(OCF$_3$)—C$_6$H$_4$ |
| 17 | 4-(SCF$_3$)—C$_6$H$_4$ |
| 18 | 4-(OCHF$_2$)—C$_6$H$_4$ |
| 19 | 4-(CF(CF$_3$)$_2$)—C$_6$H$_4$ |
| 20 | 4-(SO$_2$CH$_3$)—C$_6$H$_4$ |
| 21 | 2,6-Cl-4-CF$_3$—C$_6$H$_2$ |
| 22 | 3-chloro-5-trifluoro-methylpyridine-2-yl |
| 23 | 3-pyridyl |
| 24 | 4-pyridyl |
| 25 | 2-thiazolyl |
| 26 | 4,5-dimethyl-thiazol-2-yl |
| 27 | 4-thiazolyl |
| 28 | 5-thiazolyl |
| 29 | 4-trifluormethyl-thiazol-2-yl |
| 30 | 4-methylthiazol-2-yl |
| 31 | 4-phenylthiazol-2-yl |
| 32 | 5-triazolyl |
| 33 | 3-methyl-triazol-5-yl |
| 34 | 4-chlorobenzyl |
| 35 | 4-nitro-1-pyrazolyl-methyl |
| 36 | 2-imidazolyl |
| 37 | 4-imidazolyl |
| 38 | 5-imidazolyl |
| 39 | 2-oxazolyl |
| 40 | 4-oxazolyl |
| 41 | 5-oxazolyl |
| 42 | 3-isoxazolyl |
| 43 | 4-isoxazolyl |
| 44 | 5-isoxazolyl |
| 45 | 3-methylisoxazol-5-yl |
| 46 | 5-methylisoxazol-3-yl |
| 47 | 3-pyrazolyl |

TABLE A1-continued

| | $R^{61}/R^{52}$ |
|---|---|
| 48 | [1,3,4]thiadiazol-2-yl |
| 49 | 5-tetrazolyl |
| 50 | 4-NO$_2$—C$_6$H$_4$ |
| 51 | 4-CF$_3$—C$_6$H$_4$ |
| 52 | 2,4-F$_2$—C$_6$H$_3$ |
| 53 | 3,5-Cl$_2$—C$_6$H$_3$ |
| 54 | 3,4-Cl$_2$—C$_6$H$_3$ |
| 55 | 4-C(CH$_3$)$_3$—C$_6$H$_4$ |
| 56 | 3-Cl—C$_6$H$_4$ |
| 57 | 3-F—C$_6$H$_4$ |
| 58 | 2-F—C$_6$H$_4$ |
| 59 | 2-CF$_3$—C$_6$H$_4$ |
| 60 | 2-CH$_3$O—C$_6$H$_4$ |
| 61 | 3-CH$_3$O—C$_6$H$_4$ |
| 62 | 3-Cl-4-F—C$_6$H$_3$ |
| 63 | 3-NO$_2$—C$_6$H$_4$ |
| 64 | 2-CH$_3$—C$_6$H$_4$ |
| 65 | 3-CH$_3$—C$_6$H$_4$ |
| 66 | 4-CH$_3$—C$_6$H$_4$ |
| 67 | 2-phenyl—C$_6$H$_4$ |
| 68 | 3-phenyl—C$_6$H$_4$ |
| 69 | 2-F-4-Cl—C$_6$H$_3$ |
| 70 | 2,4,6-Cl$_3$—C$_6$H$_2$ |
| 71 | 2,3,4-Cl$_3$—C$_6$H$_2$ |
| 72 | 2,6-F$_2$—C$_6$H$_3$ |
| 73 | CH$_2$F |
| 74 | CHF$_2$ |
| 75 | CF$_3$ |
| 76 | CH$_2$CHF$_2$ |
| 77 | CH$_2$Cl |
| 78 | CHCl$_2$ |
| 79 | CCl$_3$ |
| 80 | CH$_2$CHCl$_2$ |
| 81 | CH$_2$CCl$_3$ |

Here and in the following tables C$_6$H$_5$ denotes phenyl, CH$_2$—C$_6$H$_5$ denotes benzyl, 4-Cl—C$_6$H$_4$ denotes 4-chlorophenyl, 4-F—C$_6$H$_4$ denotes 4-fluorophenyl, 4-(CH$_3$O)—C$_6$H$_4$ denotes 4-methoxyphenyl, 2,4-Cl$_2$—C$_6$H$_3$ denotes 2,4-dichlorophenyl, 4-(CF(CF$_3$)$_2$)—C$_6$H$_4$ denotes 4-(1,2,2,2-tetrafluoro-1-(trifluoromethyl)ethyl)phenyl, 4-(OCF$_3$)—C$_6$H$_4$ denotes 4-(trifluoromethoxy)phenyl, 4-(SCF$_3$)—C$_6$H$_4$ denotes 4-(trifluoromethylsulfanyl)phenyl, 4-(OCHF$_2$)—C$_6$H$_4$ denotes 4-(difluoromethoxy)phenyl, 4-(SO$_2$CH$_3$)—C$_6$H$_4$ denotes 4-(methylsulfonyl)phenyl, 2,6-Cl$_4$-CF$_3$—C$_6$H$_2$ denotes 2,6-dichloro-4-(trifluoromethyl)phenyl, 4-NO$_2$—C$_6$H$_4$ denotes 4-nitrophenyl, 4-CF$_3$—C$_6$H$_4$ denotes 4-(trifluoromethyl)phenyl, 2,4-F$_2$—C$_6$H$_3$ denotes 2,4-difluorophenyl, 3,5-Cl$_2$-C$_6$H$_3$ denotes 3,5-dichlorophenyl, 3,4-Cl$_2$-C$_6$H$_3$ denotes 3,4-dichlorophenyl, 4-C(CH$_3$)$_3$—C$_6$H$_4$ denotes 4-tert.-butylphenyl, 3-Cl—C$_6$H$_4$ denotes 3-chlorophenyl, 3-F—C$_6$H$_4$ denotes 3-fluorophenyl, 2-F—C$_6$H$_4$ denotes 2-fluorophenyl, 2-CF$_3$—C$_6$H$_4$ denotes 2-(trifluoromethyl)phenyl, 2-CH$_3$O—C$_6$H$_4$ denotes 2-methoxyphenyl, 3-CH$_3$O—C$_6$H$_4$ denotes 3-methoxyphenyl, 3-Cl-4-F—C$_6$H$_3$ denotes 3-chloro-4-fluorophenyl, 3-NO$_2$—C$_6$H$_4$ denotes 3-nitrophenyl, 2-CH$_3$—C$_6$H$_4$ denotes 2-tolyl, 3-CH$_3$—C$_6$H$_4$ denotes 3-tolyl, 4-CH$_3$—C$_6$H$_4$ denotes 4-tolyl, 2-pheny-C$_6$H$_4$ denotes biphenyl-2-yl, 3-phenyl-C$_6$H$_4$ denotes biphenyl-3-yl, 2-F-4-Cl—C$_6$H$_3$ denotes 2-fluoro-4-chlorophenyl, 2,4,6-Cl$_3$—C$_6$H$_2$ denotes 2,3,4-trichlorophenyl, 2,3,4-Cl$_3$-C$_6$H$_2$ denotes 2,3,4-trichlorophenyl, and 2,6-F$_2$—C$_6$H$_3$ denotes 2,6-difluorophenyl A further embodiment of the invention relates to pyrazole compounds of the formulae I and II, to their salts and to the methods and uses of such compounds, wherein A is a radical A2. Amongst these, preference is given to compounds of the formula I, wherein X$^1$, R$^1$, R$^2$ and R$^3$ are as defined above and in particular have one of the preferred meanings.

In the pyrazole compounds of the formulae I and II, wherein A is a radical A2, $R^{42}$ is preferably selected from hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are as defined above and which are preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. In particular, $R^{42}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl, and more preferably from hydrogen, halogen, CN, $CH_3$, $CH_2F$, $CHF_2$ and $CF_3$.

In the pyrazole compounds of the formulae I and II, wherein A is a radical A2, $R^5$ is preferably selected from the group consisting of hydrogen, halogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{52}$ is selected from the group consisting of hydrogen, halogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl and $C_1$-$C_4$-alkoxy-$C_1$-$C_{10}$-alkyl. Most preferably $R^{52}$ is hydrogen, halogen, $C_1$-$C_4$-alkyl or $C_1$-$C_4$-haloalkyl, in particular methyl, ethyl, n-propyl, isopropyl, difluoromethyl, trifluormoethyl and 2,2,2-trifluoroethyl. Likewise preferred are compounds of the formulae I and II, wherein A is a radical A2, wherein $R^{42}$ and $R^{62}$ are as defined herein and wherein $R^5$ is selected from phenyl, benzyl and 5- or 6-membered hetaryl, in particular pyridyl, pyrazolyl, imidazolyl, oxazolyl, thiazolyl, isoxazolyl, isothiazolyl, 1,2,4-thiadiazolyl, 1,3,4-thiadiazolyl, 1,2,3-triazolyl, 1,2,4-triazolyl or tetrazolyl, wherein the aromatic moiety in phenyl, benzyl and 5- or 6-membered hetaryl is unsubstituted or may carry 1, 2 or 3 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

In the pyrazole compounds of the formulae I and II, wherein A is a radical A2, R is preferably selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl and phenoxymethyl wherein the aromatic ring of the 3 last mentioned radicals may be unsubstituted or may carry 1, 2, 3, 4 or 5 identical or different substituents $R^x$ which is as defined above and more preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{62}$ is $C_1$-$C_4$-alkyl or $C_1$-$C_4$-haloalkyl, in particular methyl, ethyl, n-propyl, isopropyl, difluoromethyl, trifluormoethyl and 2,2,2-trifluoroethyl.

Examples of suitable radicals A2 are the radicals for the formulae A2.aa, A2.ab, A2.ac, A2.ad, A2.ae, A2.af, A2.ag, A2.ah, A2.ai, A2.ak, A2.al, A2.am, A2.an and A2.ao, wherein $R^{52}$ is as defined in one row of table A1 (radicals A2.aa1-A2.aa81 to A2.ao1-A2.ao81):

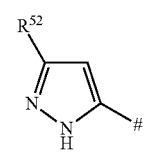 A2.aa

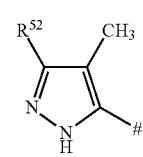 A2.ab

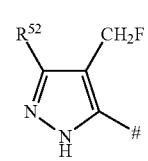 A2.ac

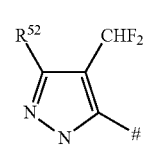 A2.ad

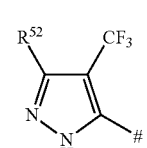 A2.ae

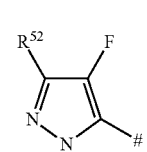 A2.af

 A2.ag

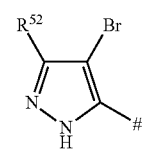 A2.ah

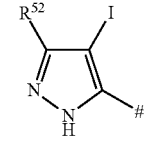 A2.ai

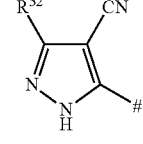 A2.ak

-continued

Further examples of suitable radicals A2 are the radicals for the formulae A2.ba, A2.bb, A2.bc, A2.bd, A2.be, A2.bf, A2.bg, A2.bh, A2.bi, A2.bk, A2.bl, A2.bm, A2.bn and A2.bo, wherein $R^{52}$ is as defined in one row of table A1 (radicals A2.ba1-A2.ba81 to A2.bo1-A2.bo81):

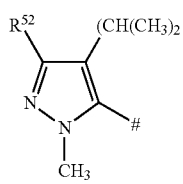 A2.bn
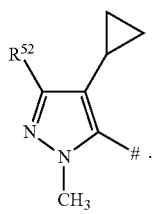 A2.bo
Further examples of suitable radicals A2 are the radicals for the formulae A2.ca, A2.cb, A2.cc, A2.cd, A2.ce, A2.cf, A2.cg, A2.ch, A2.ci, A2.ck, A2.cl, A2.cm, A2.cn and A2.co, wherein $R^{52}$ is as defined in one row of table A1 (radicals A2.ca1-A2.ca81 to A2.co1-A2.co81):
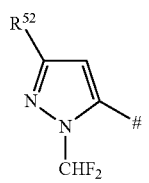 A2.ca
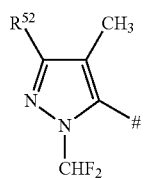 A2.cb
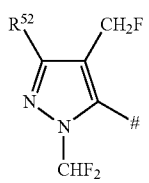 A2.cc
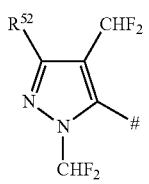 A2.cd
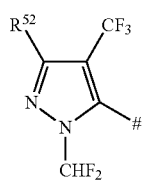 A2.ce
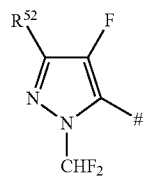 A2.cf
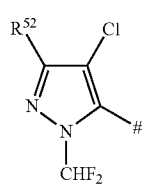 A2.cg
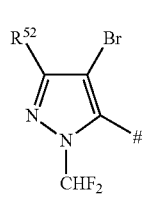 A2.ch
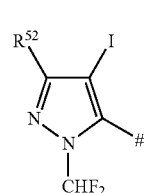 A2.ci
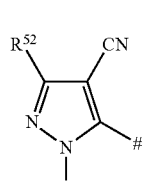 A2.ck
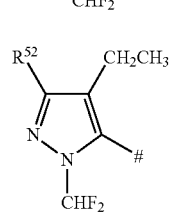 A2.cl
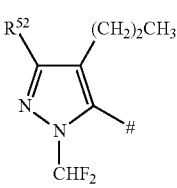 A2.cm
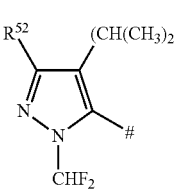 A2.cn A2.co
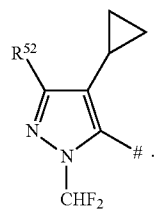

Further examples of suitable radicals A2 are the radicals for the formulae A2.da, A2.db, A2.dc, A2.dd, A2.de, A2.df, A2.dg, A2.dh, A2.di, A2.dk, A2.dl, A2.dm, A2.dn and A2.do, wherein $R^{52}$ is as defined in one row of table A1 (radicals A2.da1-A2.da81 to A2.do1-A2.do81):

A2.da
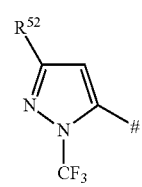

A2.db
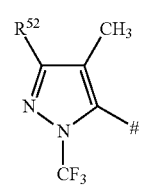

A2.dc
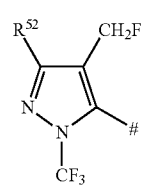

A2.dd
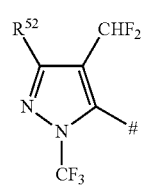

A2.de
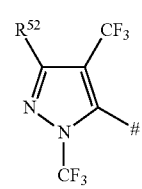

A2.df
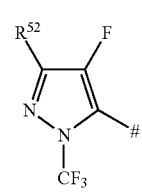

A2.dg
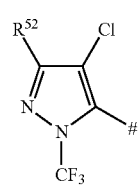

A2.dh
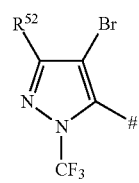

A2.di
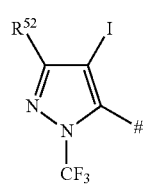

A2.dk
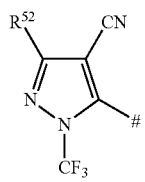

A2.dl
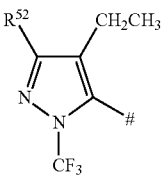

A2.dm
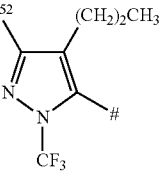

A2.dn
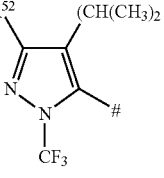

A2.do
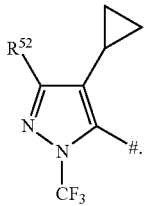

A further embodiment of the invention relates to pyrazole compounds of the formulae I and II, to their salts and to the methods and uses of such compounds, wherein A is a radical A3. Amongst these, preference is given to compounds of the formula I, wherein $X^1$, $R^1$, $R^2$ and $R^3$ are as defined above and in particular have one of the preferred meanings.

In the pyrazole compounds of the formulae I and II, wherein A is a radical A3, $R^{43}$ is preferably selected from hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are as defined above and which are preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. In particular, $R^{43}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl, and more preferably from hydrogen, halogen, CN, $CH_3$, $CH_2F$, $CHF_2$ and $CF_3$.

In the pyrazole compounds of the formulae I and II, wherein A is a radical A3, $R^{53}$ is preferably selected from the group consisting of hydrogen, halogen, $C_1$-$C_{10}$-alkyl, $C_1$-$C_{10}$-habalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-membered hetarylmethyl wherein the (hetero) aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{53}$ is selected from the group consisting of hydrogen, halogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl and $C_1$-$C_4$-alkoxy-$C_1$-$C_{10}$-alkyl. Most preferably $R^5$ is hydrogen, halogen, $C_1$-$C_4$-alkyl or $C_1$-$C_4$-haloalkyl, in particular methyl, ethyl, n-propyl, isopropyl, difluoromethyl, trifluormoethyl or 2,2,2-trifluoroethyl. Likewise preferred are compounds of the formulae I and II, wherein A is a radical A2, wherein $R^{43}$ and $R^{63}$ are as defined herein and wherein $R^5$ is selected from phenyl, benzyl and 5- or 6-membered hetaryl, in particular pyridyl, pyrazolyl, imidazolyl, oxazolyl, thiazolyl, isoxazolyl, isothiazolyl, 1,2,4-thiadiazolyl, 1,3,4-thiadiazolyl, 1,2,3-triazolyl, 1,2,4-triazolyl or tetrazolyl, wherein the aromatic moiety in phenyl, benzyl and 5- or 6-membered hetaryl is unsubstituted or may carry 1, 2 or 3 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

In the pyrazole compounds of the formulae I and II, wherein A is a radical A3, $R^{63}$ is preferably selected from the group consisting of hydrogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{53}$ is $C_1$-$C_4$-alkyl or $C_1$-$C_4$-haloalkyl, in particular methyl, ethyl, n-propyl, isopropyl, difluoromethyl, trifluormoethyl and 2,2,2-trifluoroethyl. Likewise preferred are compounds of the formulae I and II, wherein A is a radical A2, wherein $R^{43}$ and $R^{63}$ are as defined herein and wherein $R^5$ is selected from phenyl, benzyl and 5- or 6-membered hetaryl, in particular pyridyl, pyrazolyl, imidazolyl, oxazolyl, thiazolyl, isoxazolyl, isothiazolyl, 1,2,4-thiadiazolyl, 1,3,4-thiadiazolyl, 1,2,3-triazolyl, 1,2,4-triazolyl or tetrazolyl, wherein the aromatic moiety in phenyl, benzyl and 5- or 6-membered hetaryl is unsubstituted or may carry 1, 2 or 3 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

Amongst the pyrazole compounds of the formulae I and II, wherein A is a radical A3, those are particularly preferred, wherein either $R^{53}$ or $R^{63}$ is hydrogen, CN, $C_1$-$C_4$-alkyl or $C_1$-$C_4$-haloalkyl, in particular hydrogen, CN, $CH_3$, $CH_2F$, $CHF_2$ or $CF_3$, where $R^5$ may also be halogen, while the other radical $R^{53}$, $R^{63}$ is selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and in particular selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

In particular $R^{63}$ is hydrogen, CN, $C_1$-$C_4$-alkyl or $C_1$-$C_4$-haloalkyl, especially hydrogen, CN, $CH_3$, $CH_2F$, $CHF_2$ or $CF_3$, and $R^5$ is selected from $C_1$-$C_4$-alkyl, $C_1$-$C_4$-haloalkyl, in particular methyl, ethyl, n-propyl, isopropyl, difluoromethyl, trifluormoethyl and 2,2,2-trifluoroethyl, phenyl, benzyl and 5- or 6-membered hetaryl, in particular pyridyl, pyrazolyl, imidazolyl, oxazolyl, thiazolyl, isoxazolyl, isothiazolyl, 1,2, 4-thiadiazolyl, 1,3,4-thiadiazolyl, 1,2,3-triazolyl, 1,2,4-triazolyl or tetrazolyl, wherein the aromatic moiety in phenyl, benzyl and 5- or 6-membered hetaryl is unsubstituted or may carry 1, 2 or 3 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl, or $R^{53}$ is hydrogen, halogen, CN, $C_1$-$C_4$-alkyl or $C_1$-$C_4$-haloalkyl, especially hydrogen, CN, $CH_3$, $CH_2F$, $CHF_2$ or $CF_3$, and $R^6$ is selected from $C_1$-$C_4$-alkyl, $C_1$-$C_4$-haloalkyl, in particular methyl, ethyl, n-propyl, isopropyl, difluoromethyl, trifluormoethyl and 2,2,2-trifluoroethyl, phenyl, benzyl and 5- or 6-membered hetaryl, in particular pyridyl, pyrazolyl, imidazolyl, oxazolyl, thiazolyl, isoxazolyl, isothiazolyl, 1,2,4-thiadiazolyl, 1,3,4-thiadiazolyl, 1,2,3-triazolyl, 1,2,4-triazolyl or tetrazolyl, wherein the aromatic moiety in phenyl, benzyl and 5- or 6-membered hetaryl is unsubstituted or may carry 1, 2 or 3 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl Examples of suitable radicals A3 are the radicals for the formulae A3.aa, A3.ab, A3.ac, A3.ad, A3.ae, A3.af, A3.ag, A3.ah, A3.ai, A3.ak, A3.al, A3.am, A3.an and A3.ao, wherein $R^{63}$ is as defined in one row of table A3 (radicals A3.aa1-A3.aa81 to A3.ao1-A3.ao81):

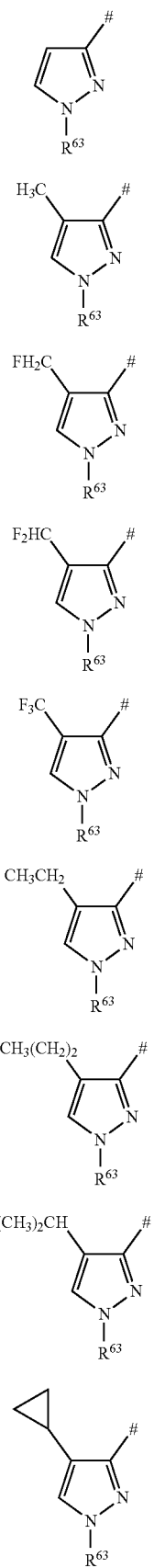

| | TABLE A3 | |
|---|---|---|
| | R⁵³/R⁶³ | |
| 1 | H | |
| 2 | $CH_3$ | |
| 3 | $CH_2CH_3$ | |
| 4 | $CH_2CH_2CH_3$ | |
| 5 | $CH(CH_3)_2$ | |
| 6 | $CH_2CF_3$ | |
| 7 | $C(CH_3)_3$ | |
| 8 | $C_6H_5$ | |
| 9 | $4\text{-Cl}—C_6H_4$ | |
| 10 | $4\text{-F}—C_6H_4$ | |
| 11 | $2,4\text{-Cl}_2—C_6H_3$ | |
| 12 | $4\text{-}(CH_3O)—C_6H_4$ | |
| 13 | 2-pyridyl | |
| 14 | 5-chloro-2-pyridyl | |
| 15 | $CH_2—C_6H_5$ | |
| 16 | $4\text{-}(OCF_3)—C_6H_4$ | |
| 17 | $4\text{-}(SCF_3)—C_6H_4$ | |
| 18 | $4\text{-}(OCHF_2)—C_6H_4$ | |
| 19 | $4\text{-}(CF(CF_3)_2)—C_6H_4$ | |
| 20 | $4\text{-}(SO_2CH_3)—C_6H_4$ | |
| 21 | $2,6\text{-Cl-4-}CF_3—C_6H_2$ | |
| 22 | 3-chloro-5-trifluoro-methylpyridine-2-yl | |
| 23 | 3-pyridyl | |
| 24 | 4-pyridyl | |
| 25 | 2-thiazolyl | |
| 26 | 4,5-dimethyl-thiazol-2-yl | |
| 27 | 4-thiazolyl | |
| 28 | 5-thiazolyl | |
| 29 | 4-trifluormethyl-thiazol-2-yl | |
| 30 | 4-methylthiazol-2-yl | |

TABLE A3-continued

| | $R^{53}/R^{63}$ |
|---|---|
| 31 | 4-phenylthiazol-2-yl |
| 32 | 5-triazolyl |
| 33 | 3-methyl-triazol-5-yl |
| 34 | 4-chlorobenzyl |
| 35 | 4-nitro-1-pyrazolyl-methyl |
| 36 | 2-imidazolyl |
| 37 | 4-imidazolyl |
| 38 | 5-imidazolyl |
| 39 | 2-oxazolyl |
| 40 | 4-oxazolyl |
| 41 | 5-oxazolyl |
| 42 | 3-isoxazolyl |
| 43 | 4-isoxazolyl |
| 44 | 5-isoxazolyl |
| 45 | 3-methylisoxazol-5-yl |
| 46 | 5-methylisoxazol-3-yl |
| 47 | 3-pyrazolyl |
| 48 | [1,3,4]thiadiazol-2-yl |
| 49 | 5-tetrazolyl |
| 50 | 4-NO$_2$—C$_6$H$_4$ |
| 51 | 4-CF$_3$—C$_6$H$_4$ |
| 52 | 2,4-F$_2$—C$_6$H$_3$ |
| 53 | 3,5-Cl$_2$—C$_6$H$_3$ |
| 54 | 3,4-Cl$_2$—C$_6$H$_3$ |
| 55 | 4-C(CH$_3$)$_3$—C$_6$H$_4$ |
| 56 | 3-Cl—C$_6$H$_4$ |
| 57 | 3-F—C$_6$H$_4$ |
| 58 | 2-F—C$_6$H$_4$ |
| 59 | 2-CF$_3$—C$_6$H$_4$ |
| 60 | 2-CH$_3$O—C$_6$H$_4$ |
| 61 | 3-CH$_3$O—C$_6$H$_4$ |
| 62 | 3-Cl-4-F—C$_6$H$_3$ |
| 63 | 3-NO$_2$—C$_6$H$_4$ |
| 64 | 2-CH$_3$—C$_6$H$_4$ |
| 65 | 3-CH$_3$—C$_6$H$_4$ |
| 66 | 4-CH$_3$—C$_6$H$_4$ |
| 67 | 2-phenyl—C$_6$H$_4$ |
| 68 | 3-phenyl—C$_6$H$_4$ |
| 69 | 2-F-4-Cl—C$_6$H$_3$ |
| 70 | 2,4,6-Cl$_3$—C$_6$H$_2$ |
| 71 | 2,3,4-Cl$_3$—C$_6$H$_2$ |
| 72 | 2,6-F$_2$—C$_6$H$_3$ |
| 73 | CH$_2$F |
| 74 | CHF$_2$ |
| 75 | CF$_3$ |
| 76 | CH$_2$CHF$_2$ |
| 77 | CH$_2$Cl |
| 78 | CHCl$_2$ |
| 79 | CCl$_3$ |
| 80 | CH$_2$CHCl$_2$ |
| 81 | CH$_2$CCl$_3$ |

Further examples of suitable radicals A3 are the radicals for the formulae A3.ba, A3.bb, A3.bc, A3.bd, A3.be, A3.bf, A3.bg, A3.bh, A3.bi, A3.bk, A3.bl, A3.bm, A3.bn and A3.bo, wherein R is as defined in one row of table A3 (radicals A3.ba1-A3.ba81 to A3.bo1-A3.bo81):

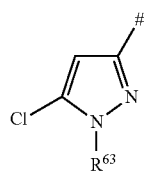
A3.ba

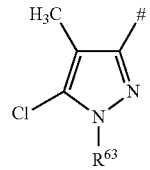
A3.bb

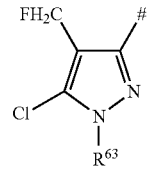
A3.bc

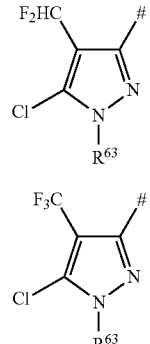
A3.bd

A3.be

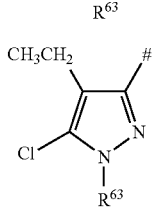
A3.bf

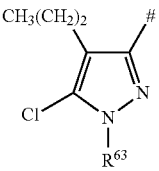
A3.bg

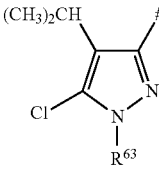
A3.bh

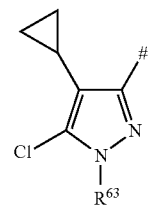
A3.bi

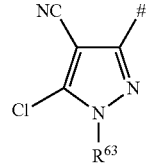
A3.bk

-continued

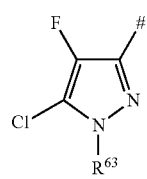
A3.bl

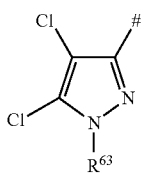
A3.bm

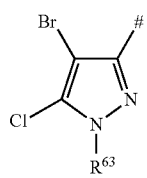
A3.bn

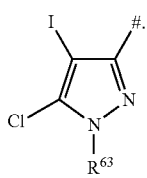
A3.bo

Further examples of suitable radicals A3 are the radicals for the formulae A3.ca, A3.cb, A3.cc, A3.cd, A3.ce, A3.cf, A3.cg, A3.ch, A3.ci, A3.ck, A3.ci, A3.cm, A3.cn and A3.co, wherein $R^{53}$ is as defined in one row of table A3 (radicals A3.ca1-A3.ca81 to A3.co1-A3.co81):

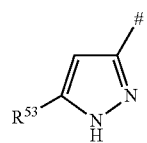
A3.ca

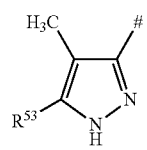
A3.cb

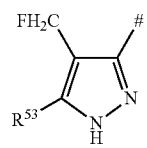
A3.cc

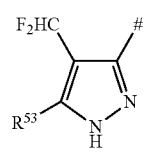
A3.cd

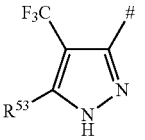
A3.ce

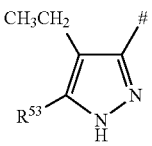
A3.cf

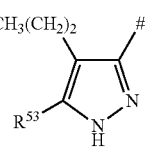
A3.cg

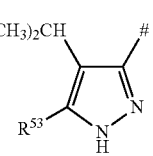
A3.ch

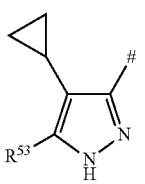
A3.ci

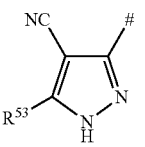
A3.ck

A3.cl

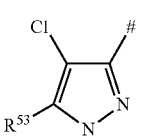
A3.cm

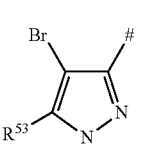
A3.cn

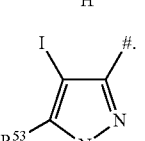
A3.co

Further examples of suitable radicals A3 are the radicals for the formulae A3.da, A3.db, A3.dc, A3.dd, A3.de, A3.df, A3.dg, A3.dh, A3.di, A3.dk, A3.dl, A3.dm, A3.dn and A3.do, wherein $R^{53}$ is as defined in one row of table A3 (radicals A3.da1-A3.da81 to A3.do1-A3.do81):
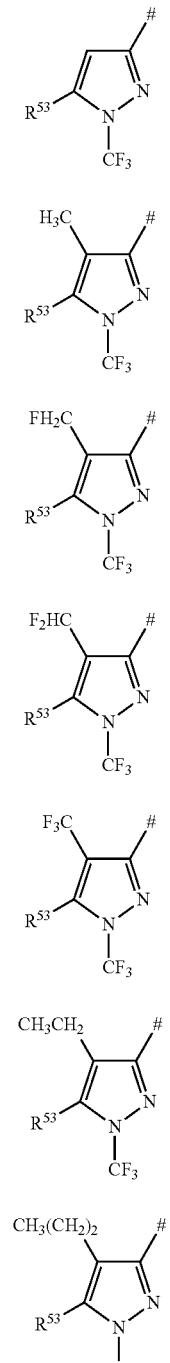
A3.da
A3.db
A3.dc
A3.dd
A3.de
A3.df
A3.dg
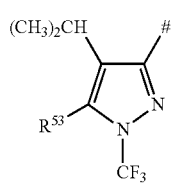
A3.dh
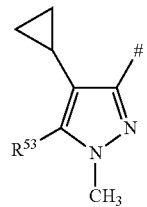
A3.di
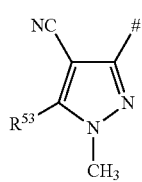
A3.dk
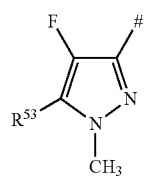
A3.dl
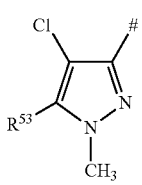
A3.dm
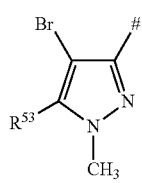
A3.dn
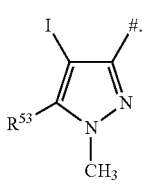
A3.do
Further examples of suitable radicals A3 are the radicals for the formulae A3.ea, A3.eb, A3.ec, A3.ed, A3.ee, A3.ef, A3.eg, A3.eh, A3.ei, A3.ek, A3.el, A3.em, A3.en and A3.eo, wherein $R^{53}$ is as defined in one row of table A3 (radicals A3.ea1-A3.ea81 to A3.eo1-A3.eo81):
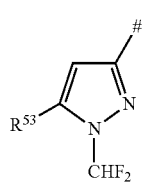
A3.ea A3.eb 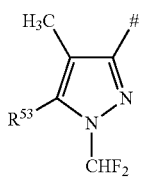
A3.ec 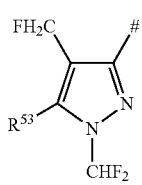
A3.ed 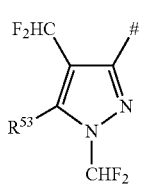
A3.ee 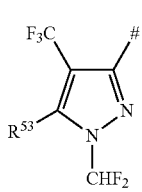
A3.ef 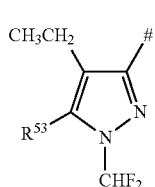
A3.eg 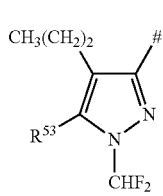
A3.eh 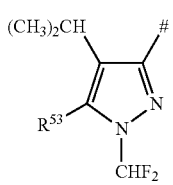
A3.ei 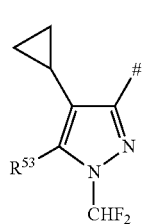
A3.ek 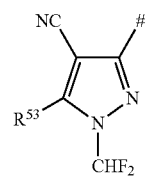
A3.el 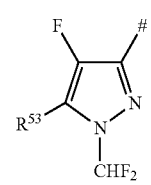
A3.em 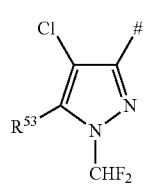
A3.en 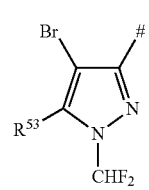
A3.eo 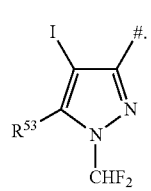
Further examples of suitable radicals A3 are the radicals for the formulae A3.fa, A3.fb, A3.fc, A3.fd, A3.fe, A3.ff, A3.fg, A3.fh, A3.fi, A3.fk, A3.fl, A3.fm, A3.fn and A3.fo, wherein $R^{53}$ is as defined in one row of table A3 (radicals A3.fa1-A3.fa81 to A3.fo1-A3.fo81):
A3.fa 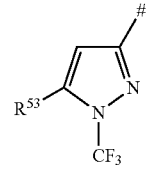
A3.fb 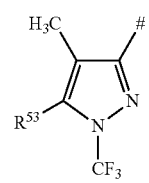

-continued

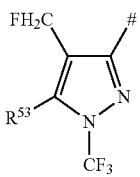 A3.fc

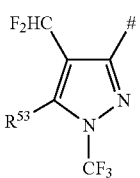 A3.fd

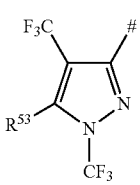 A3.fe

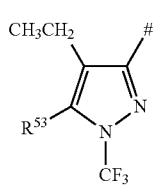 A3.ff

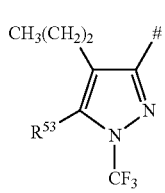 A3.fg

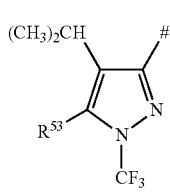 A3.fh

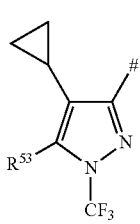 A3.fi

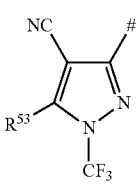 A3.fk

-continued

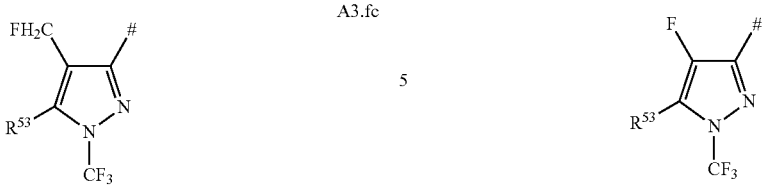 A3.fl

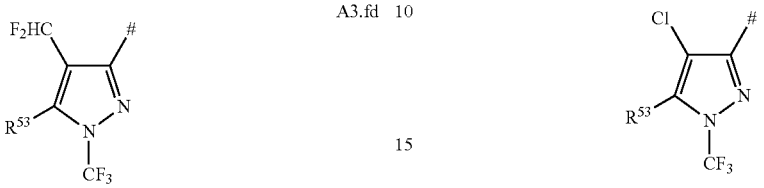 A3.fm

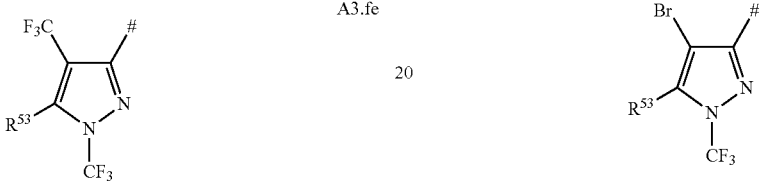 A3.fn

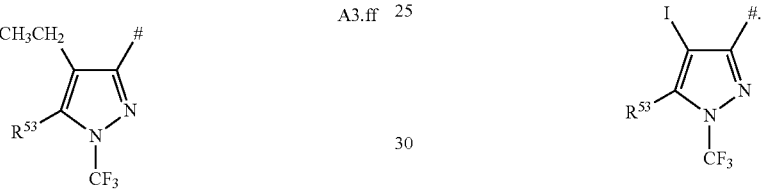 A3.fo

Apart from that, $X^3$ is preferably a lone pair. compounds of the formulae I or II, wherein X is O are also referred to as N-oxides of compounds I or II.

Apart from that, the variables Y, $R^a$, $R^b$, $R^c$, $R^d$, $R^e$, $R^f$, $R^g$, $R^h$, $R^x$ and $R^y$, independently of each other, preferably have one of the following meanings:

Y is O;

$R^a$, $R^b$, $R^c$ are independently of each other selected from hydrogen, $C_1$-$C_4$-alkyl and $C_1$-$C_4$-haloalkyl;

$R^d$ is selected from $C_1$-$C_4$-alkyl and $C_1$-$C_4$-haloalkyl;

$R^e$, $R^f$ are independently of each other selected from hydrogen, $C_1$-$C_4$-alkyl, or $R^e$ and $R^f$ together with the nitrogen atom to which they are bound form a 5- or 6-membered, saturated heterocycle, which may carry a further heteroatom being selected from O, S and N as a ring member atom, e.g. pyrrolidin-1-yl, piperidin-1-yl, morpholin-4-yl, piperazin-1-yl or 4-methylpiperazin-1-yl;

$R^g$, $R^h$, $R^i$ are independently of each other selected from hydrogen and $C_1$-$C_4$-alkyl;

$R^x$ is selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl;

$R^y$ is selected from $C_1$-$C_4$-alkoxy, $C_3$-$C_6$-cycloalkyl and phenyl.

A very preferred embodiment of the invention relates to compounds of the formula I and to their salts, wherein $X^1$ is O and $X^3$ is a lone pair. These compounds are hereinafter also referred to as compounds Ia.

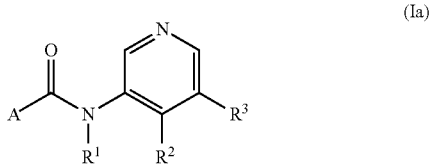

(Ia)

In formula Ia, the variables A, $R^1$, $R^2$ and $R^3$ are as defined herein. Amongst the compounds of the formula Ia, preference is given to those compounds, wherein A is a radical A1, e.g. a radical, selected from the pyrazole radicals A1.a1 to A1.z81. Amongst the compounds of the formula Ia, preference is given to those compounds, wherein at least one of the radicals $R^1$, $R^2$ and $R^3$, preferably at least two of the radicals $R^1$, $R^2$ and $R^3$, and more preferably all of the radicals $R^1$, $R^2$ and $R^3$ have one of the preferred meanings.

A particular preferred embodiment relates to compounds of the formula Ia and to their salts, wherein A is a radical A1, as defined herein, in particular a radical A1, wherein $R^{41}$, $R^{51}$ and $R^{61}$ have the preferred meanings, in particular a pyrazole radical of the formulae A1.a to A1.z, e.g. a radical selected from the pyrazole radicals A1.a1 to A1.z81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment are the compounds given in the following tables 1 to 75.

Table 1: Compounds of the formula Ia and their salts, wherein $R^1$, $R^2$ and $R^3$ are hydrogen and wherein A is selected from the radicals A1.a1 to A1.a81.

Table 2: Compounds of the formula Ia and their salts, wherein $R^1$ is methyl, $R^2$ and $R^3$ are hydrogen and wherein A is selected from the radicals A1.a1 to A1.a81.

Table 3: Compounds of the formula Ia and their salts, wherein $R^1$ is ethyl, $R^2$ and $R^3$ are hydrogen and wherein A is selected from the radicals A1.a1 to A1.a81.

Table 4: Compounds of the formula Ia and their salts, wherein $R^1$, $R^2$ and $R^3$ are hydrogen and wherein A is selected from the radicals A1.b1 to A1.b81.

Table 5: Compounds of the formula Ia and their salts, wherein $R^1$ is methyl, $R^2$ and $R^3$ are hydrogen and wherein A is selected from the radicals A1.b1 to A1.b81.

Table 6: Compounds of the formula Ia and their salts, wherein $R^1$ is ethyl, $R^2$ and $R^3$ are hydrogen and wherein A is selected from the radicals A1.b1 to A1.b81.

Table 7: Compounds of the formula Ia and their salts, wherein $R^1$, $R^2$ and $R^3$ are hydrogen and wherein A is selected from the radicals A1.c1 to A1.c81.

Table 8: Compounds of the formula Ia and their salts, wherein $R^1$ is methyl, $R^2$ and $R^3$ are hydrogen and wherein A is selected from the radicals A1.c1 to A1.c81.

Table 9: Compounds of the formula Ia and their salts, wherein $R^1$ is ethyl, $R^2$ and $R^3$ are hydrogen and wherein A is selected from the radicals A1.c1 to A1.c81.

Table 10: Compounds of the formula Ia and their salts, wherein $R^1$, $R^2$ and $R^3$ are hydrogen and wherein A is selected from the radicals A1.d1 to A1.d81.

Table 11: Compounds of the formula Ia and their salts, wherein $R^1$ is methyl, $R^2$ and $R^3$ are hydrogen and wherein A is selected from the radicals A1.d1 to A1.d81.

Table 12: Compounds of the formula Ia and their salts, wherein $R^1$ is ethyl, $R^2$ and $R^3$ are hydrogen and wherein A is selected from the radicals A1.d1 to A1.d81.

Table 13: Compounds of the formula Ia and their salts, wherein $R^1$, $R^2$ and $R^3$ are hydrogen and wherein A is selected from the radicals A1.e1 to A1.e81.

Table 14: Compounds of the formula Ia and their salts, wherein $R^1$ is methyl, $R^2$ and $R^3$ are hydrogen and wherein A is selected from the radicals A1.e1 to A1.e81.

Table 15: Compounds of the formula Ia and their salts, wherein $R^1$ is ethyl, $R^2$ and $R^3$ are hydrogen and wherein A is selected from the radicals A1.e1 to A1.e81.

Table 16: Compounds of the formula Ia and their salts, wherein $R^1$, $R^2$ and $R^3$ are hydrogen and wherein A is selected from the radicals A1.f1 to A1.f81.

Table 17: Compounds of the formula Ia and their salts, wherein $R^1$ is methyl, $R^2$ and $R^3$ are hydrogen and wherein A is selected from the radicals A1.f1 to A1.f81.

Table 18: Compounds of the formula Ia and their salts, wherein $R^1$ is ethyl, $R^2$ and $R^3$ are hydrogen and wherein A is selected from the radicals A1.f1 to A1.f81.

Table 19: Compounds of the formula Ia and their salts, wherein $R^1$, $R^2$ and $R^3$ are hydrogen and wherein A is selected from the radicals A1.g1 to A1.g81.

Table 20: Compounds of the formula Ia and their salts, wherein $R^1$ is methyl, $R^2$ and $R^3$ are hydrogen and wherein A is selected from the radicals A1.g1 to A1.g81.

Table 21: Compounds of the formula Ia and their salts, wherein $R^1$ is ethyl, $R^2$ and $R^3$ are hydrogen and wherein A is selected from the radicals A1.g1 to A1.g81.

Table 22: Compounds of the formula Ia and their salts, wherein $R^1$, $R^2$ and $R^3$ are hydrogen and wherein A is selected from the radicals A1.h1 to A1.h81.

Table 23: Compounds of the formula Ia and their salts, wherein $R^1$ is methyl, $R^2$ and $R^3$ are hydrogen and wherein A is selected from the radicals A1.h1 to A1.h81.

Table 24: Compounds of the formula Ia and their salts, wherein $R^1$ is ethyl, $R^2$ and $R^3$ are hydrogen and wherein A is selected from the radicals A1.h1 to A1.h81.

Table 25: Compounds of the formula Ia and their salts, wherein $R^1$, $R^2$ and $R^3$ are hydrogen and wherein A is selected from the radicals A1.i1 to A1.i81.

Table 26: Compounds of the formula Ia and their salts, wherein $R^1$ is methyl, $R^2$ and $R^3$ are hydrogen and wherein A is selected from the radicals A1.i1 to A1.i81.

Table 27: Compounds of the formula Ia and their salts, wherein $R^1$ is ethyl, $R^2$ and $R^3$ are hydrogen and wherein A is selected from the radicals A1.i1 to A1.i81.

Table 28: Compounds of the formula Ia and their salts, wherein $R^1$, $R^2$ and $R^3$ are hydrogen and wherein A is selected from the radicals A1.k1 to A1.k81.

Table 29: Compounds of the formula Ia and their salts, wherein $R^1$ is methyl, $R^2$ and $R^3$ are hydrogen and wherein A is selected from the radicals A1.k1 to A1.k81.

Table 30: Compounds of the formula Ia and their salts, wherein $R^1$ is ethyl, $R^2$ and $R^3$ are hydrogen and wherein A is selected from the radicals A1.k1 to A1.k81.

Table 31: Compounds of the formula Ia and their salts, wherein $R^1$, $R^2$ and $R^3$ are hydrogen and wherein A is selected from the radicals A1.l1 to A1.l81.

Table 32: Compounds of the formula Ia and their salts, wherein $R^1$ is methyl, $R^2$ and $R^3$ are hydrogen and wherein A is selected from the radicals A1.l1 to A1.l81.

Table 33: Compounds of the formula Ia and their salts, wherein $R^1$ is ethyl, $R^2$ and $R^3$ are hydrogen and wherein A is selected from the radicals A1.l1 to A1.l81.

Table 34: Compounds of the formula Ia and their salts, wherein $R^1$, $R^2$ and $R^3$ are hydrogen and wherein A is selected from the radicals A1.m1 to A1.m81.

Table 35: Compounds of the formula Ia and their salts, wherein $R^1$ is methyl, $R^2$ and $R^3$ are hydrogen and wherein A is selected from the radicals A1.m1 to A1.m81.

Table 36: Compounds of the formula Ia and their salts, wherein $R^1$ is ethyl, $R^2$ and $R^3$ are hydrogen and wherein A is selected from the radicals A1.m1 to A1.m81.

Table 37: Compounds of the formula Ia and their salts, wherein $R^1$, $R^2$ and $R^3$ are hydrogen and wherein A is selected from the radicals A1.n1 to A1.n81.

Table 38: Compounds of the formula Ia and their salts, wherein $R^1$ is methyl, $R^2$ and $R^3$ are hydrogen and wherein A is selected from the radicals A1.n1 to A1.n81.

Table 39: Compounds of the formula Ia and their salts, wherein $R^1$ is ethyl, $R^2$ and $R^3$ are hydrogen and wherein A is selected from the radicals A1.n1 to A1.n81.

Table 40: Compounds of the formula Ia and their salts, wherein $R^1$, $R^2$ and $R^3$ are hydrogen and wherein A is selected from the radicals A1.o1 to A1.o81.

Table 41: Compounds of the formula Ia and their salts, wherein $R^1$ is methyl, $R^2$ and $R^3$ are hydrogen and wherein A is selected from the radicals A1.o1 to A1.o81.

Table 42: Compounds of the formula Ia and their salts, wherein $R^1$ is ethyl, $R^2$ and $R^3$ are hydrogen and wherein A is selected from the radicals A1.o1 to A1.o81.

Table 43: Compounds of the formula Ia and their salts, wherein $R^1$, $R^2$ and $R^3$ are hydrogen and wherein A is selected from the radicals A1.p1 to A1.p81.

Table 44: Compounds of the formula Ia and their salts, wherein $R^1$ is methyl, $R^2$ and $R^3$ are hydrogen and wherein A is selected from the radicals A1.p1 to A1.p81.

Table 45: Compounds of the formula Ia and their salts, wherein $R^1$ is ethyl, $R^2$ and $R^3$ are hydrogen and wherein A is selected from the radicals A1.p1 to A1.p81.

Table 46: Compounds of the formula Ia and their salts, wherein $R^1$, $R^2$ and $R^3$ are hydrogen and wherein A is selected from the radicals A1.q1 to A1.q81.

Table 47: Compounds of the formula Ia and their salts, wherein $R^1$ is methyl, $R^2$ and $R^3$ are hydrogen and wherein A is selected from the radicals A1.q1 to A1.q81.

Table 48: Compounds of the formula Ia and their salts, wherein $R^1$ is ethyl, $R^2$ and $R^3$ are hydrogen and wherein A is selected from the radicals A1.q1 to A1.q81.

Table 49: Compounds of the formula Ia and their salts, wherein $R^1$, $R^2$ and $R^3$ are hydrogen and wherein A is selected from the radicals A1.r1 to A1.r81.

Table 50: Compounds of the formula Ia and their salts, wherein $R^1$ is methyl, $R^2$ and $R^3$ are hydrogen and wherein A is selected from the radicals A1.r1 to A1.r81.

Table 51: Compounds of the formula Ia and their salts, wherein $R^1$ is ethyl, $R^2$ and $R^3$ are hydrogen and wherein A is selected from the radicals A1.r1 to A1.r81.

Table 52: Compounds of the formula Ia and their salts, wherein $R^1$, $R^2$ and $R^3$ are hydrogen and wherein A is selected from the radicals A1.s1 to A1.s81.

Table 53: Compounds of the formula Ia and their salts, wherein $R^1$ is methyl, $R^2$ and $R^3$ are hydrogen and wherein A is selected from the radicals A1.s1 to A1.s81.

Table 54: Compounds of the formula Ia and their salts, wherein $R^1$ is ethyl, $R^2$ and $R^3$ are hydrogen and wherein A is selected from the radicals A1.s1 to A1.s81.

Table 55: Compounds of the formula Ia and their salts, wherein $R^1$, $R^2$ and $R^3$ are hydrogen and wherein A is selected from the radicals A1.t1 to A1.t81.

Table 56: Compounds of the formula Ia and their salts, wherein $R^1$ is methyl, $R^2$ and $R^3$ are hydrogen and wherein A is selected from the radicals A1.t1 to A1.t81.

Table 57: Compounds of the formula Ia and their salts, wherein $R^1$ is ethyl, $R^2$ and $R^3$ are hydrogen and wherein A is selected from the radicals A1.t1 to A1.t81.

Table 58: Compounds of the formula Ia and their salts, wherein $R^1$, $R^2$ and $R^3$ are hydrogen and wherein A is selected from the radicals A1.u1 to A1.u81.

Table 59: Compounds of the formula Ia and their salts, wherein $R^1$ is methyl, $R^2$ and $R^3$ are hydrogen and wherein A is selected from the radicals A1.u1 to A1.u81.

Table 60: Compounds of the formula Ia and their salts, wherein $R^1$ is ethyl, $R^2$ and $R^3$ are hydrogen and wherein A is selected from the radicals A1.u1 to A1.u81.

Table 61: Compounds of the formula Ia and their salts, wherein $R^1$, $R^2$ and $R^3$ are hydrogen and wherein A is selected from the radicals A1.v1 to A1.v81.

Table 62: Compounds of the formula Ia and their salts, wherein $R^1$ is methyl, $R^2$ and $R^3$ are hydrogen and wherein A is selected from the radicals A1.v1 to A1.v81.

Table 63: Compounds of the formula Ia and their salts, wherein $R^1$ is ethyl, $R^2$ and $R^3$ are hydrogen and wherein A is selected from the radicals A1.v1 to A1.v81.

Table 64: Compounds of the formula Ia and their salts, wherein $R^1$, $R^2$ and $R^3$ are hydrogen and wherein A is selected from the radicals A1.w1 to A1.w81.

Table 65: Compounds of the formula Ia and their salts, wherein $R^1$ is methyl, $R^2$ and $R^3$ are hydrogen and wherein A is selected from the radicals A1.w1 to A1.w81.

Table 66: Compounds of the formula Ia and their salts, wherein $R^1$ is ethyl, $R^2$ and $R^3$ are hydrogen and wherein A is selected from the radicals A1.w1 to A1.w81.

Table 67: Compounds of the formula Ia and their salts, wherein $R^1$, $R^2$ and $R^3$ are hydrogen and wherein A is selected from the radicals A1.x1 to A1.x81.

Table 68: Compounds of the formula Ia and their salts, wherein $R^1$ is methyl, $R^2$ and $R^3$ are hydrogen and wherein A is selected from the radicals A1.x1 to A1.x81.

Table 69: Compounds of the formula Ia and their salts, wherein $R^1$ is ethyl, $R^2$ and $R^3$ are hydrogen and wherein A is selected from the radicals A1.x1 to A1.x81.

Table 70: Compounds of the formula Ia and their salts, wherein $R^1$, $R^2$ and $R^3$ are hydrogen and wherein A is selected from the radicals A1.y1 to A1.y81.

Table 71: Compounds of the formula Ia and their salts, wherein $R^1$ is methyl, $R^2$ and $R^3$ are hydrogen and wherein A is selected from the radicals A1.y1 to A1.y81.

Table 72: Compounds of the formula Ia and their salts, wherein $R^1$ is ethyl, $R^2$ and $R^3$ are hydrogen and wherein A is selected from the radicals A1.y1 to A1.y81.

Table 73: Compounds of the formula Ia and their salts, wherein $R^1$, $R^2$ and $R^3$ are hydrogen and wherein A is selected from the radicals A1.z1 to A1.z81.

Table 74: Compounds of the formula Ia and their salts, wherein $R^1$ is methyl, $R^2$ and $R^3$ are hydrogen and wherein A is selected from the radicals A1.z1 to A1.z81.

Table 75: Compounds of the formula Ia and their salts, wherein $R^1$ is ethyl, $R^2$ and $R^3$ are hydrogen and wherein A is selected from the radicals A1.z1 to A1.z81.

Another particular preferred embodiment relates to compounds of the formula Ia and to their salts, wherein A is a radical A2, as defined herein, in particular a radical A2, wherein $R^{42}$, $R^{52}$ and $R^{62}$ have the preferred meanings, in particular a pyrazole radical of the formulae A2.aa to A2.do, e.g. a radical selected from the pyrazole radicals A2.aa1-A2.aa81 to A2.do1 to A2.do81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment are the compounds given in the following tables 76 to 231.

Table 76: Compounds of the formula Ia and their salts, wherein $R^1$, $R^2$ and $R^3$ are hydrogen and wherein A is selected from the radicals A2.aa1 to A2.aa81.

Table 77: Compounds of the formula Ia and their salts, wherein $R^1$ is methyl, $R^2$ and $R^3$ are hydrogen and wherein A is selected from the radicals A2.aa1 to A2.aa81.

Table 78: Compounds of the formula Ia and their salts, wherein $R^1$ is ethyl, $R^2$ and $R^3$ are hydrogen and wherein A is selected from the radicals A2.aa1 to A2.aa81.

Table 79: Compounds of the formula Ia and their salts, wherein $R^1$, $R^2$ and $R^3$ are hydrogen and wherein A is selected from the radicals A2.ab1 to A2.ab81.

Table 80: Compounds of the formula Ia and their salts, wherein $R^1$ is methyl, $R^2$ and $R^3$ are hydrogen and wherein A is selected from the radicals A2.ab1 to A2.ab81.

Table 81: Compounds of the formula Ia and their salts, wherein $R^1$ is ethyl, $R^2$ and $R^3$ are hydrogen and wherein A is selected from the radicals A2.ab1 to A2.ab81.

Table 82: Compounds of the formula Ia and their salts, wherein $R^1$, $R^2$ and $R^3$ are hydrogen and wherein A is selected from the radicals A2.ac1 to A2.ac81.

Table 83: Compounds of the formula Ia and their salts, wherein $R^1$ is methyl, $R^2$ and $R^3$ are hydrogen and wherein A is selected from the radicals A2.ac1 to A2.ac81.

Table 84: Compounds of the formula Ia and their salts, wherein $R^1$ is ethyl, $R^2$ and $R^3$ are hydrogen and wherein A is selected from the radicals A2.ac1 to A2.ac81.

Table 85: Compounds of the formula Ia and their salts, wherein $R^1$, $R^2$ and $R^3$ are hydrogen and wherein A is selected from the radicals A2.ad1 to A2.ad81.

Table 86: Compounds of the formula Ia and their salts, wherein $R^1$ is methyl, $R^2$ and $R^3$ are hydrogen and wherein A is selected from the radicals A2.ad1 to A2.ad81.

Table 87: Compounds of the formula Ia and their salts, wherein $R^1$ is ethyl, $R^2$ and $R^3$ are hydrogen and wherein A is selected from the radicals A2.ad1 to A2.ad81.

Table 88: Compounds of the formula Ia and their salts, wherein $R^1$, $R^2$ and $R^3$ are hydrogen and wherein A is selected from the radicals A2.ae1 to A2.ae81.

Table 89: Compounds of the formula Ia and their salts, wherein $R^1$ is methyl, $R^2$ and $R^3$ are hydrogen and wherein A is selected from the radicals A2.ae1 to A2.ae81.

Table 90: Compounds of the formula Ia and their salts, wherein $R^1$ is ethyl, $R^2$ and $R^3$ are hydrogen and wherein A is selected from the radicals A2.ae1 to A2.ae81.

Table 91: Compounds of the formula Ia and their salts, wherein $R^1$, $R^2$ and $R^3$ are hydrogen and wherein A is selected from the radicals A2.af1 to A2.af81.

Table 92: Compounds of the formula Ia and their salts, wherein $R^1$ is methyl, $R^2$ and $R^3$ are hydrogen and wherein A is selected from the radicals A2.af1 to A2.af81.

Table 93: Compounds of the formula Ia and their salts, wherein $R^1$ is ethyl, $R^2$ and $R^3$ are hydrogen and wherein A is selected from the radicals A2.af1 to A2.af81.

Table 94: Compounds of the formula Ia and their salts, wherein $R^1$, $R^2$ and $R^3$ are hydrogen and wherein A is selected from the radicals A2.ag1 to A2.ag81.

Table 95: Compounds of the formula Ia and their salts, wherein $R^1$ is methyl, $R^2$ and $R^3$ are hydrogen and wherein A is selected from the radicals A2.ag1 to A2.ag81.

Table 96: Compounds of the formula Ia and their salts, wherein $R^1$ is ethyl, $R^2$ and $R^3$ are hydrogen and wherein A is selected from the radicals A2.ah1 to A2.ah81.

Table 97: Compounds of the formula Ia and their salts, wherein $R^1$, $R^2$ and $R^3$ are hydrogen and wherein A is selected from the radicals A2.ai1 to A2.ai81.

Table 98: Compounds of the formula Ia and their salts, wherein $R^1$ is methyl, $R^2$ and $R^3$ are hydrogen and wherein A is selected from the radicals A2.ai1 to A2.ai81.

Table 99: Compounds of the formula Ia and their salts, wherein $R^1$ is ethyl, $R^2$ and $R^3$ are hydrogen and wherein A is selected from the radicals A2.ai1 to A2.ai81.

Table 100: Compounds of the formula Ia and their salts, wherein $R^1$, $R^2$ and $R^3$ are hydrogen and wherein A is selected from the radicals A2.ak1 to A2.ak81.

Table 101: Compounds of the formula Ia and their salts, wherein $R^1$ is methyl, $R^2$ and $R^3$ are hydrogen and wherein A is selected from the radicals A2.ak1 to A2.ak81.

Table 102: Compounds of the formula Ia and their salts, wherein $R^1$ is ethyl, $R^2$ and $R^3$ are hydrogen and wherein A is selected from the radicals A2.ak1 to A2.ak81.

Table 103: Compounds of the formula Ia and their salts, wherein $R^1$, $R^2$ and $R^3$ are hydrogen and wherein A is selected from the radicals A2.al1 to A2.al81.

Table 104: Compounds of the formula Ia and their salts, wherein $R^1$ is methyl, $R^2$ and $R^3$ are hydrogen and wherein A is selected from the radicals A2.al1 to A2.al81.

Table 105: Compounds of the formula Ia and their salts, wherein $R^1$ is ethyl, $R^2$ and $R^3$ are hydrogen and wherein A is selected from the radicals A2.al1 to A2.al81.

Table 106: Compounds of the formula Ia and their salts, wherein $R^1$, $R^2$ and $R^3$ are hydrogen and wherein A is selected from the radicals A2.am1 to A2.am81.

Table 107: Compounds of the formula Ia and their salts, wherein $R^1$ is methyl, $R^2$ and $R^3$ are hydrogen and wherein A is selected from the radicals A2.am1 to A2.am81.

Table 108: Compounds of the formula Ia and their salts, wherein $R^1$ is ethyl, $R^2$ and $R^3$ are hydrogen and wherein A is selected from the radicals A2.am1 to A2.am81.

Table 109: Compounds of the formula Ia and their salts, wherein $R^1$, $R^2$ and $R^3$ are hydrogen and wherein A is selected from the radicals A2.an1 to A2.an81.

Table 110: Compounds of the formula Ia and their salts, wherein $R^1$ is methyl, $R^2$ and $R^3$ are hydrogen and wherein A is selected from the radicals A2.an1 to A2.an81.

Table 111: Compounds of the formula Ia and their salts, wherein $R^1$ is ethyl, $R^2$ and $R^3$ are hydrogen and wherein A is selected from the radicals A2.an1 to A2.an81.

Table 112: Compounds of the formula Ia and their salts, wherein $R^1$, $R^2$ and $R^3$ are hydrogen and wherein A is selected from the radicals A2.ao1 to A2.ao81.

Table 113: Compounds of the formula Ia and their salts, wherein $R^1$ is methyl, $R^2$ and $R^3$ are hydrogen and wherein A is selected from the radicals A2.ao1 to A2.ao81.

Table 114: Compounds of the formula Ia and their salts, wherein $R^1$ is ethyl, $R^2$ and $R^3$ are hydrogen and wherein A is selected from the radicals A2.ao1 to A2.ao81.

Table 115: Compounds of the formula Ia and their salts, wherein $R^1$, $R^2$ and $R^3$ are hydrogen and wherein A is selected from the radicals A2.ba1 to A2.ba81.

Table 116: Compounds of the formula Ia and their salts, wherein $R^1$ is methyl, $R^2$ and $R^3$ are hydrogen and wherein A is selected from the radicals A2.ba1 to A2.ba81.

Table 117: Compounds of the formula Ia and their salts, wherein $R^1$ is ethyl, $R^2$ and $R^3$ are hydrogen and wherein A is selected from the radicals A2.ba1 to A2.ba81.

Table 118: Compounds of the formula Ia and their salts, wherein $R^1$, $R^2$ and $R^3$ are hydrogen and wherein A is selected from the radicals A2.bb1 to A2.bb81.

Table 119: Compounds of the formula Ia and their salts, wherein $R^1$ is methyl, $R^2$ and $R^3$ are hydrogen and wherein A is selected from the radicals A2.bb1 to A2.bb81.

Table 120: Compounds of the formula Ia and their salts, wherein $R^1$ is ethyl, $R^2$ and $R^3$ are hydrogen and wherein A is selected from the radicals A2.bb1 to A2.bb81.

Table 121: Compounds of the formula Ia and their salts, wherein $R^1$, $R^2$ and $R^3$ are hydrogen and wherein A is selected from the radicals A2.bc1 to A2.bc81.

Table 122: Compounds of the formula Ia and their salts, wherein $R^1$ is methyl, $R^2$ and $R^3$ are hydrogen and wherein A is selected from the radicals A2.bc1 to A2.bc81.

Table 123: Compounds of the formula Ia and their salts, wherein $R^1$ is ethyl, $R^2$ and $R^3$ are hydrogen and wherein A is selected from the radicals A2.bc1 to A2.bc81.

Table 124: Compounds of the formula Ia and their salts, wherein $R^1$, $R^2$ and $R^3$ are hydrogen and wherein A is selected from the radicals A2.bd1 to A2.bd81.

Table 125: Compounds of the formula Ia and their salts, wherein $R^1$ is methyl, $R^2$ and $R^3$ are hydrogen and wherein A is selected from the radicals A2.bd1 to A2.bd81.

Table 126: Compounds of the formula Ia and their salts, wherein $R^1$ is ethyl, $R^2$ and $R^3$ are hydrogen and wherein A is selected from the radicals A2.bd1 to A2.bd81.

Table 127: Compounds of the formula Ia and their salts, wherein $R^1$, $R^2$ and $R^3$ are hydrogen and wherein A is selected from the radicals A2.be1 to A2.be81.

Table 128: Compounds of the formula Ia and their salts, wherein $R^1$ is methyl, $R^2$ and $R^3$ are hydrogen and wherein A is selected from the radicals A2.be1 to A2.be81.

Table 129: Compounds of the formula Ia and their salts, wherein $R^1$ is ethyl, $R^2$ and $R^3$ are hydrogen and wherein A is selected from the radicals A2.be1 to A2.be81.

Table 130: Compounds of the formula Ia and their salts, wherein $R^1$, $R^2$ and $R^3$ are hydrogen and wherein A is selected from the radicals A2.bf1 to A2.bf81.

Table 131: Compounds of the formula Ia and their salts, wherein $R^1$ is methyl, $R^2$ and $R^3$ are hydrogen and wherein A is selected from the radicals A2.bf1 to A2.bf81.

Table 132: Compounds of the formula Ia and their salts, wherein $R^1$ is ethyl, $R^2$ and $R^3$ are hydrogen and wherein A is selected from the radicals A2.bf1 to A2.bf81.

Table 133: Compounds of the formula Ia and their salts, wherein $R^1$, $R^2$ and $R^3$ are hydrogen and wherein A is selected from the radicals A2.bg1 to A2.bg81.

Table 134: Compounds of the formula Ia and their salts, wherein $R^1$ is methyl, $R^2$ and $R^3$ are hydrogen and wherein A is selected from the radicals A2.bg1 to A2.bg81.

Table 135: Compounds of the formula Ia and their salts, wherein $R^1$ is ethyl, $R^2$ and $R^3$ are hydrogen and wherein A is selected from the radicals A2.bh1 to A2.bh81.

Table 136: Compounds of the formula Ia and their salts, wherein $R^1$, $R^2$ and $R^3$ are hydrogen and wherein A is selected from the radicals A2.bi1 to A2.bi81.

Table 137: Compounds of the formula Ia and their salts, wherein $R^1$ is methyl, $R^2$ and $R^3$ are hydrogen and wherein A is selected from the radicals A2.bi1 to A2.bi81.

Table 138: Compounds of the formula Ia and their salts, wherein $R^1$ is ethyl, $R^2$ and $R^3$ are hydrogen and wherein A is selected from the radicals A2.bi1 to A2.bi81.

Table 139: Compounds of the formula Ia and their salts, wherein $R^1$, $R^2$ and $R^3$ are hydrogen and wherein A is selected from the radicals A2.bk1 to A2.bk81.

Table 140: Compounds of the formula Ia and their salts, wherein $R^1$ is methyl, $R^2$ and $R^3$ are hydrogen and wherein A is selected from the radicals A2.bk1 to A2.bk81.

Table 141: Compounds of the formula Ia and their salts, wherein $R^1$ is ethyl, $R^2$ and $R^3$ are hydrogen and wherein A is selected from the radicals A2.bk1 to A2.bk81.

Table 142: Compounds of the formula Ia and their salts, wherein $R^1$, $R^2$ and $R^3$ are hydrogen and wherein A is selected from the radicals A2.bl1 to A2.bl81.

Table 143: Compounds of the formula Ia and their salts, wherein $R^1$ is methyl, $R^2$ and $R^3$ are hydrogen and wherein A is selected from the radicals A2.bl1 to A2.bl81.

Table 144: Compounds of the formula Ia and their salts, wherein $R^1$ is ethyl, $R^2$ and $R^3$ are hydrogen and wherein A is selected from the radicals A2.bl1 to A2.bl81.

Table 145: Compounds of the formula Ia and their salts, wherein $R^1$, $R^2$ and $R^3$ are hydrogen and wherein A is selected from the radicals A2.bm1 to A2.bm81.

Table 146: Compounds of the formula Ia and their salts, wherein $R^1$ is methyl, $R^2$ and $R^3$ are hydrogen and wherein A is selected from the radicals A2.bm1 to A2.bm81.

Table 147: Compounds of the formula Ia and their salts, wherein $R^1$ is ethyl, $R^2$ and $R^3$ are hydrogen and wherein A is selected from the radicals A2.bm1 to A2.bm81.

Table 148: Compounds of the formula Ia and their salts, wherein $R^1$, $R^2$ and $R^3$ are hydrogen and wherein A is selected from the radicals A2.bn1 to A2.bn81.

Table 149: Compounds of the formula Ia and their salts, wherein $R^1$ is methyl, $R^2$ and $R^3$ are hydrogen and wherein A is selected from the radicals A2.bn1 to A2.bn81.

Table 150: Compounds of the formula Ia and their salts, wherein $R^1$ is ethyl, $R^2$ and $R^3$ are hydrogen and wherein A is selected from the radicals A2.bn1 to A2.bn81.

Table 151: Compounds of the formula Ia and their salts, wherein $R^1$, $R^2$ and $R^3$ are hydrogen and wherein A is selected from the radicals A2.bo1 to A2.bo81.

Table 152: Compounds of the formula Ia and their salts, wherein $R^1$ is methyl, $R^2$ and $R^3$ are hydrogen and wherein A is selected from the radicals A2.bo1 to A2.bo81.

Table 153: Compounds of the formula Ia and their salts, wherein $R^1$ is ethyl, $R^2$ and $R^3$ are hydrogen and wherein A is selected from the radicals A2.bo1 to A2.bo81.

Table 154: Compounds of the formula Ia and their salts, wherein $R^1$, $R^2$ and $R^3$ are hydrogen and wherein A is selected from the radicals A2.ca1 to A2.ca81.

Table 155: Compounds of the formula Ia and their salts, wherein $R^1$ is methyl, $R^2$ and $R^3$ are hydrogen and wherein A is selected from the radicals A2.ca1 to A2.ca81.

Table 156: Compounds of the formula Ia and their salts, wherein $R^1$ is ethyl, $R^2$ and $R^3$ are hydrogen and wherein A is selected from the radicals A2.ca1 to A2.ca81.

Table 157: Compounds of the formula Ia and their salts, wherein $R^1$, $R^2$ and $R^3$ are hydrogen and wherein A is selected from the radicals A2.cb1 to A2.cb81.

Table 158: Compounds of the formula Ia and their salts, wherein $R^1$ is methyl, $R^2$ and $R^3$ are hydrogen and wherein A is selected from the radicals A2.cb1 to A2.cb81.

Table 159: Compounds of the formula Ia and their salts, wherein $R^1$ is ethyl, $R^2$ and $R^3$ are hydrogen and wherein A is selected from the radicals A2.cb1 to A2.cb81.

Table 160: Compounds of the formula Ia and their salts, wherein $R^1$, $R^2$ and $R^3$ are hydrogen and wherein A is selected from the radicals A2.cc1 to A2.cc81.

Table 161: Compounds of the formula Ia and their salts, wherein $R^1$ is methyl, $R^2$ and $R^3$ are hydrogen and wherein A is selected from the radicals A2.cc1 to A2.cc81.

Table 162: Compounds of the formula Ia and their salts, wherein $R^1$ is ethyl, $R^2$ and $R^3$ are hydrogen and wherein A is selected from the radicals A2.cc1 to A2.cc81.

Table 163: Compounds of the formula Ia and their salts, wherein $R^1$, $R^2$ and $R^3$ are hydrogen and wherein A is selected from the radicals A2.cd1 to A2.cd81.

Table 164: Compounds of the formula Ia and their salts, wherein $R^1$ is methyl, $R^2$ and $R^3$ are hydrogen and wherein A is selected from the radicals A2.cd1 to A2.cd81.

Table 165: Compounds of the formula Ia and their salts, wherein $R^1$ is ethyl, $R^2$ and $R^3$ are hydrogen and wherein A is selected from the radicals A2.cd1 to A2.cd81.

Table 166: Compounds of the formula Ia and their salts, wherein $R^1$, $R^2$ and $R^3$ are hydrogen and wherein A is selected from the radicals A2.ce1 to A2.ce81.

Table 167: Compounds of the formula Ia and their salts, wherein $R^1$ is methyl, $R^2$ and $R^3$ are hydrogen and wherein A is selected from the radicals A2.ce1 to A2.ce81.

Table 168: Compounds of the formula Ia and their salts, wherein $R^1$ is ethyl, $R^2$ and $R^3$ are hydrogen and wherein A is selected from the radicals A2.ce1 to A2.ce81.

Table 169: Compounds of the formula Ia and their salts, wherein $R^1$, $R^2$ and $R^3$ are hydrogen and wherein A is selected from the radicals A2.cf1 to A2.cf81.

Table 170: Compounds of the formula Ia and their salts, wherein $R^1$ is methyl, $R^2$ and $R^3$ are hydrogen and wherein A is selected from the radicals A2.cf1 to A2.cf81.

Table 171: Compounds of the formula Ia and their salts, wherein $R^1$ is ethyl, $R^2$ and $R^3$ are hydrogen and wherein A is selected from the radicals A2.cf1 to A2.cf81.

Table 172: Compounds of the formula Ia and their salts, wherein $R^1$, $R^2$ and $R^3$ are hydrogen and wherein A is selected from the radicals A2.cg1 to A2.cg81.

Table 173: Compounds of the formula Ia and their salts, wherein $R^1$ is methyl, $R^2$ and $R^3$ are hydrogen and wherein A is selected from the radicals A2.cg1 to A2.cg81.

Table 174: Compounds of the formula Ia and their salts, wherein $R^1$ is ethyl, $R^2$ and $R^3$ are hydrogen and wherein A is selected from the radicals A2.ch1 to A2.ch81.

Table 175: Compounds of the formula Ia and their salts, wherein $R^1$, $R^2$ and $R^3$ are hydrogen and wherein A is selected from the radicals A2.ci1 to A2.ci81.

Table 176: Compounds of the formula Ia and their salts, wherein $R^1$ is methyl, $R^2$ and $R^3$ are hydrogen and wherein A is selected from the radicals A2.ci1 to A2.ci81.

Table 177: Compounds of the formula Ia and their salts, wherein $R^1$ is ethyl, $R^2$ and $R^3$ are hydrogen and wherein A is selected from the radicals A2.ci1 to A2.ci81.

Table 178: Compounds of the formula Ia and their salts, wherein $R^1$, $R^2$ and $R^3$ are hydrogen and wherein A is selected from the radicals A2.ck1 to A2.ck81.

Table 179: Compounds of the formula Ia and their salts, wherein $R^1$ is methyl, $R^2$ and $R^3$ are hydrogen and wherein A is selected from the radicals A2.ck1 to A2.ck81.

Table 180: Compounds of the formula Ia and their salts, wherein $R^1$ is ethyl, $R^2$ and $R^3$ are hydrogen and wherein A is selected from the radicals A2.ck1 to A2.ck81.

Table 181: Compounds of the formula Ia and their salts, wherein $R^1$, $R^2$ and $R^3$ are hydrogen and wherein A is selected from the radicals A2.cl1 to A2.cl81.

Table 182: Compounds of the formula Ia and their salts, wherein $R^1$ is methyl, $R^2$ and $R^3$ are hydrogen and wherein A is selected from the radicals A2.cl1 to A2.cl81.

Table 183: Compounds of the formula Ia and their salts, wherein $R^1$ is ethyl, $R^2$ and $R^3$ are hydrogen and wherein A is selected from the radicals A2.cl1 to A2.cl81.

Table 184: Compounds of the formula Ia and their salts, wherein $R^1$, $R^2$ and $R^3$ are hydrogen and wherein A is selected from the radicals A2.cm1 to A2.cm81.

Table 185: Compounds of the formula Ia and their salts, wherein $R^1$ is methyl, $R^2$ and $R^3$ are hydrogen and wherein A is selected from the radicals A2.cm1 to A2.cm81.

Table 186: Compounds of the formula Ia and their salts, wherein $R^1$ is ethyl, $R^2$ and $R^3$ are hydrogen and wherein A is selected from the radicals A2.cm1 to A2.cm81.

Table 187: Compounds of the formula Ia and their salts, wherein $R^1$, $R^2$ and $R^3$ are hydrogen and wherein A is selected from the radicals A2.cn1 to A2.cn81.

Table 188: Compounds of the formula Ia and their salts, wherein $R^1$ is methyl, $R^2$ and $R^3$ are hydrogen and wherein A is selected from the radicals A2.cn1 to A2.cn81.

Table 189: Compounds of the formula Ia and their salts, wherein $R^1$ is ethyl, $R^2$ and $R^3$ are hydrogen and wherein A is selected from the radicals A2.cn1 to A2.cn81.

Table 190: Compounds of the formula Ia and their salts, wherein $R^1$, $R^2$ and $R^3$ are hydrogen and wherein A is selected from the radicals A2.co1 to A2.co81.

Table 191: Compounds of the formula Ia and their salts, wherein $R^1$ is methyl, $R^2$ and $R^3$ are hydrogen and wherein A is selected from the radicals A2.co1 to A2.co81.

Table 192: Compounds of the formula Ia and their salts, wherein $R^1$ is ethyl, $R^2$ and $R^3$ are hydrogen and wherein A is selected from the radicals A2.co1 to A2.co81.

Table 193: Compounds of the formula Ia and their salts, wherein $R^1$, $R^2$ and $R^3$ are hydrogen and wherein A is selected from the radicals A2.da1 to A2.da81.

Table 194: Compounds of the formula Ia and their salts, wherein $R^1$ is methyl, $R^2$ and $R^3$ are hydrogen and wherein A is selected from the radicals A2.da1 to A2.da81.

Table 195: Compounds of the formula Ia and their salts, wherein $R^1$ is ethyl, $R^2$ and $R^3$ are hydrogen and wherein A is selected from the radicals A2.da1 to A2.da81.

Table 196: Compounds of the formula Ia and their salts, wherein $R^1$, $R^2$ and $R^3$ are hydrogen and wherein A is selected from the radicals A2.db1 to A2.db81.

Table 197: Compounds of the formula Ia and their salts, wherein $R^1$ is methyl, $R^2$ and $R^3$ are hydrogen and wherein A is selected from the radicals A2.db1 to A2.db81.

Table 198: Compounds of the formula Ia and their salts, wherein $R^1$ is ethyl, $R^2$ and $R^3$ are hydrogen and wherein A is selected from the radicals A2.db1 to A2.db81.

Table 199: Compounds of the formula Ia and their salts, wherein $R^1$, $R^2$ and $R^3$ are hydrogen and wherein A is selected from the radicals A2.dc1 to A2.dc81.

Table 200: Compounds of the formula Ia and their salts, wherein $R^1$ is methyl, $R^2$ and $R^3$ are hydrogen and wherein A is selected from the radicals A2.dc1 to A2.dc81.

Table 201: Compounds of the formula Ia and their salts, wherein $R^1$ is ethyl, $R^2$ and $R^3$ are hydrogen and wherein A is selected from the radicals A2.dc1 to A2.dc81.

Table 202: Compounds of the formula Ia and their salts, wherein $R^1$, $R^2$ and $R^3$ are hydrogen and wherein A is selected from the radicals A2.dd1 to A2.dd81.

Table 203: Compounds of the formula Ia and their salts, wherein $R^1$ is methyl, $R^2$ and $R^3$ are hydrogen and wherein A is selected from the radicals A2.dd1 to A2.dd81.
Table 204: Compounds of the formula Ia and their salts, wherein $R^1$ is ethyl, $R^2$ and $R^3$ are hydrogen and wherein A is selected from the radicals A2.dd1 to A2.dd81.
Table 205: Compounds of the formula Ia and their salts, wherein $R^1$, $R^2$ and $R^3$ are hydrogen and wherein A is selected from the radicals A2.de1 to A2.de81.
Table 206: Compounds of the formula Ia and their salts, wherein $R^1$ is methyl, $R^2$ and $R^3$ are hydrogen and wherein A is selected from the radicals A2.de1 to A2.de81.
Table 207: Compounds of the formula Ia and their salts, wherein $R^1$ is ethyl, $R^2$ and $R^3$ are hydrogen and wherein A is selected from the radicals A2.de1 to A2.de81.
Table 208: Compounds of the formula Ia and their salts, wherein $R^1$, $R^2$ and $R^3$ are hydrogen and wherein A is selected from the radicals A2.df1 to A2.df81.
Table 209: Compounds of the formula Ia and their salts, wherein $R^1$ is methyl, $R^2$ and $R^3$ are hydrogen and wherein A is selected from the radicals A2.df1 to A2.df81.
Table 210: Compounds of the formula Ia and their salts, wherein $R^1$ is ethyl, $R^2$ and $R^3$ are hydrogen and wherein A is selected from the radicals A2.df1 to A2.df81.
Table 211: Compounds of the formula Ia and their salts, wherein $R^1$, $R^2$ and $R^3$ are hydrogen and wherein A is selected from the radicals A2.dg1 to A2.dg81.
Table 212: Compounds of the formula Ia and their salts, wherein $R^1$ is methyl, $R^2$ and $R^3$ are hydrogen and wherein A is selected from the radicals A2.dg1 to A2.dg81.
Table 213: Compounds of the formula Ia and their salts, wherein $R^1$ is ethyl, $R^2$ and $R^3$ are hydrogen and wherein A is selected from the radicals A2.dh1 to A2.dh81.
Table 214: Compounds of the formula Ia and their salts, wherein $R^1$, $R^2$ and $R^3$ are hydrogen and wherein A is selected from the radicals A2.di1 to A2.di81.
Table 215: Compounds of the formula Ia and their salts, wherein $R^1$ is methyl, $R^2$ and $R^3$ are hydrogen and wherein A is selected from the radicals A2.di1 to A2.di81.
Table 216: Compounds of the formula Ia and their salts, wherein $R^1$ is ethyl, $R^2$ and $R^3$ are hydrogen and wherein A is selected from the radicals A2.di1 to A2.di81.
Table 217: Compounds of the formula Ia and their salts, wherein $R^1$, $R^2$ and $R^3$ are hydrogen and wherein A is selected from the radicals A2.dk1 to A2.dk81.
Table 218: Compounds of the formula Ia and their salts, wherein $R^1$ is methyl, $R^2$ and $R^3$ are hydrogen and wherein A is selected from the radicals A2.dk1 to A2.dk81.
Table 219: Compounds of the formula Ia and their salts, wherein $R^1$ is ethyl, $R^2$ and $R^3$ are hydrogen and wherein A is selected from the radicals A2.dk1 to A2.dk81.
Table 220: Compounds of the formula Ia and their salts, wherein $R^1$, $R^2$ and $R^3$ are hydrogen and wherein A is selected from the radicals A2.dl1 to A2.dl81.
Table 221: Compounds of the formula Ia and their salts, wherein $R^1$ is methyl, $R^2$ and $R^3$ are hydrogen and wherein A is selected from the radicals A2.dl1 to A2.dl81.
Table 222: Compounds of the formula Ia and their salts, wherein $R^1$ is ethyl, $R^2$ and $R^3$ are hydrogen and wherein A is selected from the radicals A2.dl1 to A2.dl81.
Table 223: Compounds of the formula Ia and their salts, wherein $R^1$, $R^2$ and $R^3$ are hydrogen and wherein A is selected from the radicals A2.dm1 to A2.dm81.
Table 224: Compounds of the formula Ia and their salts, wherein $R^1$ is methyl, $R^2$ and $R^3$ are hydrogen and wherein A is selected from the radicals A2.dm1 to A2.dm81.
Table 225: Compounds of the formula Ia and their salts, wherein $R^1$ is ethyl, $R^2$ and $R^3$ are hydrogen and wherein A is selected from the radicals A2.dm1 to A2.dm81.
Table 226: Compounds of the formula Ia and their salts, wherein $R^1$, $R^2$ and $R^3$ are hydrogen and wherein A is selected from the radicals A2.dn1 to A2.dn81.
Table 227: Compounds of the formula Ia and their salts, wherein $R^1$ is methyl, $R^2$ and $R^3$ are hydrogen and wherein A is selected from the radicals A2.dn1 to A2.dn81.
Table 228: Compounds of the formula Ia and their salts, wherein $R^1$ is ethyl, $R^2$ and $R^3$ are hydrogen and wherein A is selected from the radicals A2.dn1 to A2.dn81.
Table 229: Compounds of the formula Ia and their salts, wherein $R^1$, $R^2$ and $R^3$ are hydrogen and wherein A is selected from the radicals A2.do1 to A2.do81.
Table 230: Compounds of the formula Ia and their salts, wherein $R^1$ is methyl, $R^2$ and $R^3$ are hydrogen and wherein A is selected from the radicals A2.do1 to A2.do81.
Table 231: Compounds of the formula Ia and their salts, wherein $R^1$ is ethyl, $R^2$ and $R^3$ are hydrogen and wherein A is selected from the radicals A2.do1 to A2.do81.

Another particular preferred embodiment relates to compounds of the formula Ia and to their salts, wherein A is a radical A3, as defined herein, in particular a radical A3, wherein $R^{43}$, $R^{53}$ and $R^{63}$ have the preferred meanings, in particular a pyrazole radical of the formulae A3.aa to A3.do, e.g. a radical selected from the pyrazole radicals A3.aa1-A3.aa81 to A3.do1 to A3.do81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment are the compounds given in the following tables 232 to 477.

Table 232: Compounds of the formula Ia and their salts, wherein $R^1$, $R^2$ and $R^3$ are hydrogen and wherein A is selected from the radicals A3.aa1 to A3.aa81.
Table 233: Compounds of the formula Ia and their salts, wherein $R^1$ is methyl, $R^2$ and $R^3$ are hydrogen and wherein A is selected from the radicals A3.aa1 to A3.aa81.
Table 234: Compounds of the formula Ia and their salts, wherein $R^1$ is ethyl, $R^2$ and $R^3$ are hydrogen and wherein A is selected from the radicals A3.aa1 to A3.aa81.
Table 235: Compounds of the formula Ia and their salts, wherein $R^1$, $R^2$ and $R^3$ are hydrogen and wherein A is selected from the radicals A3.ab1 to A3.ab81.
Table 236: Compounds of the formula Ia and their salts, wherein $R^1$ is methyl, $R^2$ and $R^3$ are hydrogen and wherein A is selected from the radicals A3.ab1 to A3.ab81.
Table 237: Compounds of the formula Ia and their salts, wherein $R^1$ is ethyl, $R^2$ and $R^3$ are hydrogen and wherein A is selected from the radicals A3.ab1 to A3.ab81.
Table 238: Compounds of the formula Ia and their salts, wherein $R^1$, $R^2$ and $R^3$ are hydrogen and wherein A is selected from the radicals A3.ac1 to A3.ac81.
Table 239: Compounds of the formula Ia and their salts, wherein $R^1$ is methyl, $R^2$ and $R^3$ are hydrogen and wherein A is selected from the radicals A3.ac1 to A3.ac81.
Table 240: Compounds of the formula Ia and their salts, wherein $R^1$ is ethyl, $R^2$ and $R^3$ are hydrogen and wherein A is selected from the radicals A3.ac1 to A3.ac81.

Table 241: Compounds of the formula Ia and their salts, wherein $R^1$, $R^2$ and $R^3$ are hydrogen and wherein A is selected from the radicals A3.ad1 to A3.ad81.

Table 242: Compounds of the formula Ia and their salts, wherein $R^1$ is methyl, $R^2$ and $R^3$ are hydrogen and wherein A is selected from the radicals A3.ad1 to A3.ad81.

Table 243: Compounds of the formula Ia and their salts, wherein $R^1$ is ethyl, $R^2$ and $R^3$ are hydrogen and wherein A is selected from the radicals A3.ad1 to A3.ad81.

Table 244: Compounds of the formula Ia and their salts, wherein $R^1$, $R^2$ and $R^3$ are hydrogen and wherein A is selected from the radicals A3.ae1 to A3.ae81.

Table 245: Compounds of the formula Ia and their salts, wherein $R^1$ is methyl, $R^2$ and $R^3$ are hydrogen and wherein A is selected from the radicals A3.ae1 to A3.ae81.

Table 246: Compounds of the formula Ia and their salts, wherein $R^1$ is ethyl, $R^2$ and $R^3$ are hydrogen and wherein A is selected from the radicals A3.ae1 to A3.ae81.

Table 247: Compounds of the formula Ia and their salts, wherein $R^1$, $R^2$ and $R^3$ are hydrogen and wherein A is selected from the radicals A3.af1 to A3.af81.

Table 248: Compounds of the formula Ia and their salts, wherein $R^1$ is methyl, $R^2$ and $R^3$ are hydrogen and wherein A is selected from the radicals A3.af1 to A3.af81.

Table 249: Compounds of the formula Ia and their salts, wherein $R^1$ is ethyl, $R^2$ and $R^3$ are hydrogen and wherein A is selected from the radicals A3.af1 to A3.af81.

Table 250: Compounds of the formula Ia and their salts, wherein $R^1$, $R^2$ and $R^3$ are hydrogen and wherein A is selected from the radicals A3.ag1 to A3.ag81.

Table 251: Compounds of the formula Ia and their salts, wherein $R^1$ is methyl, $R^2$ and $R^3$ are hydrogen and wherein A is selected from the radicals A3.ag1 to A3.ag81.

Table 252: Compounds of the formula Ia and their salts, wherein $R^1$ is ethyl, $R^2$ and $R^3$ are hydrogen and wherein A is selected from the radicals A3.ag1 to A3.ag81.

Table 253: Compounds of the formula Ia and their salts, wherein $R^1$, $R^2$ and $R^3$ are hydrogen and wherein A is selected from the radicals A3.ah1 to A3.ah81.

Table 254: Compounds of the formula Ia and their salts, wherein $R^1$ is methyl, $R^2$ and $R^3$ are hydrogen and wherein A is selected from the radicals A3.ah1 to A3.ah81.

Table 255: Compounds of the formula Ia and their salts, wherein $R^1$ is ethyl, $R^2$ and $R^3$ are hydrogen and wherein A is selected from the radicals A3.ah1 to A3.ah81.

Table 256: Compounds of the formula Ia and their salts, wherein $R^1$, $R^2$ and $R^3$ are hydrogen and wherein A is selected from the radicals A3.ai1 to A3.ai81.

Table 257: Compounds of the formula Ia and their salts, wherein $R^1$ is methyl, $R^2$ and $R^3$ are hydrogen and wherein A is selected from the radicals A3.ai1 to A3.ai81.

Table 258: Compounds of the formula Ia and their salts, wherein $R^1$ is ethyl, $R^2$ and $R^3$ are hydrogen and wherein A is selected from the radicals A3.ai1 to A3.ai81.

Table 259: Compounds of the formula Ia and their salts, wherein $R^1$, $R^2$ and $R^3$ are hydrogen and wherein A is selected from the radicals A3.ak1 to A3.ak81.

Table 260: Compounds of the formula Ia and their salts, wherein $R^1$ is methyl, $R^2$ and $R^3$ are hydrogen and wherein A is selected from the radicals A3.ak1 to A3.ak81.

Table 261: Compounds of the formula Ia and their salts, wherein $R^1$ is ethyl, $R^2$ and $R^3$ are hydrogen and wherein A is selected from the radicals A3.ak1 to A3.ak81.

Table 262: Compounds of the formula Ia and their salts, wherein $R^1$, $R^2$ and $R^3$ are hydrogen and wherein A is selected from the radicals A3.al1 to A3.al81.

Table 263: Compounds of the formula Ia and their salts, wherein $R^1$ is methyl, $R^2$ and $R^3$ are hydrogen and wherein A is selected from the radicals A3.al1 to A3.al81.

Table 264: Compounds of the formula Ia and their salts, wherein $R^1$ is ethyl, $R^2$ and $R^3$ are hydrogen and wherein A is selected from the radicals A3.al1 to A3.al81.

Table 265: Compounds of the formula Ia and their salts, wherein $R^1$, $R^2$ and $R^3$ are hydrogen and wherein A is selected from the radicals A3.am1 to A3.am81.

Table 266: Compounds of the formula Ia and their salts, wherein $R^1$ is methyl, $R^2$ and $R^3$ are hydrogen and wherein A is selected from the radicals A3.am1 to A3.am81.

Table 267: Compounds of the formula Ia and their salts, wherein $R^1$ is ethyl, $R^2$ and $R^3$ are hydrogen and wherein A is selected from the radicals A3.am1 to A3.am81.

Table 268: Compounds of the formula Ia and their salts, wherein $R^1$, $R^2$ and $R^3$ are hydrogen and wherein A is selected from the radicals A3.an1 to A3.an81.

Table 269: Compounds of the formula Ia and their salts, wherein $R^1$ is methyl, $R^2$ and $R^3$ are hydrogen and wherein A is selected from the radicals A3.an1 to A3.an81.

Table 270: Compounds of the formula Ia and their salts, wherein $R^1$ is ethyl, $R^2$ and $R^3$ are hydrogen and wherein A is selected from the radicals A3.an1 to A3.an81.

Table 271: Compounds of the formula Ia and their salts, wherein $R^1$, $R^2$ and $R^3$ are hydrogen and wherein A is selected from the radicals A3.ao1 to A3.ao81.

Table 272: Compounds of the formula Ia and their salts, wherein $R^1$ is methyl, $R^2$ and $R^3$ are hydrogen and wherein A is selected from the radicals A3.ao1 to A3.ao81.

Table 273: Compounds of the formula Ia and their salts, wherein $R^1$, $R^2$ and $R^3$ are hydrogen and wherein A is selected from the radicals A3.ba1 to A3.ba81.

Table 274: Compounds of the formula Ia and their salts, wherein $R^1$ is methyl, $R^2$ and $R^3$ are hydrogen and wherein A is selected from the radicals A3.ba1 to A3.ba81.

Table 275: Compounds of the formula Ia and their salts, wherein $R^1$ is ethyl, $R^2$ and $R^3$ are hydrogen and wherein A is selected from the radicals A3.ba1 to A3.ba81.

Table 276: Compounds of the formula Ia and their salts, wherein $R^1$, $R^2$ and $R^3$ are hydrogen and wherein A is selected from the radicals A3.bb1 to A3.bb81.

Table 277: Compounds of the formula Ia and their salts, wherein $R^1$ is methyl, $R^2$ and $R^3$ are hydrogen and wherein A is selected from the radicals A3.bb1 to A3.bb81.

Table 278: Compounds of the formula Ia and their salts, wherein $R^1$ is ethyl, $R^2$ and $R^3$ are hydrogen and wherein A is selected from the radicals A3.bb1 to A3.bb81.

Table 279: Compounds of the formula Ia and their salts, wherein $R^1$, $R^2$ and $R^3$ are hydrogen and wherein A is selected from the radicals A3.bc1 to A3.bc81.

Table 280: Compounds of the formula Ia and their salts, wherein $R^1$ is methyl, $R^2$ and $R^3$ are hydrogen and wherein A is selected from the radicals A3.bc1 to A3.bc81.

Table 281: Compounds of the formula Ia and their salts, wherein $R^1$ is ethyl, $R^2$ and $R^3$ are hydrogen and wherein A is selected from the radicals A3.bc1 to A3.bc81.

Table 282: Compounds of the formula Ia and their salts, wherein $R^1$, $R^2$ and $R^3$ are hydrogen and wherein A is selected from the radicals A3.bd1 to A3.bd81.

Table 283: Compounds of the formula Ia and their salts, wherein $R^1$ is methyl, $R^2$ and $R^3$ are hydrogen and wherein A is selected from the radicals A3.bd1 to A3.bd81.

Table 284: Compounds of the formula Ia and their salts, wherein $R^1$ is ethyl, $R^2$ and $R^3$ are hydrogen and wherein A is selected from the radicals A3.bd1 to A3.bd81.

Table 285: Compounds of the formula Ia and their salts, wherein $R^1$, $R^2$ and $R^3$ are hydrogen and wherein A is selected from the radicals A3.be1 to A3.be81.

Table 286: Compounds of the formula Ia and their salts, wherein $R^1$ is methyl, $R^2$ and $R^3$ are hydrogen and wherein A is selected from the radicals A3.be1 to A3.be81.

Table 287: Compounds of the formula Ia and their salts, wherein $R^1$ is ethyl, $R^2$ and $R^3$ are hydrogen and wherein A is selected from the radicals A3.be1 to A3.be81.

Table 288: Compounds of the formula Ia and their salts, wherein $R^1$, $R^2$ and $R^3$ are hydrogen and wherein A is selected from the radicals A3.bf1 to A3.bf81.

Table 289: Compounds of the formula Ia and their salts, wherein $R^1$ is methyl, $R^2$ and $R^3$ are hydrogen and wherein A is selected from the radicals A3.bf1 to A3.bf81.

Table 290: Compounds of the formula Ia and their salts, wherein $R^1$ is ethyl, $R^2$ and $R^3$ are hydrogen and wherein A is selected from the radicals A3.bf1 to A3.bf81.

Table 291: Compounds of the formula Ia and their salts, wherein $R^1$, $R^2$ and $R^3$ are hydrogen and wherein A is selected from the radicals A3.bg1 to A3.bg81.

Table 292: Compounds of the formula Ia and their salts, wherein $R^1$ is methyl, $R^2$ and $R^3$ are hydrogen and wherein A is selected from the radicals A3.bg1 to A3.bg81.

Table 293: Compounds of the formula Ia and their salts, wherein $R^1$ is ethyl, $R^2$ and $R^3$ are hydrogen and wherein A is selected from the radicals A3.bg1 to A3.bg81.

Table 294: Compounds of the formula Ia and their salts, wherein $R^1$, $R^2$ and $R^3$ are hydrogen and wherein A is selected from the radicals A3.bh1 to A3.bh81.

Table 295: Compounds of the formula Ia and their salts, wherein $R^1$ is methyl, $R^2$ and $R^3$ are hydrogen and wherein A is selected from the radicals A3.bh1 to A3.bh81.

Table 296: Compounds of the formula Ia and their salts, wherein $R^1$ is ethyl, $R^2$ and $R^3$ are hydrogen and wherein A is selected from the radicals A3.bh1 to A3.bh81.

Table 297: Compounds of the formula Ia and their salts, wherein $R^1$, $R^2$ and $R^3$ are hydrogen and wherein A is selected from the radicals A3.bi1 to A3.bi81.

Table 298: Compounds of the formula Ia and their salts, wherein $R^1$ is methyl, $R^2$ and $R^3$ are hydrogen and wherein A is selected from the radicals A3.bi1 to A3.bi81.

Table 299: Compounds of the formula Ia and their salts, wherein $R^1$ is ethyl, $R^2$ and $R^3$ are hydrogen and wherein A is selected from the radicals A3.bi1 to A3.bi81.

Table 300: Compounds of the formula Ia and their salts, wherein $R^1$, $R^2$ and $R^3$ are hydrogen and wherein A is selected from the radicals A3.bk1 to A3.bk81.

Table 301: Compounds of the formula Ia and their salts, wherein $R^1$ is methyl, $R^2$ and $R^3$ are hydrogen and wherein A is selected from the radicals A3.bk1 to A3.bk81.

Table 302: Compounds of the formula Ia and their salts, wherein $R^1$ is ethyl, $R^2$ and $R^3$ are hydrogen and wherein A is selected from the radicals A3.bk1 to A3.bk81.

Table 303: Compounds of the formula Ia and their salts, wherein $R^1$, $R^2$ and $R^3$ are hydrogen and wherein A is selected from the radicals A3.bl1 to A3.bl81.

Table 304: Compounds of the formula Ia and their salts, wherein $R^1$ is methyl, $R^2$ and $R^3$ are hydrogen and wherein A is selected from the radicals A3.bl1 to A3.bl81.

Table 305: Compounds of the formula Ia and their salts, wherein $R^1$ is ethyl, $R^2$ and $R^3$ are hydrogen and wherein A is selected from the radicals A3.bl1 to A3.bl81.

Table 306: Compounds of the formula Ia and their salts, wherein $R^1$, $R^2$ and $R^3$ are hydrogen and wherein A is selected from the radicals A3.bm1 to A3.bm81.

Table 307: Compounds of the formula Ia and their salts, wherein $R^1$ is methyl, $R^2$ and $R^3$ are hydrogen and wherein A is selected from the radicals A3.bm1 to A3.bm81.

Table 308: Compounds of the formula Ia and their salts, wherein $R^1$ is ethyl, $R^2$ and $R^3$ are hydrogen and wherein A is selected from the radicals A3.bm1 to A3.bm81.

Table 309: Compounds of the formula Ia and their salts, wherein $R^1$, $R^2$ and $R^3$ are hydrogen and wherein A is selected from the radicals A3.bn1 to A3.bn81.

Table 310: Compounds of the formula Ia and their salts, wherein $R^1$ is methyl, $R^2$ and $R^3$ are hydrogen and wherein A is selected from the radicals A3.bn1 to A3.bn81.

Table 311: Compounds of the formula Ia and their salts, wherein $R^1$ is ethyl, $R^2$ and $R^3$ are hydrogen and wherein A is selected from the radicals A3.bn1 to A3.bn81.

Table 312: Compounds of the formula Ia and their salts, wherein $R^1$, $R^2$ and $R^3$ are hydrogen and wherein A is selected from the radicals A3.bo1 to A3.bo81.

Table 313: Compounds of the formula Ia and their salts, wherein $R^1$ is methyl, $R^2$ and $R^3$ are hydrogen and wherein A is selected from the radicals A3.bo1 to A3.bo81.

Table 314: Compounds of the formula Ia and their salts, wherein $R^1$, $R^2$ and $R^3$ are hydrogen and wherein A is selected from the radicals A3.ca1 to A3.ca81.

Table 315: Compounds of the formula Ia and their salts, wherein $R^1$ is methyl, $R^2$ and $R^3$ are hydrogen and wherein A is selected from the radicals A3.ca1 to A3.ca81.

Table 316: Compounds of the formula Ia and their salts, wherein $R^1$ is ethyl, $R^2$ and $R^3$ are hydrogen and wherein A is selected from the radicals A3.ca1 to A3.ca81.

Table 317: Compounds of the formula Ia and their salts, wherein $R^1$, $R^2$ and $R^3$ are hydrogen and wherein A is selected from the radicals A3.cb1 to A3.cb81.

Table 318: Compounds of the formula Ia and their salts, wherein $R^1$ is methyl, $R^2$ and $R^3$ are hydrogen and wherein A is selected from the radicals A3.cb1 to A3.cb81.

Table 319: Compounds of the formula Ia and their salts, wherein $R^1$ is ethyl, $R^2$ and $R^3$ are hydrogen and wherein A is selected from the radicals A3.cb1 to A3.cb81.

Table 320: Compounds of the formula Ia and their salts, wherein $R^1$, $R^2$ and $R^3$ are hydrogen and wherein A is selected from the radicals A3.cc1 to A3.cc81.

Table 321: Compounds of the formula Ia and their salts, wherein $R^1$ is methyl, $R^2$ and $R^3$ are hydrogen and wherein A is selected from the radicals A3.cc1 to A3.cc81.

Table 322: Compounds of the formula Ia and their salts, wherein $R^1$ is ethyl, $R^2$ and $R^3$ are hydrogen and wherein A is selected from the radicals A3.cc1 to A3.cc81.

Table 323: Compounds of the formula Ia and their salts, wherein $R^1$, $R^2$ and $R^3$ are hydrogen and wherein A is selected from the radicals A3.cd1 to A3.cd81.

Table 324: Compounds of the formula Ia and their salts, wherein $R^1$ is methyl, $R^2$ and $R^3$ are hydrogen and wherein A is selected from the radicals A3.cd1 to A3.cd81.

Table 325: Compounds of the formula Ia and their salts, wherein $R^1$ is ethyl, $R^2$ and $R^3$ are hydrogen and wherein A is selected from the radicals A3.cd1 to A3.cd81.

Table 326: Compounds of the formula Ia and their salts, wherein $R^1$, $R^2$ and $R^3$ are hydrogen and wherein A is selected from the radicals A3.ce1 to A3.ce81.

Table 327: Compounds of the formula Ia and their salts, wherein $R^1$ is methyl, $R^2$ and $R^3$ are hydrogen and wherein A is selected from the radicals A3.ce1 to A3.ce81.

Table 328: Compounds of the formula Ia and their salts, wherein $R^1$ is ethyl, $R^2$ and $R^3$ are hydrogen and wherein A is selected from the radicals A3.ce1 to A3.ce81.

Table 329: Compounds of the formula Ia and their salts, wherein $R^1$, $R^2$ and $R^3$ are hydrogen and wherein A is selected from the radicals A3.cf1 to A3.cf81.

Table 330: Compounds of the formula Ia and their salts, wherein $R^1$ is methyl, $R^2$ and $R^3$ are hydrogen and wherein A is selected from the radicals A3.cf1 to A3.cf81.

Table 331: Compounds of the formula Ia and their salts, wherein $R^1$ is ethyl, $R^2$ and $R^3$ are hydrogen and wherein A is selected from the radicals A3.cf1 to A3.cf81.

Table 332: Compounds of the formula Ia and their salts, wherein $R^1$, $R^2$ and $R^3$ are hydrogen and wherein A is selected from the radicals A3.cg1 to A3.cg81.

Table 333: Compounds of the formula Ia and their salts, wherein $R^1$ is methyl, $R^2$ and $R^3$ are hydrogen and wherein A is selected from the radicals A3.cg1 to A3.cg81.

Table 334: Compounds of the formula Ia and their salts, wherein $R^1$ is ethyl, $R^2$ and $R^3$ are hydrogen and wherein A is selected from the radicals A3.cg1 to A3.cg81.

Table 335: Compounds of the formula Ia and their salts, wherein $R^1$, $R^2$ and $R^3$ are hydrogen and wherein A is selected from the radicals A3.ch1 to A3.ch81.

Table 336: Compounds of the formula Ia and their salts, wherein $R^1$ is methyl, $R^2$ and $R^3$ are hydrogen and wherein A is selected from the radicals A3.ch1 to A3.ch81.

Table 337: Compounds of the formula Ia and their salts, wherein $R^1$ is ethyl, $R^2$ and $R^3$ are hydrogen and wherein A is selected from the radicals A3.ch1 to A3.ch81.

Table 338: Compounds of the formula Ia and their salts, wherein $R^1$, $R^2$ and $R^3$ are hydrogen and wherein A is selected from the radicals A3.ci1 to A3.ci81.

Table 339: Compounds of the formula Ia and their salts, wherein $R^1$ is methyl, $R^2$ and $R^3$ are hydrogen and wherein A is selected from the radicals A3.ci1 to A3.ci81.

Table 340: Compounds of the formula Ia and their salts, wherein $R^1$ is ethyl, $R^2$ and $R^3$ are hydrogen and wherein A is selected from the radicals A3.ci1 to A3.ci81.

Table 341: Compounds of the formula Ia and their salts, wherein $R^1$, $R^2$ and $R^3$ are hydrogen and wherein A is selected from the radicals A3.ck1 to A3.ck81.

Table 342: Compounds of the formula Ia and their salts, wherein $R^1$ is methyl, $R^2$ and $R^3$ are hydrogen and wherein A is selected from the radicals A3.ck1 to A3.ck81.

Table 343: Compounds of the formula Ia and their salts, wherein $R^1$ is ethyl, $R^2$ and $R^3$ are hydrogen and wherein A is selected from the radicals A3.ck1 to A3.ck81.

Table 344: Compounds of the formula Ia and their salts, wherein $R^1$, $R^2$ and $R^3$ are hydrogen and wherein A is selected from the radicals A3.cl1 to A3.cl81.

Table 345: Compounds of the formula Ia and their salts, wherein $R^1$ is methyl, $R^2$ and $R^3$ are hydrogen and wherein A is selected from the radicals A3.cl1 to A3.cl81.

Table 346: Compounds of the formula Ia and their salts, wherein $R^1$ is ethyl, $R^2$ and $R^3$ are hydrogen and wherein A is selected from the radicals A3.cl1 to A3.cl81.

Table 347: Compounds of the formula Ia and their salts, wherein $R^1$, $R^2$ and $R^3$ are hydrogen and wherein A is selected from the radicals A3.cm1 to A3.cm81.

Table 348: Compounds of the formula Ia and their salts, wherein $R^1$ is methyl, $R^2$ and $R^3$ are hydrogen and wherein A is selected from the radicals A3.cm1 to A3.cm81.

Table 349: Compounds of the formula Ia and their salts, wherein $R^1$ is ethyl, $R^2$ and $R^3$ are hydrogen and wherein A is selected from the radicals A3.cm1 to A3.cm81.

Table 350: Compounds of the formula Ia and their salts, wherein $R^1$, $R^2$ and $R^3$ are hydrogen and wherein A is selected from the radicals A3.cn1 to A3.cn81.

Table 351: Compounds of the formula Ia and their salts, wherein $R^1$ is methyl, $R^2$ and $R^3$ are hydrogen and wherein A is selected from the radicals A3.cn1 to A3.cn81.

Table 352: Compounds of the formula Ia and their salts, wherein $R^1$ is ethyl, $R^2$ and $R^3$ are hydrogen and wherein A is selected from the radicals A3.cn1 to A3.cn81.

Table 353: Compounds of the formula Ia and their salts, wherein $R^1$, $R^2$ and $R^3$ are hydrogen and wherein A is selected from the radicals A3.co1 to A3.co81.

Table 354: Compounds of the formula Ia and their salts, wherein $R^1$ is methyl, $R^2$ and $R^3$ are hydrogen and wherein A is selected from the radicals A3.co1 to A3.co81.

Table 355: Compounds of the formula Ia and their salts, wherein $R^1$, $R^2$ and $R^3$ are hydrogen and wherein A is selected from the radicals A3.da1 to A3.da81.

Table 356: Compounds of the formula Ia and their salts, wherein $R^1$ is methyl, $R^2$ and $R^3$ are hydrogen and wherein A is selected from the radicals A3.da1 to A3.da81.

Table 357: Compounds of the formula Ia and their salts, wherein $R^1$ is ethyl, $R^2$ and $R^3$ are hydrogen and wherein A is selected from the radicals A3.da1 to A3.da81.

Table 358: Compounds of the formula Ia and their salts, wherein $R^1$, $R^2$ and $R^3$ are hydrogen and wherein A is selected from the radicals A3.db1 to A3.db81.

Table 359: Compounds of the formula Ia and their salts, wherein $R^1$ is methyl, $R^2$ and $R^3$ are hydrogen and wherein A is selected from the radicals A3.db1 to A3.db81.

Table 360: Compounds of the formula Ia and their salts, wherein $R^1$ is ethyl, $R^2$ and $R^3$ are hydrogen and wherein A is selected from the radicals A3.db1 to A3.db81.

Table 361: Compounds of the formula Ia and their salts, wherein $R^1$, $R^2$ and $R^3$ are hydrogen and wherein A is selected from the radicals A3.dc1 to A3.dc81.

Table 362: Compounds of the formula Ia and their salts, wherein $R^1$ is methyl, $R^2$ and $R^3$ are hydrogen and wherein A is selected from the radicals A3.dc1 to A3.dc81.

Table 363: Compounds of the formula Ia and their salts, wherein $R^1$ is ethyl, $R^2$ and $R^3$ are hydrogen and wherein A is selected from the radicals A3.dc1 to A3.dc81.

Table 364: Compounds of the formula Ia and their salts, wherein $R^1$, $R^2$ and $R^3$ are hydrogen and wherein A is selected from the radicals A3.dd1 to A3.dd81.

Table 365: Compounds of the formula Ia and their salts, wherein $R^1$ is methyl, $R^2$ and $R^3$ are hydrogen and wherein A is selected from the radicals A3.dd1 to A3.dd81.

Table 366: Compounds of the formula Ia and their salts, wherein $R^1$ is ethyl, $R^2$ and $R^3$ are hydrogen and wherein A is selected from the radicals A3.dd1 to A3.dd81.

Table 367: Compounds of the formula Ia and their salts, wherein $R^1$, $R^2$ and $R^3$ are hydrogen and wherein A is selected from the radicals A3.de1 to A3.de81.

Table 368: Compounds of the formula Ia and their salts, wherein $R^1$ is methyl, $R^2$ and $R^3$ are hydrogen and wherein A is selected from the radicals A3.de1 to A3.de81.

Table 369: Compounds of the formula Ia and their salts, wherein $R^1$ is ethyl, $R^2$ and $R^3$ are hydrogen and wherein A is selected from the radicals A3.de1 to A3.de81.

Table 370: Compounds of the formula Ia and their salts, wherein $R^1$, $R^2$ and $R^3$ are hydrogen and wherein A is selected from the radicals A3.df1 to A3.df81.

Table 371: Compounds of the formula Ia and their salts, wherein $R^1$ is methyl, $R^2$ and $R^3$ are hydrogen and wherein A is selected from the radicals A3.df1 to A3.df81.

Table 372: Compounds of the formula Ia and their salts, wherein $R^1$ is ethyl, $R^2$ and $R^3$ are hydrogen and wherein A is selected from the radicals A3.df1 to A3.df81.

Table 373: Compounds of the formula Ia and their salts, wherein $R^1$, $R^2$ and $R^3$ are hydrogen and wherein A is selected from the radicals A3.dg1 to A3.dg81.

Table 374: Compounds of the formula Ia and their salts, wherein $R^1$ is methyl, $R^2$ and $R^3$ are hydrogen and wherein A is selected from the radicals A3.dg1 to A3.dg81.

Table 375: Compounds of the formula Ia and their salts, wherein $R^1$ is ethyl, $R^2$ and $R^3$ are hydrogen and wherein A is selected from the radicals A3.dg1 to A3.dg81.

Table 376: Compounds of the formula Ia and their salts, wherein $R^1$, $R^2$ and $R^3$ are hydrogen and wherein A is selected from the radicals A3.dh1 to A3.dh81.

Table 377: Compounds of the formula Ia and their salts, wherein $R^1$ is methyl, $R^2$ and $R^3$ are hydrogen and wherein A is selected from the radicals A3.dh1 to A3.dh81.

Table 378: Compounds of the formula Ia and their salts, wherein $R^1$ is ethyl, $R^2$ and $R^3$ are hydrogen and wherein A is selected from the radicals A3.dh1 to A3.dh81.

Table 379: Compounds of the formula Ia and their salts, wherein $R^1$, $R^2$ and $R^3$ are hydrogen and wherein A is selected from the radicals A3.di1 to A3.di81.

Table 380: Compounds of the formula Ia and their salts, wherein $R^1$ is methyl, $R^2$ and $R^3$ are hydrogen and wherein A is selected from the radicals A3.di1 to A3.di81.

Table 381: Compounds of the formula Ia and their salts, wherein $R^1$ is ethyl, $R^2$ and $R^3$ are hydrogen and wherein A is selected from the radicals A3.di1 to A3.di81.

Table 382: Compounds of the formula Ia and their salts, wherein $R^1$, $R^2$ and $R^3$ are hydrogen and wherein A is selected from the radicals A3.dk1 to A3.dk81.

Table 383: Compounds of the formula Ia and their salts, wherein $R^1$ is methyl, $R^2$ and $R^3$ are hydrogen and wherein A is selected from the radicals A3.dk1 to A3.dk81.

Table 384: Compounds of the formula Ia and their salts, wherein $R^1$ is ethyl, $R^2$ and $R^3$ are hydrogen and wherein A is selected from the radicals A3.dk1 to A3.dk81.

Table 385: Compounds of the formula Ia and their salts, wherein $R^1$, $R^2$ and $R^3$ are hydrogen and wherein A is selected from the radicals A3.dl1 to A3.dl81.

Table 386: Compounds of the formula Ia and their salts, wherein $R^1$ is methyl, $R^2$ and $R^3$ are hydrogen and wherein A is selected from the radicals A3.dl1 to A3.dl81.

Table 387: Compounds of the formula Ia and their salts, wherein $R^1$ is ethyl, $R^2$ and $R^3$ are hydrogen and wherein A is selected from the radicals A3.dl1 to A3.dl81.

Table 388: Compounds of the formula Ia and their salts, wherein $R^1$, $R^2$ and $R^3$ are hydrogen and wherein A is selected from the radicals A3.dm1 to A3.dm81.

Table 389: Compounds of the formula Ia and their salts, wherein $R^1$ is methyl, $R^2$ and $R^3$ are hydrogen and wherein A is selected from the radicals A3.dm1 to A3.dm81.

Table 390: Compounds of the formula Ia and their salts, wherein $R^1$ is ethyl, $R^2$ and $R^3$ are hydrogen and wherein A is selected from the radicals A3.dm1 to A3.dm81.

Table 391: Compounds of the formula Ia and their salts, wherein $R^1$, $R^2$ and $R^3$ are hydrogen and wherein A is selected from the radicals A3.dn1 to A3.dn81.

Table 392: Compounds of the formula Ia and their salts, wherein $R^1$ is methyl, $R^2$ and $R^3$ are hydrogen and wherein A is selected from the radicals A3.dn1 to A3.dn81.

Table 393: Compounds of the formula Ia and their salts, wherein $R^1$ is ethyl, $R^2$ and $R^3$ are hydrogen and wherein A is selected from the radicals A3.dn1 to A3.dn81.

Table 394: Compounds of the formula Ia and their salts, wherein $R^1$, $R^2$ and $R^3$ are hydrogen and wherein A is selected from the radicals A3.do1 to A3.do81.

Table 395: Compounds of the formula Ia and their salts, wherein $R^1$ is methyl, $R^2$ and $R^3$ are hydrogen and wherein A is selected from the radicals A3.do1 to A3.do81.

Table 396: Compounds of the formula Ia and their salts, wherein $R^1$, $R^2$ and $R^3$ are hydrogen and wherein A is selected from the radicals A3.ea1 to A3.ea81.

Table 397: Compounds of the formula Ia and their salts, wherein $R^1$ is methyl, $R^2$ and $R^3$ are hydrogen and wherein A is selected from the radicals A3.ea1 to A3.ea81.

Table 398: Compounds of the formula Ia and their salts, wherein $R^1$ is ethyl, $R^2$ and $R^3$ are hydrogen and wherein A is selected from the radicals A3.ea1 to A3.ea81.

Table 399: Compounds of the formula Ia and their salts, wherein $R^1$, $R^2$ and $R^3$ are hydrogen and wherein A is selected from the radicals A3.eb1 to A3.eb81.

Table 400: Compounds of the formula Ia and their salts, wherein $R^1$ is methyl, $R^2$ and $R^3$ are hydrogen and wherein A is selected from the radicals A3.eb1 to A3.eb81.

Table 401: Compounds of the formula Ia and their salts, wherein $R^1$ is ethyl, $R^2$ and $R^3$ are hydrogen and wherein A is selected from the radicals A3.eb1 to A3.eb81.

Table 402: Compounds of the formula Ia and their salts, wherein $R^1$, $R^2$ and $R^3$ are hydrogen and wherein A is selected from the radicals A3.ec1 to A3.ec81.

Table 403: Compounds of the formula Ia and their salts, wherein $R^1$ is methyl, $R^2$ and $R^3$ are hydrogen and wherein A is selected from the radicals A3.ec1 to A3.ec81.

Table 404: Compounds of the formula Ia and their salts, wherein $R^1$ is ethyl, $R^2$ and $R^3$ are hydrogen and wherein A is selected from the radicals A3.ec1 to A3.ec81.

Table 405: Compounds of the formula Ia and their salts, wherein $R^1$, $R^2$ and $R^3$ are hydrogen and wherein A is selected from the radicals A3.ed1 to A3.ed81.

Table 406: Compounds of the formula Ia and their salts, wherein $R^1$ is methyl, $R^2$ and $R^3$ are hydrogen and wherein A is selected from the radicals A3.ed1 to A3.ed81.

Table 407: Compounds of the formula Ia and their salts, wherein $R^1$ is ethyl, $R^2$ and $R^3$ are hydrogen and wherein A is selected from the radicals A3.ed1 to A3.ed81.

Table 408: Compounds of the formula Ia and their salts, wherein $R^1$, $R^2$ and $R^3$ are hydrogen and wherein A is selected from the radicals A3.ee1 to A3.ee81.

Table 409: Compounds of the formula Ia and their salts, wherein $R^1$ is methyl, $R^2$ and $R^3$ are hydrogen and wherein A is selected from the radicals A3.ee1 to A3.ee81.

Table 410: Compounds of the formula Ia and their salts, wherein $R^1$ is ethyl, $R^2$ and $R^3$ are hydrogen and wherein A is selected from the radicals A3.ee1 to A3.ee81.

Table 411: Compounds of the formula Ia and their salts, wherein $R^1$, $R^2$ and $R^3$ are hydrogen and wherein A is selected from the radicals A3.ef1 to A3.ef81.

Table 412: Compounds of the formula Ia and their salts, wherein $R^1$ is methyl, $R^2$ and $R^3$ are hydrogen and wherein A is selected from the radicals A3.ef1 to A3.ef81.

Table 413: Compounds of the formula Ia and their salts, wherein $R^1$ is ethyl, $R^2$ and $R^3$ are hydrogen and wherein A is selected from the radicals A3.ef1 to A3.ef81.

Table 414: Compounds of the formula Ia and their salts, wherein $R^1$, $R^2$ and $R^3$ are hydrogen and wherein A is selected from the radicals A3.eg1 to A3.eg81.

Table 415: Compounds of the formula Ia and their salts, wherein $R^1$ is methyl, $R^2$ and $R^3$ are hydrogen and wherein A is selected from the radicals A3.eg1 to A3.eg81.

Table 416: Compounds of the formula Ia and their salts, wherein $R^1$ is ethyl, $R^2$ and $R^3$ are hydrogen and wherein A is selected from the radicals A3.eg1 to A3.eg81.

Table 417: Compounds of the formula Ia and their salts, wherein $R^1$, $R^2$ and $R^3$ are hydrogen and wherein A is selected from the radicals A3.eh1 to A3.eh81.

Table 418: Compounds of the formula Ia and their salts, wherein $R^1$ is methyl, $R^2$ and $R^3$ are hydrogen and wherein A is selected from the radicals A3.eh1 to A3.eh81.

Table 419: Compounds of the formula Ia and their salts, wherein $R^1$ is ethyl, $R^2$ and $R^3$ are hydrogen and wherein A is selected from the radicals A3.eh1 to A3.eh81.

Table 420: Compounds of the formula Ia and their salts, wherein $R^1$, $R^2$ and $R^3$ are hydrogen and wherein A is selected from the radicals A3.ei1 to A3.ei81.

Table 421: Compounds of the formula Ia and their salts, wherein $R^1$ is methyl, $R^2$ and $R^3$ are hydrogen and wherein A is selected from the radicals A3.ei1 to A3.ei81.

Table 422: Compounds of the formula Ia and their salts, wherein $R^1$ is ethyl, $R^2$ and $R^3$ are hydrogen and wherein A is selected from the radicals A3.ei1 to A3.ei81.

Table 423: Compounds of the formula Ia and their salts, wherein $R^1$, $R^2$ and $R^3$ are hydrogen and wherein A is selected from the radicals A3.ek1 to A3.ek81.

Table 424: Compounds of the formula Ia and their salts, wherein $R^1$ is methyl, $R^2$ and $R^3$ are hydrogen and wherein A is selected from the radicals A3.ek1 to A3.ek81.

Table 425: Compounds of the formula Ia and their salts, wherein $R^1$ is ethyl, $R^2$ and $R^3$ are hydrogen and wherein A is selected from the radicals A3.ek1 to A3.ek81.

Table 426: Compounds of the formula Ia and their salts, wherein $R^1$, $R^2$ and $R^3$ are hydrogen and wherein A is selected from the radicals A3.el1 to A3.el81.

Table 427: Compounds of the formula Ia and their salts, wherein $R^1$ is methyl, $R^2$ and $R^3$ are hydrogen and wherein A is selected from the radicals A3.el1 to A3.el81.

Table 428: Compounds of the formula Ia and their salts, wherein $R^1$ is ethyl, $R^2$ and $R^3$ are hydrogen and wherein A is selected from the radicals A3.el1 to A3.el81.

Table 429: Compounds of the formula Ia and their salts, wherein $R^1$, $R^2$ and $R^3$ are hydrogen and wherein A is selected from the radicals A3.em1 to A3.em81.

Table 430: Compounds of the formula Ia and their salts, wherein $R^1$ is methyl, $R^2$ and $R^3$ are hydrogen and wherein A is selected from the radicals A3.em1 to A3.em81.

Table 431: Compounds of the formula Ia and their salts, wherein $R^1$ is ethyl, $R^2$ and $R^3$ are hydrogen and wherein A is selected from the radicals A3.em1 to A3.em81.

Table 432: Compounds of the formula Ia and their salts, wherein $R^1$, $R^2$ and $R^3$ are hydrogen and wherein A is selected from the radicals A3.en1 to A3.en81.

Table 433: Compounds of the formula Ia and their salts, wherein $R^1$ is methyl, $R^2$ and $R^3$ are hydrogen and wherein A is selected from the radicals A3.en1 to A3.en81.

Table 434: Compounds of the formula Ia and their salts, wherein $R^1$ is ethyl, $R^2$ and $R^3$ are hydrogen and wherein A is selected from the radicals A3.en1 to A3.en81.

Table 435: Compounds of the formula Ia and their salts, wherein $R^1$, $R^2$ and $R^3$ are hydrogen and wherein A is selected from the radicals A3.eo1 to A3.eo81.

Table 436: Compounds of the formula Ia and their salts, wherein $R^1$ is methyl, $R^2$ and $R^3$ are hydrogen and wherein A is selected from the radicals A3.eo1 to A3.eo81.

Table 437: Compounds of the formula Ia and their salts, wherein $R^1$, $R^2$ and $R^3$ are hydrogen and wherein A is selected from the radicals A3.fa1 to A3.fa81.

Table 438: Compounds of the formula Ia and their salts, wherein $R^1$ is methyl, $R^2$ and $R^3$ are hydrogen and wherein A is selected from the radicals A3.fa1 to A3.fa81.

Table 439: Compounds of the formula Ia and their salts, wherein $R^1$ is ethyl, $R^2$ and $R^3$ are hydrogen and wherein A is selected from the radicals A3.fa1 to A3.fa81.

Table 440: Compounds of the formula Ia and their salts, wherein $R^1$, $R^2$ and $R^3$ are hydrogen and wherein A is selected from the radicals A3.fb1 to A3.fb81.

Table 441: Compounds of the formula Ia and their salts, wherein $R^1$ is methyl, $R^2$ and $R^3$ are hydrogen and wherein A is selected from the radicals A3.fb1 to A3.fb81.

Table 442: Compounds of the formula Ia and their salts, wherein $R^1$ is ethyl, $R^2$ and $R^3$ are hydrogen and wherein A is selected from the radicals A3.fb1 to A3.fb81.

Table 443: Compounds of the formula Ia and their salts, wherein $R^1$, $R^2$ and $R^3$ are hydrogen and wherein A is selected from the radicals A3.fc1 to A3.fc81.

Table 444: Compounds of the formula Ia and their salts, wherein $R^1$ is methyl, $R^2$ and $R^3$ are hydrogen and wherein A is selected from the radicals A3.fc1 to A3.fc81.

Table 445: Compounds of the formula Ia and their salts, wherein $R^1$ is ethyl, $R^2$ and $R^3$ are hydrogen and wherein A is selected from the radicals A3.fc1 to A3.fc81.

Table 446: Compounds of the formula Ia and their salts, wherein $R^1$, $R^2$ and $R^3$ are hydrogen and wherein A is selected from the radicals A3.fd1 to A3.fd81.

Table 447: Compounds of the formula Ia and their salts, wherein $R^1$ is methyl, $R^2$ and $R^3$ are hydrogen and wherein A is selected from the radicals A3.fd1 to A3.fd81.

Table 448: Compounds of the formula Ia and their salts, wherein $R^1$ is ethyl, $R^2$ and $R^3$ are hydrogen and wherein A is selected from the radicals A3.fd1 to A3.fd81.

Table 449: Compounds of the formula Ia and their salts, wherein $R^1$, $R^2$ and $R^3$ are hydrogen and wherein A is selected from the radicals A3.fe1 to A3.fe81.

Table 450: Compounds of the formula Ia and their salts, wherein $R^1$ is methyl, $R^2$ and $R^3$ are hydrogen and wherein A is selected from the radicals A3.fe1 to A3.fe81.

Table 451: Compounds of the formula Ia and their salts, wherein $R^1$ is ethyl, $R^2$ and $R^3$ are hydrogen and wherein A is selected from the radicals A3.fe1 to A3.fe81.

Table 452: Compounds of the formula Ia and their salts, wherein $R^1$, $R^2$ and $R^3$ are hydrogen and wherein A is selected from the radicals A3.ff1 to A3.ff81.

Table 453: Compounds of the formula Ia and their salts, wherein $R^1$ is methyl, $R^2$ and $R^3$ are hydrogen and wherein A is selected from the radicals A3.ff1 to A3.ff81.

Table 454: Compounds of the formula Ia and their salts, wherein $R^1$ is ethyl, $R^2$ and $R^3$ are hydrogen and wherein A is selected from the radicals A3.ff1 to A3.ff81.

Table 455: Compounds of the formula Ia and their salts, wherein $R^1$, $R^2$ and $R^3$ are hydrogen and wherein A is selected from the radicals A3.fg1 to A3.fg81.

Table 456: Compounds of the formula Ia and their salts, wherein $R^1$ is methyl, $R^2$ and $R^3$ are hydrogen and wherein A is selected from the radicals A3.fg1 to A3.fg81.

Table 457: Compounds of the formula Ia and their salts, wherein $R^1$ is ethyl, $R^2$ and $R^3$ are hydrogen and wherein A is selected from the radicals A3.fg1 to A3.fg81.

Table 458: Compounds of the formula Ia and their salts, wherein $R^1$, $R^2$ and $R^3$ are hydrogen and wherein A is selected from the radicals A3.fh1 to A3.fh81.

Table 459: Compounds of the formula Ia and their salts, wherein $R^1$ is methyl, $R^2$ and $R^3$ are hydrogen and wherein A is selected from the radicals A3.fh1 to A3.fh81.

Table 460: Compounds of the formula Ia and their salts, wherein $R^1$ is ethyl, $R^2$ and $R^3$ are hydrogen and wherein A is selected from the radicals A3.fh1 to A3.fh81.

Table 461: Compounds of the formula Ia and their salts, wherein $R^1$, $R^2$ and $R^3$ are hydrogen and wherein A is selected from the radicals A3.fi1 to A3.fi81.

Table 462: Compounds of the formula Ia and their salts, wherein $R^1$ is methyl, $R^2$ and $R^3$ are hydrogen and wherein A is selected from the radicals A3.fi1 to A3.fi81.

Table 463: Compounds of the formula Ia and their salts, wherein $R^1$ is ethyl, $R^2$ and $R^3$ are hydrogen and wherein A is selected from the radicals A3.fi1 to A3.fi81.

Table 464: Compounds of the formula Ia and their salts, wherein $R^1$, $R^2$ and $R^3$ are hydrogen and wherein A is selected from the radicals A3.fk1 to A3.fk81.

Table 465: Compounds of the formula Ia and their salts, wherein $R^1$ is methyl, $R^2$ and $R^3$ are hydrogen and wherein A is selected from the radicals A3.fk1 to A3.fk81.

Table 466: Compounds of the formula Ia and their salts, wherein $R^1$ is ethyl, $R^2$ and $R^3$ are hydrogen and wherein A is selected from the radicals A3.fk1 to A3.fk81.

Table 467: Compounds of the formula Ia and their salts, wherein $R^1$, $R^2$ and $R^3$ are hydrogen and wherein A is selected from the radicals A3.fl1 to A3.fl81.

Table 468: Compounds of the formula Ia and their salts, wherein $R^1$ is methyl, $R^2$ and $R^3$ are hydrogen and wherein A is selected from the radicals A3.fl1 to A3.fl81.

Table 469: Compounds of the formula Ia and their salts, wherein $R^1$ is ethyl, $R^2$ and $R^3$ are hydrogen and wherein A is selected from the radicals A3.fl1 to A3.fl81.

Table 470: Compounds of the formula Ia and their salts, wherein $R^1$, $R^2$ and $R^3$ are hydrogen and wherein A is selected from the radicals A3.fm1 to A3.fm81.

Table 471: Compounds of the formula Ia and their salts, wherein $R^1$ is methyl, $R^2$ and $R^3$ are hydrogen and wherein A is selected from the radicals A3.fm1 to A3.fm81.

Table 472: Compounds of the formula Ia and their salts, wherein $R^1$ is ethyl, $R^2$ and $R^3$ are hydrogen and wherein A is selected from the radicals A3.fm1 to A3.fm81.

Table 473: Compounds of the formula Ia and their salts, wherein $R^1$, $R^2$ and $R^3$ are hydrogen and wherein A is selected from the radicals A3.fn1 to A3.fn81.

Table 474: Compounds of the formula Ia and their salts, wherein $R^1$ is methyl, $R^2$ and $R^3$ are hydrogen and wherein A is selected from the radicals A3.fn1 to A3.fn81.

Table 475: Compounds of the formula Ia and their salts, wherein $R^1$ is ethyl, $R^2$ and $R^3$ are hydrogen and wherein A is selected from the radicals A3.fn1 to A3.fn81.

Table 476: Compounds of the formula Ia and their salts, wherein $R^1$, $R^2$ and $R^3$ are hydrogen and wherein A is selected from the radicals A3.fo1 to A3.fo81.

Table 477: Compounds of the formula Ia and their salts, wherein $R^1$ is methyl, $R^2$ and $R^3$ are hydrogen and wherein A is selected from the radicals A3.fo1 to A3.fo81.

The compounds of the formulae I or II can be prepared by the standard methods of organic chemistry, e.g. by the methods described hereinafter or in the working examples:

The compounds of the formula I, wherein $X^1$ is O and $X^3$ is a lone pair, can be prepared e.g. according to the method depicted in scheme 1 by reacting activated pyrazole carboxylic acid derivative II with a 3-aminopyridine compound III (see e.g. Houben-Weyl: "Methoden der organ. Chemie" [Methods of Organic Chemistry], Georg-Thieme-Verlag, Stuttgart, N.Y. 1985, Volume E5, pp. 941-1045). Activated pyrazole carboxylic acid derivatives II are, for example, halides, activated esters, anhydrides, azides, for example chlorides, fluorides, bromides, para-nitrophenyl esters, pentafluorophenyl esters, N-hydroxysuccinimides, hydroxybenzotriazol-1-yl esters. In scheme 1, the radicals A, $R^1$, $R^2$ and $R^3$ have the meanings mentioned above and in particular the meanings mentioned as being preferred, X is a suitable leaving group such as halogen, $N_3$, paranitrophenoxy or pentafluorophenoxy etc.

Scheme 1:

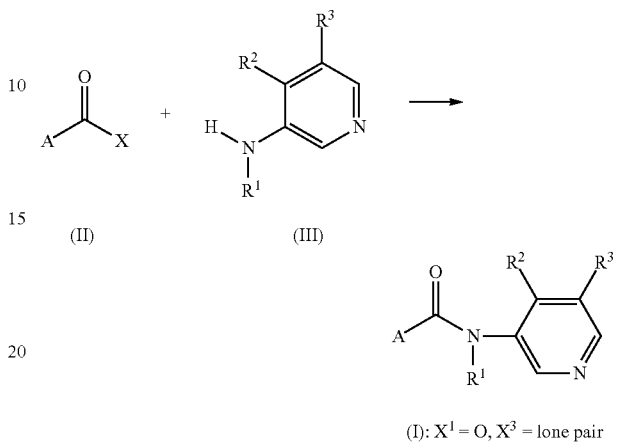

The active compounds of the formula I, wherein $X^1$ is O and $X^3$ is a lone pair, can also be prepared, for example, by reacting the pyrazole carboxylic acid IV with a 3-aminopyridine compound III in the presence of a coupling agent according to scheme 2. In scheme 2, the radicals A, $R^1$, $R^2$ and $R^3$ have the meanings given above and in particular the meanings given as being preferred.

Scheme 2:

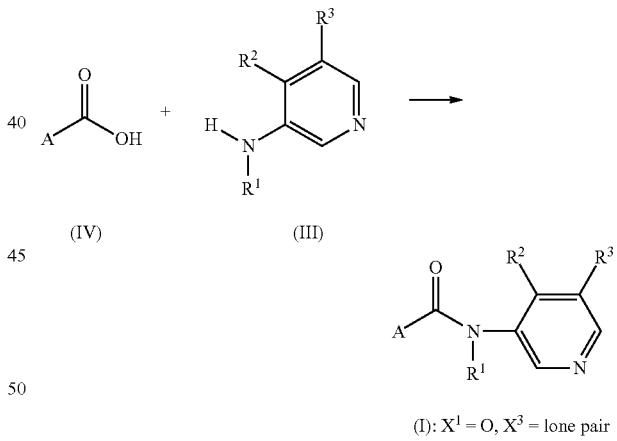

Suitable coupling agents are, for example:
coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide;
coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun. 1972, 942];
coupling agents based on phosphonium salts, for example (benzotriazol-1-yloxy)tris(dimethylamino)phosphonium hexafluorophosphate [B. Castro, J. R. Domoy, G.

Evin, C. Selve, Tetrahedron Lett. 1975, 14, 1219], (benzotriazol-1-yloxy)tripyrrolidinophosphonium hexafluorophosphate [J. Coste et al., Tetrahedron Lett. 1990, 31, 205];

coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647];

coupling agents which form acid chlorides, for example bis-(2-oxooxazolidinyl)phosphinic chloride [J. Diago-Mesequer, Synthesis 1980, 547].

Compounds I where $X^1$ is O, $X_3$ is a lone pair and $R^1$ is different from hydrogen can also be prepared by alkylating the amides I (in which $R^1$ is hydrogen and which can be obtained according to scheme 1 or 2) using suitable alkylating agents in the presence of bases.

Scheme 3:

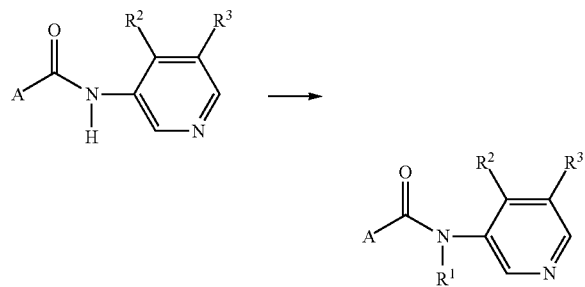

The pyrazole carboxylic acids IV and their activated derivatives II as well as 3-aminopyridine compounda III are known in the art or are commercially available or can be prepared by methods known from the literature.

Compounds of the formula I, wherein $X^1$ is different from oxygen, can be prepared from the compounds Ia by standard methods:

Compounds of the formula I, wherein $X^1$ is S, can be prepared e.g. by reacting a compound Ia with 2,4-bis(4-methoxyphenyl)-1,3,2,4-dithiadiphosphetane-2,4-disulfide or phorphorus pentasulfide according to the method described by M. Jesberger et al. in Synthesis 2003, 1929.

Compounds of the formula I, wherein $X^1$ is $NR^{1a}$, can be prepared e.g. by reacting a compound Ia with by reacting a compound Ia with 2,4-bis(4-methoxyphenyl)-1,3,2,4-dithiadiphosphetane-2,4-disulfide to obtain the corresponding thioamide (compound I, wherein $X^1$ is S) which is then reacted with an appropriate amine according to the method described by V. Glushkov et al. in Pharmaceutical Chemistry Journal 2005, 39(10), 533-536.

Compounds of the formula II, wherein $X^2$=$SR^{2a}$, can be prepared by alkylation of the corresponding thioamide (compound I, wherein $X^1$ is S) by reaction with an alkylating agent according to the method described by V. Glushkov et al. in Pharmaceutical Chemistry Journal 2005, 39(10), 533-536. In a similar manner, compounds I, wherein $X^2$ is $OR^{2a}$ or $NR^{2b}R^{2c}$ can be obtained. Compounds of the formula II, wherein $X^2$=$SOR^{2a}$ or $SO_2R^{2a}$ can be obtained by oxidation of compounds II with $X^2$=$SR^{2a}$.

Compounds of the formulae I and II, wherein $X^3$ is O, can be prepared by oxidation of compounds I, wherein $X^3$ is a lone pair, according to standard methods of preparing pyridine N-oxides, e.g. by the method described C. Botteghi et al. in Journal of Organometallic Chemistry 1989, 370, 17-31.

As a rule, the compounds of the formulae I or II can be prepared by the methods described above. If individual compounds cannot be prepared via the above-described routes, they can be prepared by derivatization of other compounds I or II or by customary modifications of the synthesis routes described. For example, in individual cases, certain compounds I or II can advantageously be prepared from other compounds I or II by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the general formulae I or II may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formulae (I) or (II) or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formulae (I) or (II) or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes.

The invention further provides an agricultural composition for combating such invertebrate pests, which comprises such an amount of at least one compound of the general formulae I or II or at least one agriculturally useful salt or N-oxide thereof and at least one inert liquid and/or solid agronomically acceptable carrier that has a pesticidal action and, if desired, at least one surfactant.

Such a composition may contain a single active compound of the formulae I or II or a salt or N-oxide thereof or a mixture of several active compounds I or II or their salts according to the present invention. The composition according to the present invention may comprise an individual isomer or mixtures of isomers as well as individual tautomers or mixtures of tautomers.

The compounds of the formulae I or II and the pesticidal compositions comprising them are effective agents for controlling arthropod pests and nematodes. Invertebrate pests controlled by the compounds of formulae I or II include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibemia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicomis, Diabrotica* 12 *punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrostemum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus homi, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantii* and, *and Viteus vitifolii;* termites (Isoptera), e.g. *Calotermes flavicollis, Leucotermes flavipes, Reticulitermes flavipes, Reticulitermes lucifugus und Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali,*

*Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis; siphonatera,* e.g. *Xenopsylla cheopsis, Ceratophyllus* spp.

The compositions and compounds of formulae I or II are useful for the control of nematodes, especially plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylen-chus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formulae I or II are used for controlling insects or arachnids, in particular insects of the orders Lepidoptera, Coleoptera, Thysanoptera and Homoptera and arachnids of the order Acarina. The compounds of the formulae I or II according to the present invention are particularly useful for controlling insects of the order Thysanoptera and Homoptera.

The compounds of formula formulae I or II or the pesticidal compositions comprising them may be used to protect growing plants and crops from attack or infestation by invertebrate pests, especially insects, acaridae or arachnids by contacting the plant/crop with a pesticidally effective amount of compounds of formulae I or II. The term "crop" refers both to growing and harvested crops.

The compounds of formulae I or II can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl suffoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcoholsi, polyvinylpyrrolidones, polyacrylates, polymethacrylates, polybute-nes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compounds of formulae I or II can be used as such, in the form of their formulations or the use forms prepared therefrom, for example in the form of directly sprayable solutions, powders, suspensions or dispersions, emulsions, oil dispersions, pastes, dusta-ble products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formula-tion with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weightof carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formulae I or II are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formulae I or II for seed treatment comprise from 0.5 to 80 wt % of the active ingredient, from 0.05 to 5 wt % of a wetter, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formulae I or II are effective through both contact (via soil, glass, wall, bed net, carpet, plant parts or animal parts), and ingestion (bait, or plant part).

For use against ants, termites, wasps, flies, mosquitos, crickets, or cockroaches, compounds of formulae I or II are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formulae I or II as aerosols (e.g in spray cans), oil sprays or pump sprays are highly suitable for the non-professional user for controlling pests such as flies, fleas, ticks, mosquitos or cockroaches. Aerosol recipes are preferably com-posed of the active compound, solvents such as lower alcohols (e.g. methanol, etha-nol, propanol, butanol), ketones (e.g. acetone, methyl ethyl ketone), paraffin hydrocar-bons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, am-photeric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formulae I or II and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formulae I or II and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for exam-pie are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formulae I and II or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formulae I or II into contact with each other, and "seed dressing" to methods of seed treatment which provide the seeds with an amount of the compounds of formulae I or II, i.e. which generate a seed comprising the compound of formulae I or II. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formulae I or II or the enantiomers or veterinarily acceptable salts thereof are in particular also suitable for being used for combating parasites in and on animals.

A further object of the present invention is therefore to provide new methods for controlling parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formulae I or II or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formulae I or II or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formulae I or II or the enantiomers or veterinarily acceptable salts thereof or a composition comprising it.

Activity of compounds against agricultural pests does not suggest their suitability for control of endo- and ectoparasites in and on animals which requires, for example, low, nonemetic dosages in the case of oral application, metabolic compatibility with the animal, low toxicity, and a safe handling.

Surprisingly, it has been found that compounds of formulae I or II are suitable for combating endo- and ectoparasites in and on animals.

Compounds of formulae I or II or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels.

Compounds of formulae I or II or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formulae I or II or the enantiomers or veterinarily acceptable salts thereof and compositions comprising them are suitable for systemic and/or non-systemic control of ecto- and/or endoparasites. They are active against all or some stages of development.

The compounds of formulae I or II are especially useful for combating ectoparasites.

The compounds of formulae I or II are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freebomi, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea,*

*Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis*, lice (Phthiraptera), e.g. *Pediculus humanus capitis, Pediculus humanus corporis, Pthirus pubis, Haematopinus eurystemus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Amblycerina and Ischnocerina), e.g. *Trimenopon* spp., *Menopon* spp., *Trinoton* spp., *Bovicola* spp., *Wemeckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formulae I or II and compositions containing them are particularly useful for the control of pests from the orders Diptera, Siphonaptera and Ixodida.

Moreover, the use of the formulae I or II and compositions containing them for combating mosquitoes is especially preferred.

The use of the compounds of formulae I or II and compositions containing them for combating flies is a further preferred embodiment of the present invention.

Furthermore, the use of the compounds of formulae I or II and compositions containing them for combating fleas is especially preferred.

The use of the compounds of formula formulae I or II and compositions containing them for combating ticks is a further preferred embodiment of the present invention.

The compounds of formulae I or II also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the compounds of formula I or II may be formulated as animal feeds, animal feed premixes, animal feed concentrates, pills, solutions, pastes, suspensions, drenches, gels, tablets, boluses and capsules. In addition, the compounds of formulae I or II may be administered to the animals in their drinking water. For oral administration, the dosage form chosen should provide the animal with 0.01 mg/kg to 100 mg/kg of animal body weight per day of the formulae I or II compound, preferably with 0.5 mg/kg to 100 mg/kg of animal body weight per day.

Alternatively, the compounds of formulae I or II may be administered to animals parenterally, for example, by intraruminal, intramuscular, intravenous or subcutaneous injection. The compounds of formulae I or II may be dispersed or dissolved in a physiologically acceptable carrier for subcutaneous injection. Alternatively, the compounds of formulae I or II may be formulated into an implant for subcutaneous administration. In addition the compounds of formula I or II) may be transdermally administered to animals. For parenteral administration, the dosage form chosen should provide the animal with 0.01 mg/kg to 100 mg/kg of animal body weight per day of the compounds of formulae I or II).

The compounds of formulae I or II may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5 000 ppm and preferably 1 ppm to 3 000 ppm of the compounds of formulae I or II. In addition, the compounds of formulae I or II may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointmentlike consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyitrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formulae I or II.

Generally, it is favorable to apply the compounds of formulae I or II in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formulae I or II against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formulae I or II are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formulae I or II in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formulae I or II. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds I or II or the compositions comprising them in the use form as pesticides with other pesticides frequently results in a broader pesticidal spectrum of action.

The following list M of pesticides together with which the compounds I or II the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aidicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-, yfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacioprid, thiamethoxam, nitenpyram, nicotine, spinosad (allosteric agonist), thiacioprid, thiocyclam, thiosultap-sodium and AKD1022.

M.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula M6.1

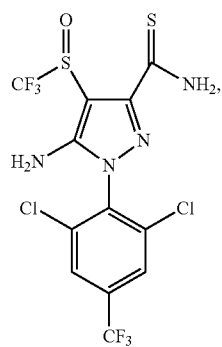

(M<sup>6.1</sup>)

M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonists: amitraz;

M.21. Ryanodine receptor modulators: flubendiamide;

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoximine compounds M22.1,

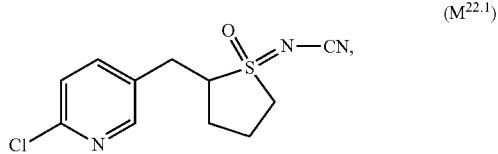 [SMILES: N#CN=S1(=O)CCCC1Cc1ccc(Cl)nc1]

(M<sup>22.1</sup>)

M22.2,

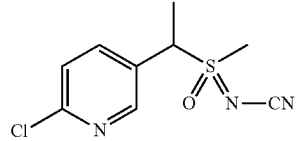

(M<sup>22.2</sup>)

or M22.3,

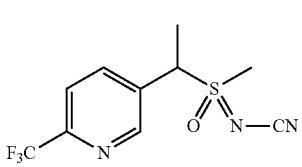

(M<sup>22.3</sup>)

pyrimidinyl alkynylether compounds M22.4 or thiadiazolyl alkynylether compounds M22.5,

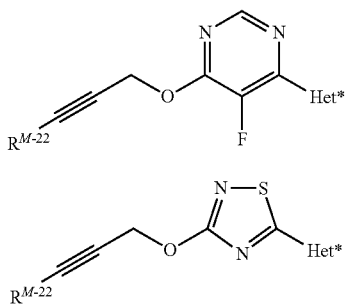

wherein RM-22 is methyl or ethyl and Het* is 3,3-dimethylpyrrolidin-1-yl, 3-methylpiperidin-1-yl, 3,5-dimethylpiperidin-1-yl, 3-trifluormethylpiperidin-1-yl, hexahydroazepin-1-yl, 2,6-dimethylhexahydroazepin-1-yl or 2,6-dimethylmorpholin-4-yl;

M.23. N—R'-2,2-dihalo-1-R''cyclo-propanecarboxamide-2-(2,6-dichloro-α,α,α-tri-fluoro-ptolyl)hydrazone or N—R'-2,2-di(R''')propionamide-2-(2,6-dichloro-α,α,α-trifluoro-p-tolyl)hydrazone, wherein R' is methyl or ethyl, halo is chloro or bromo, R'' is hydrogen or methyl and R''' is methyl or ethyl;

M.24. Anthranilamides: chloranthraniliprole, the compound of formula M24.1

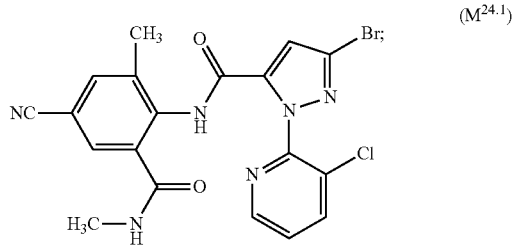 [SMILES: CNC(=O)c1cc(C#N)cc(C)c1NC(=O)c1cc(Br)nn1-c1ncccc1Cl]

M.25. Malononitrile compounds: $CF_2HCF_2CF_2CF_2CH_2C(CN)_2CH_2CH_2CF_3$, (2-(2,2,3,3,4,4,5,5-octafluoropentyl)-2-(3,3,3-trifluoro-propyl)malononitrile), $CF_3(CH_2)_2C(CN)_2CH_2(CF_2)_5CF_2H$, (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2(CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2CH_2(CF_2)_3CF_2H$ (2,2-Bis(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5,5-Nonafluoro-pentyl)-2-(3,3,3-trifluoro-propyl)-malononitrile), $CF_3(CF_2)_2CH_2C(CN)_2CH_2(CF_2)_3CF_2H$ (2-(2,2,3,3,4,4,4-Heptafluoro-butyl)-2-(2,2,3,3,4,4,5,5-octafluoro-pentyl)-malononitrile), $CF_3CF_2CH_2C(CN)_2CH_2(CF_2)_3CF_2H$ (2-(2,2,3,3,4,4,5,5-Octafluoro-pentyl)-2-(2,2,3,3,3-pentafluoro-propyl)-malononitrile), $CF_2HCF_2CF_2CF_2CH_2C(CN)_2CH_2CH_2CF_2CF_3$ (2-(2,2,3,3,4,4,5,5-octafluoropentyl)-2-(3,3,4,4,4-pentafluorobutyl)-malonodinitrile), $CF_3(CH_2)_2C(CN)_2CH_2(CF_2)_3CF_2H$ (2-(2,2,3,3,4,4,5,5-octafluoropentyl)-2-(3,3,3-trifluoro-butyl)-malononitrile);

M.26. Microbial disruptors: *Bacillus thuringiensis* subsp. *Israelensi, Bacillus sphaericus, Bacillus thuringiensis* subsp. *Aizawai, Bacillus thuringiensis* subsp. *Kurstaki, Bacillus thuringiensis* subsp. *Tenebrionis;*

The commercially available compounds of the group M may be found in The Pesticide Manual, 13th Edition, British Crop Protection Council (2003) among other publications.

Thioamides of formula M6.1 and their preparation have been described in WO 98/28279. Lepimectin is known from Agro Project, PJB Publications Ltd, November 2004. Benciothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Anthranilamide derivatives of formula M24.1 have been described in WO 01/70671, WO 04/067528 and WO 05/118552. Cyflumetofen and its preparation have been described in WO 04/080180. The aminoquinazolinone compound pyrifluquinazon has been described in EP A 109 7932. Suffoximine derivatives of formulae M22.1, M22.2 or M22.3 or in analogy thereof and their preparation methods have been described in WO 2006/060029. The alkynylether compounds M22.4 and M22.5 are described e.g. in JP 2006131529. Organic sulfur compounds have been described in WO 2007060839. The malononitrile compounds have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, dinicona-zole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinciozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpicionil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifen-phos, ethaboxam, fenhexamid, fentin-acetate, fenoxanil, ferimzone, fluazinam, fosetyl, fosetylaluminum, iprovalicarb, hexachlorobenzene, metrafenon, pencycuron, propamocarb, phthalide, tolociofos-methyl, quintozene, zoxamid, strobilurins such as azoxystrobin, dimoxystrobin, fluoxastrobin, kresoxim-methyl, me-tominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the present compound(s) I or II or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formulae I or II. As such, the application may be carried out before or after the infection of the locus, growing crops, or harvested crops by the pest.

"Locus" means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formulae I or II and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formulae I and II can also be applied preventively to places at which occurrence of the pests is expected.

The compounds of formulae I or II may also be used to protect growing plants from attack or infestation by pests by contacting the plant with a pesticidally effective amount of compounds of formula I or II. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the treatment of seed, the application rates of the active ingredients are generally from 0.1 g to 10 kg per 100 kg of seed, preferably from 1 g to 5 kg per 100 kg of seed, in particular from 1 g to 200 g per 100 kg of seed.

The present invention is now illustrated in further detail by the following examples.

I. PREPARATION EXAMPLES

The procedure described in the following synthesis examples was used to prepare further compounds of the formula I by appropriate modification of the starting material. The resulting compounds, together with physical data, are listed below in tables I and II.

Products were characterized by HPLC (High Performance Liquid Chromatography Mass Spectrometry). HPLC was carried out using an analytic RP-18 column (Chromolith Speed ROD from Merck KgaA, Germany) which was operated at 40° C. Acetonitrile with 0.1% by volume of a trifluoroacetic acid/water mixture and 0.1% by volume of trifluoroacetic acid served as mobile phase; flow rate: 1.8 mL/min and injection volume: 2 µl.

Example 13

1-methyl-3-trifluoromethyl-1H-pyrazole-4-carboxylic acid pyridin-3-ylamide 2.5 g (12.9 mmol) of 1-methyl-3-trifluoromethyl-1H-pyrazole-4-carboxylic acid in 25 mL of N,N-dimethylformanid (DMF) and 2.1 g (12.9 mmol) of N,N'-carbonyl diimidazole (CDI) were stirred at ambient temperature for 1 hour prior to addition of 1.2 g (12.9 mmol) of 3-aminopyridine. After three days of stirring the solvent was evaporated, the residue dissolved in dichloromethane, washed twice with a saturated solution of $NaHCO_3$ and water. The combined organic phases were evaporated and the crude product was purified by flash column chromatography (silica using dichloromethane/methanol=95/5) to give 1.33 g (48%) of the title compound.

Example 29

1-Methyl-3-trifluoromethyl-1H-pyrazole-4-carboxylic acid methyl-pyridin-3-yl-amide 1.0 g (3.7 mmol) of 1-methyl-3-trifluoromethyl-1H-pyrazole-4-carboxylic acid pyridin-3-yl-amide from example 13 in 10 mL of tetrahydrofuran (THF) and 3.7 g (11.1 mmol) of cesium carbonate were stirred at ambient temperature and 790 mg (5.55 mmol) of methyl iodide were added to the mixture. After two days of stirring the suspension was filtered, the solvent evaporated and the crude product was purified by flash column chromatography (silica using cyclohexane/ethyl acetate) to give 327 mg (31%) of the methylated amide.

TABLE I

Compounds of formula I (I)

| Ex. | A | $R^1$ | $R^2$ | $R^3$ | Physico-chemical data r.t. [min] |
|---|---|---|---|---|---|
| 1 | 1-methyl-1H-pyrazol-3-yl | H | H | H | n.d. |
| 2 | 1-(2,3-dichlorophenoxymethyl)-1H-pyrazol-3-yl | H | H | H | 2.461 |
| 3 | 2,5-dimethyl-2H-pyrazol-3-yl | H | H | H | 1.320 |
| 4 | 4-chloro-2,5-dimethyl-2H-pyrazol-3-yl | H | H | H | 1.543 |
| 5 | 5-chloro-1-methyl-1H-pyrazol-3-yl | H | H | H | 1.499 |
| 6 | 1-methyl-5-trifluoromethyl-1H-pyrazol-3-yl | H | H | H | 1.779 |
| 7 | 4-chloro-1-methyl-1H-pyrazol-3-yl | H | H | H | 1.353 |
| 8 | 1-methyl-5-phenyl-1H-pyrazol-3-yl | H | H | H | 2.124 |
| 9 | 2-methyl-5-phenyl-2H-pyrazol-3-yl | H | H | H | 2.193 |
| 10 | 1,5-dimethyl-1H-pyrazol-3-yl | H | H | H | 1.311 |
| 11 | 2-methyl-5-trifluoromethyl-2H-pyrazol-3-yl | H | H | H | 1.954 |
| 12 | 2-methyl-2H-pyrazol-3-yl | H | H | H | 1.125 |
| 13 | 1-methyl-3-trifluoromethyl-1H-pyrazol-4-yl | H | H | H | 1.548 |
| 14 | 3-difluoromethyl-1-methyl-1H-pyrazol-4-yl | H | H | H | 1.295 |
| 15 | 1-(6-chloropyridin-2-yl)-5-trifluoromethyl-1H-pyrazol-4-yl | H | H | H | 2.273 |
| 16 | 1-benzyl-5-trifluoromethyl-1H-pyrazol-4-yl | H | H | H | 2.290 |
| 17 | 1-ethyl-3-trifluoromethyl-1H-pyrazol-4-yl | H | H | H | 1.771 |
| 18 | 1-ethyl-5-trifluoromethyl-1H-pyrazol-4-yl | H | H | H | 1.704 |
| 19 | 1-allyl-3-trifluoromethyl-1H-pyrazol-4-yl | H | H | H | 2.187 |
| 20 | 5-difluoromethyl-1-methyl-1H-pyrazol-4-yl | H | H | H | 1.588 |
| 21 | 5-cyano-1-(2,4-dichlorophenyl)-1H-pyrazol-4-yl | H | H | H | 2.475 |
| 22 | 5-trifluoromethyl-1-(4-chlorophenyl)-1H-pyrazol-4-yl | H | H | H | 2.517 |
| 23 | 5-trifluoromethyl-1-phenyl-1H-pyrazol-4-yl | H | H | H | 2.185 |
| 24 | 1-(2,4-dichlorophenyl)-5-trifluoromethyl-1H-pyrazol-4-yl | H | H | H | 2.587 |
| 25 | 1-(4-fluorophenyl)-5-methyl-1H-pyrazol-4-yl | H | H | H | 1.834 |
| 26 | 1-(2,2,2-trifluoroethyl)-5-trifluoromethyl-1H-pyrazol-4-yl | H | H | H | 1.980 |
| 27 | 5-chloro-1-methyl-3-trifluoromethyl-1H-pyrazol-4-yl | H | H | H | 1.651 |
| 28 | 1-methyl-3-trifluoromethyl-1H-pyrazol-4-yl | benzyl | H | H | 2.457 |
| 29 | 1-methyl-3-trifluoromethyl-1H-pyrazol-4-yl | $CH_3$ | H | H | 1.504 |
| 30 | 1-tert-butyl-5-trifluoromethyl-1H-pyrazol-4-yl | H | H | H | 2.197 |
| 31 | 1-(4-nitrophenyl)-5-trifluoromethyl-1H-pyrazol-4-yl | H | H | H | 2.269 |

TABLE I-continued

Compounds of formula I (I)

| Ex. | A | R¹ | R² | R³ | Physico-chemical data r.t. [min] |
|---|---|---|---|---|---|
| 32 | 1-(5-chloropyridin-2-yl)-5-trifluoromethyl-1H-pyrazol-4-yl | H | H | H | 2.339 |
| 33 | 1-methyl-3-trifluoromethyl-1H-pyrazol-4-yl | H | H | CH₃ | 1.793 |
| 34 | 1-methyl-3-trifluoromethyl-1H-pyrazol-4-yl | H | H | Cl | 2.444 |
| 35 | 5-difluoromethyl-1-methyl-1H-pyrazol-4-yl | C₂H₅ | H | H | 1.645 |
| 36 | 5-difluoromethyl-1-methyl-1H-pyrazol4-yl | CH₃ | H | H | 1.487 |
| 37 | 1-methyl-3-trifluoromethyl-1H-pyrazol-4-yl | H | H | CF₃ | 2.844 |
| 38 | 1-methyl-3-trifluoromethyl-1H-pyrazol-4-yl | H | H | F | 2.194 |
| 39 | 1-isopropyl-3-trifluoromethyl-1H-pyrazol-4-yl | H | H | H | 2.041 |
| 40 | 1-isobutyl-3-trifluoromethyl-1H-pyrazol-4-yl | H | H | H | 2.271 |
| 41 | 1-methyl-3-trifluoromethyl-1H-pyrazol-4-yl | H | CH₃ | H | 1.597 |
| 42 | 5-chloro-1,3-dimethyl-1H-pyrazol-4-yl | H | H | H | 1.385 |
| 43 | 1-propyl-3-trifluoromethyl-1H-pyrazol-4-yl | H | H | H | 2.040 |
| 44 | 1-methyl-3-ethoxy-1H-pyrazol-4-yl | H | H | H | 1.550 |
| 45 | 1-propyl-5-trifluoromethyl-1H-pyrazol-4-yl | H | H | H | 2.101 |
| 46 | 5-trifluoromethyl-1H-pyrazol-4-yl | H | H | H | 1.410 |
| 47 | 3-cyclopropyl-1-methyl-1H-pyrazol-4-yl | H | H | H | 1.491 |
| 48 | 1-(2,2,2-trifluoroethyl)-5-trifluoromethyl-1H-pyrazol-4-yl | CH₃ | H | H | 2.032 |
| 49 | 1-(2,2,2-trifluoroethyl)-5-trifluoromethyl-1H-pyrazol-4-yl | C₂H₅ | H | H | 2.281 |
| 50 | 1-(2,2,2-trifluoroethyl)-5-trifluoromethyl-1H-pyrazol-4-yl | iso-butyl | H | H | 2.767 |
| 51 | 1-methyl-3-trifluoromethyl-1H-pyrazol-4-yl | H | Cl | H | 1.868 |
| 52 | 1-methyl-3-trifluoromethyl-1H-pyrazol-4-yl | H | OCH₃ | H | 1.652 |
| 53 | 3-methoxy-1-methyl-1H-pyrazol-4-yl | H | H | H | 1.333 |
| 54 | 5-bromo-2-(3-chloropyridin-2-yl)-2H-pyrazol-3-yl | | H | H | 1,92 |
| 55 | 2-(3-chloropyridin-2-yl)-5-trifluoromethyl-2H-pyrazol-3-yl | H | H | H | 2.283 |
| 56 | 3-trifluoromethyl-1-(4-chlorophenyl)-1H-pyrazol-4-yl | H | H | H | 2.548 |
| 57 | 1-(4-methoxyphenyl)-5-methyl-1H-pyrazol-4-yl | H | H | H | 2.005 |
| 58 | 5-phenyl-1H-pyrazol-4-yl | H | H | H | 1.504 |
| 59 | 1-ethyl-5-methyl-1H-pyrazol-4-yl | H | H | H | 1.426 |
| 60 | 1-methyl-5-phenyl-1H-pyrazol-4-yl | H | H | H | 1.751 |
| 61 | 1,3-dimethyl-1H-pyrazol-4-yl | H | H | H | 1.219 |
| 62 | 2-methyl-5-tert.-butyl-2H-pyrazol-3-yl | H | H | H | 1.78 |
| 63 | 2-methyl-4-chloro-2H-pyrazol-3-yl | H | H | H | 1.49 |
| 64 | 2-(3-chloropyridin-3-yl)-5-trifluoromethyl-2H-pyrazol-3-yl | H | H | H | 2.28 |
| 65 | 4-isopropyl-1-methyl-1H-pyrazol-3-yl | H | H | H | 1.81 |
| 66 | 5-isopropyl-2-methyl-2H-pyrazol-3-yl | H | H | H | 1.56 |
| 67 | 5-ethyl-2-methyl-2H-pyrazol-3-yl | H | H | H | 1.53 |
| 68 | 4,5-dimethyl-2-methyl-2H-pyrazol-3-yl | H | H | H | 1.42 |
| 69 | 2-methyl-5-n-propyl-2H-pyrazol-3-yl | H | H | H | 1.76 | r.t. retention time  
n.d. not determined

TABLE II

Compounds of formula I.A1

(I.A1)

| Ex. | $R^{41}$ | $R^{51}$ | $R^{61}$ | $R^1$ | $R^2$ | $R^3$ | r.t. [min]; m.p. [° C.] |
|---|---|---|---|---|---|---|---|
| 70 | H | CH₃ | CH₃ | H | H | H | 1.27; n.d. |
| 71 | phenyl | H | CH₃ | H | H | H | 1.80; n.d. |
| 72 | CH₃ | H | C₂H₅ | H | H | H | 1.47; n.d. |
| 73 | H | CF₃ | 4-chlorophenyl | H | H | H | 2.59; n.d. |
| 74 | phenyl | H | H | H | H | H | 1.50; n.d. |
| 75 | CH₃ | H | 4-methoxy-phenyl | H | H | H | 2.01; n.d. |
| 76 | 4-fluoro-phenyl | H | H | H | H | H | 1.57; n.d. |
| 77 | 2-thienyl | H | H | H | H | H | 1.47; n.d. |
| 78 | F | CF₃ | CH₃ | H | H | H | 1.63; n.d. |
| 79 | n-propyl | H | 4-chlorophenyl | H | H | H | 2.53; n.d. |
| 80 | CHF₂ | H | 1-methyl-1,3,4-triazin-2-yl | H | H | H | n.d.; 130 |
| 81 | H | H | 4-chlorobenzyl | H | H | H | n.d.; 218 |
| 82 | H | H | benzyl | H | H | H | n.d.; 165 |
| 83 | Cl | H | CH₃ | H | H | H | n.d.; 186 |
| 84 | H | CH₃ | phenyl | H | H | H | 2.08; n.d. |
| 85 | CHF₂ | H | 4-(trifluoro-methyl)phenyl | H | H | H | 2.75; n.d. |
| 86 | CHF₂ | H | 4-chlorophenyl | H | H | H | 2.55; n.d. |
| 87 | H | H | H | H | H | H | 0.54; n.d. |
| 88 | CHF₂ | H | 4-(methyl-sulfonyl)-phenyl | H | H | H | 1.89; n.d. |
| 89 | cyclopropyl | H | CH₃ | H | H | H | 1.41; n.d. |
| 90 | isopropyl | H | CH₃ | H | H | H | 1.65; n.d. |
| 91 | 2-methyl-propyl | H | CH₃ | H | H | H | 2.71; n.d. |
| 92 | CHF₂ | H | 4-(heptafluoro-isopropyl)-phenyl | H | H | H | 3.12; n.d. |
| 93 | CHF₂ | H | 4-(trifluoro-methylthio)-phenyl | H | H | H | 2.94; n.d. |
| 94 | CHF₂ | H | 4-fluorophenyl | H | H | H | 2.39; n.d. |
| 95 | CHF₂ | H | 4-(trifluoro-methoxy)-phenyl | H | H | H | 2.73; n.d. |
| 96 | C(=O)NH₂ | H | CH₃ | H | H | H | n.d.; 230 |
| 97 | H | H | isopropyl | H | H | H | n.d.; 174 |
| 98 | H | H | 2-methylpropyl | H | H | H | n.d.; 143 |
| 99 | H | H | 2,2-difluoro-ethyl | H | H | H | n.d.; 152 |
| 100 | H | CF₃ | CH₃ | H | H | H | 1.69; n.d. (as N-oxide) |
| 101 | CHF₂ | H | 2,6-dichloro-4-(trifluoro-methyl)phenyl | H | H | H | 2.91; n.d. |
| 102 | H | H | ethyl | H | H | H | n.d.; 126 |
| 103 | H | H | 2,2,2-trifluoroethyl | H | H | H | n.d.; 191 |
| 104 | H | CF₃ | 4-(trifluoro-methyl)-thiazolin-2-yl | H | H | H | n.d.; 194 |
| 105 | H | H | pyridin-2-yl | H | H | H | n.d.; 244 |
| 106 | H | H | phenyl | H | H | H | n.d.; 241 |
| 107 | H | H | CH₃ | H | H | H | n.d.; 180 |
| 108 | H | H | n-propyl | H | H | H | n.d.; 119 |
| 109 | CF₃ | H | CH₃ | H | H | H | 1.51; n.d. |
| 110 | H | OCHF₂ | CH₃ | H | H | H | 1.43; n.d. |
| 111 | H | CF₃ | benzyl | H | H | H | 2.34; n.d. |
| 112 | H | CF₂Cl | CH₃ | H | H | H | 1.69; n.d. |
| 113 | H | H | 4-fluorophenyl | H | H | H | n.d.; 235 |

TABLE II-continued

Compounds of formula I.A1

(I.A1)

| Ex. | R$^{41}$ | R$^{51}$ | R$^{61}$ | R$^{1}$ | R$^{2}$ | R$^{3}$ | r.t. [min]; m.p. [° C.] |
|---|---|---|---|---|---|---|---|
| 114 | H | H | (4-nitro-pyrazol-1-yl)-methyl | H | H | H | n.d.; 227 |
| 115 | CH$_3$ | H | 1-methyl-1,3,4-triazin-2-yl | H | H | H | n.d.; 206 |
| 116 | CH$_3$ | H | thiazol-2-yl | H | H | H | n.d.; 205 |
| 117 | CHF$_2$ | H | 4-(trifluoro-methyl)thiazol-2-yl | H | H | H | n.d.; 171 |
| 118 | CH$_3$ | H | 4-(trifluoro-methyl)thiazol-2-yl | H | H | H | n.d.; 240 |
| 119 | H | H | cyclopropyl | H | H | H | n.d.; 145 |
| 120 | isopropyl | H | phenyl | H | H | H | 2.32; n.d. |
| 121 | CH$_3$ | H | 4,5-dimethyl-thiazol-2-yl | H | H | H | n.d.; 235 |
| 122 | CHF$_2$ | H | 4,5-dimethyl-thiazol-2-yl | H | H | H | n.d.; 182 |
| 123 | Cl | H | phenyl | H | H | H | n.d.; 171 |
| 124 | I | H | 4-fluorophenyl | H | H | H | n.d.; 188 |
| 125 | H | 2-fluoro-ethyl | CH$_3$ | H | H | H | 1.22; n.d. |
| 126 | H | CF$_3$ | CH$_3$ | cyclopropyl-methyl | H | H | 2.13; n.d. |
| 127 | H | CF$_3$ | CH$_3$ | ethyl | H | H | 1.73; n.d. |
| 128 | CHF$_2$ | H | 3-methyl-3H-1,3,4-triazin-2-yl | H | H | H | 1.18; n.d. |
| 129 | H | CF$_3$ | CH$_3$ | n-propyl | H | H | 2.06; n.d. |
| 130 | H | CF$_3$ | CH$_3$ | iso-propyl | H | H | 2.00; n.d. |
| 131 | H | CF$_3$ | CH$_3$ | (1-methyl-3-(trifluoro-methyl)-pyrazol-4-yl)carbonyl | H | H | 186; n.d. |
| 132 | H | CF$_3$ | CH$_3$ | tert.-butyloxy-carbonyl | H | H | n.d.; n.d. |
| 133 | H | CF$_3$ | CH$_3$ | tert.-butyl-carbonyl | H | H | 2.83; n.d. |
| 134 | H | CF$_3$ | CH$_3$ | acetyl | H | H | n.d.; 143 |
| 135 | CHF$_2$ | H | 2,4-difluorophenyl | H | H | H | 2.38; n.d. |
| 136 | H | CF$_3$ | CH$_3$ | tosyl | H | H | 2.98; n.d. |
| 137 | CHF$_2$ | H | 3,5-dichlorophenyl | H | H | H | 2.77; n.d. |
| 138 | CHF$_2$ | H | 4-tolyl | H | H | H | 2.43; n.d. |
| 139 | H | CF$_3$ | CH$_3$ | CH$_2$—CN | H | H | 1.88; n.d. |
| 140 | H | H | n-heptyl | H | H | H | 2.63; n.d. |
| 141 | H | CF$_3$ | CH$_3$ | 2-propynyl | H | H | 1.89; n.d. |
| 142 | CH$_3$ | H | 4-chlorophenyl | H | H | H | 2.26; n.d. |
| 143 | ethyl | H | 4-chlorophenyl | H | H | H | 2.42; n.d. |
| 144 | ethyl | H | 4-nitrophenyl | H | H | H | 2.26; n.d. |
| 145 | ethyl | H | 4-(trifluoro-methyl)phenyl | H | H | H | 2.69; n.d. |
| 146 | ethyl | H | 4-fluorophenyl | H | H | H | 2.26; n.d. |
| 147 | CHF$_2$ | H | 3-(trifluoro-methyl)phenyl | H | H | H | 2.61; n.d. |
| 148 | CHF$_2$ | H | 2-chlorophenyl | H | H | H | 2.24; n.d. |
| 149 | CHF$_2$ | H | 2-(trifluoro-methyl)phenyl | H | H | H | 2.38; n.d. |

TABLE II-continued

Compounds of formula I.A1

(I.A1)

| Ex. | $R^{41}$ | $R^{51}$ | $R^{61}$ | $R^1$ | $R^2$ | $R^3$ | r.t. [min]; m.p. [° C.] |
|---|---|---|---|---|---|---|---|
| 150 | $CHF_2$ | H | 2-methoxyphenyl | H | H | H | 2.12; n.d. |
| 151 | $CHF_2$ | H | 3-chloro-4-fluorophenyl | H | H | H | 2.54; n.d. |
| 152 | $CHF_2$ | H | 4-tert.-butylphenyl | H | H | H | 2.95; n.d. |
| 153 | $CHF_2$ | H | 3-nitrophenyl | H | H | H | 2.25; n.d. |
| 154 | $CHF_2$ | H | 3,4-dichlorophenyl | H | H | H | 2.75; n.d. |
| 155 | $CHF_2$ | H | 2,4-dichlorophenyl | H | H | H | 2.62; n.d. |
| 156 | $CHF_2$ | H | 2-tolyl | H | H | H | 2.34; n.d. |
| 157 | $CHF_2$ | H | 3-chlorophenyl | H | H | H | 2.46; n.d. |
| 158 | $CHF_2$ | H | 3-tolyl | H | H | H | 2.42; n.d. |
| 159 | $CHF_2$ | H | 4-chloro-2-fluorophenyl | H | H | H | 2.57; n.d. |
| 160 | $CHF_2$ | H | 2,4,6-trichlorophenyl | H | H | H | 2.79; n.d. |
| 161 | $CHF_2$ | H | 2,3,4-trichlorophenyl | H | H | H | 2.85; n.d. |
| 162 | $CHF_2$ | H | 2,6-difluorophenyl | H | H | H | 2.29; n.d. |
| 163 | H | $CF_3$ | $CH_3$ | ethoxycarbonyl | H | H | n.d.; 104 |
| 164 | H | $CF_3$ | $CH_3$ | ethoxymethyl | H | H | 2.19; n.d. |
| 165 | $CH_3$ | H | 4-fluorophenyl | H | H | H | 2.17; n.d.; (as N-oxide) |
| 166 | $CH_3$ | H | 4-(trifluoromethyl)phenyl | H | H | H | 2.50; n.d. |
| 167 | $CHF_2$ | H | $CH_3$ | H | H | H | n.d.; 172; (as hydrochloride) |
| 168 | $CF_3$ | H | 2,2,2-trifluoroethyl | acetyl | H | H | 2.52; n.d. |
| 169 | $CF_3$ | H | 2,2,2-trifluoroethyl | $CH_3$ | H | H | n.d.; 131; (as N-oxide) |
| 170 | H | $CHF_2$ | $CH_3$ | H | H | H | 1.67; n.d.; (as N-oxide) |
| 171 | H | $CHF_2$ | 4-nitrophenyl | H | H | H | 2.46; n.d. |
| 172 | $CH_3$ | H | 2,2,2-trifluoroethyl | H | H | H | 1.65; n.d. |
| 173 | $CH_3$ | H | 2,2,2-trifluoroethyl | $CH_3$ | H | H | 1.79; n.d. |
| 174 | $CF_3$ | H | $CH_3$ | $CH_3$ | H | H | 1.44; n.d. |
| 175 | $CHF_2$ | H | 2,2,2-trifluoroethyl | H | H | H | 2.07; n.d. |
| 176 | $CHF_2$ | H | 2,2,2-trifluoroethyl | $CH_3$ | H | H | 1.82; n.d. |
| 177 | H | H | $CH_3$ | $CH_3$ | H | H | 0.85; n.d. |
| 178 | $CH_3$ | H | $CH_3$ | $CH_3$ | H | H | 0.99; n.d. |
| 179 | $CH_3$ | H | $CH_3$ | H | H | H | 1.32; n.d. |
| 180 | $CH_3$ | H | ethyl | $CH_3$ | H | H | 1.22; n.d. |
| 181 | H | $CHF_2$ | ethyl | H | H | H | 2.00; n.d. |
| 182 | H | $CHF_2$ | ethyl | $CH_3$ | H | H | 1.39; n.d. |
| 183 | H | $CF_3$ | ethyl | $CH_3$ | H | H | 1.77; n.d. |
| 184 | ethyl | H | ethyl | H | H | H | 1.59; n.d. |
| 185 | ethyl | H | ethyl | $CH_3$ | H | H | 1.49; n.d. |
| 186 | $CF_3$ | H | ethyl | $CH_3$ | H | H | 1.89; n.d. |
| 187 | H | H | ethyl | $CH_3$ | H | H | 1.11; n.d. |
| 188 | $CHF_2$ | H | $CHF_2$ | H | H | H | 1.73; n.d. |
| 189 | $CHF_2$ | H | $CHF_2$ | $CH_3$ | H | H | 1.66; n.d. |
| 190 | $CF_3$ | H | $CHF_2$ | H | H | H | 2.00; n.d. |

TABLE II-continued

Compounds of formula I.A1

(I.A1)

| Ex. | $R^{41}$ | $R^{51}$ | $R^{61}$ | $R^1$ | $R^2$ | $R^3$ | r.t. [min]; m.p. [° C.] |
|---|---|---|---|---|---|---|---|
| 191 | $CF_3$ | H | $CHF_2$ | $CH_3$ | H | H | 2.05; n.d. |
| 192 | H | CF3 | $CHF_2$ | H | H | H | 1.90; n.d. |
| 193 | H | $CF_3$ | $CHF_2$ | $CH_2$—CN | H | H | 2.43; n.d. |
| 194 | H | $CHF_2$ | $CHF_2$ | H | H | H | 1.82; n.d. |
| 195 | H | $CF_3$ | $CHF_2$ | $CH_3$ | H | H | 1.77; n.d. |
| 196 | H | $CF_3$ | $CH_3$ | H | H | H | 1.49; n.d.; (as hydrochloride) |
| 197 | $CHF_2$ | H | $CH_3$ | H | H | H | 1.46; n.d.; (as hydrochloride) |
| 198 | $CF_3$ | H | 2,2,2-trifluoro-ethyl | H | H | H | 1.93; n.d.; (as hydrochloride) |
| 199 | $CF_3$ | H | 4-nitrophenyl | H | H | H | 2.23; n.d.; (as hydrochloride) |
| 200 | H | H | isopropyl | H | H | H | 1.36; n.d.; (as hydrochloride) |
| 201 | $CHF_2$ | H | 3-methyl-3H-1,3,4-triazin-2-yl | H | H | H | 1.11; n.d.; (as hydrochloride) |
| 202 | H | $CF_3$ | $CH_3$ | n-propyl | H | H | 1.98; n.d.; (as hydrochloride) |
| 203 | $CH_3$ | H | 2,2,2-trifluoro-ethyl | $CH_3$ | H | H | 1.43; n.d.; (as hydrochloride) |
| 204 | H | H | 2,2-difluoro-ethyl | $CH_3$ | H | H | 1.10; n.d. |
| 205 | H | H | $CF_3$ | H | H | H | n.d.; 208 |
| 206 | H | $CHF_2$ | ethyl | $CH_2$—CN | H | H | 1.75; n.d. |
| 207 | $CF_3$ | H | $CHF_2$ | $CH_2$—CN | H | H | 2.47; n.d. |
| 208 | $CH_3$ | H | $CHF_2$ | H | H | H | 1.50; n.d. |
| 209 | H | $CH_3$ | $CHF_2$ | H | H | H | 1.54; n.d. |
| 210 | $CHF_2$ | H | $CHF_2$ | CN | H | H | 2.10; n.d. |
| 211 | $CF_3$ | H | $CH_3$ | $CH_2$—CN | H | H | 2.02; n.d. |
| 212 | $CH_3$ | H | $CH_3$ | $CH_2$—CN | H | H | 1.47; n.d. |
| 213 | H | H | $CHF_2$ | H | H | H | n.d.; 174 |
| 214 | $CHF_2$ | H | $CF_3$ | $CH_2$—CN | H | H | 2.21; n.d. |
| 215 | $CH_3$ | H | 2,2,2-trifluoro-ethyl | $CH_2$—CN | H | H | 1.76; n.d. |
| 216 | $CHF_2$ | H | $CH_3$ | $CH_2$—CN | H | H | 2.29; n.d. |
| 217 | $CF_3$ | H | ethyl | $CH_2$—CN | H | H | 2.04; n.d. |
| 218 | ethyl | H | ethyl | $CH_2$—CN | H | H | 1.70; n.d. |
| 219 | H | H | 2,2,2-trifluoro-ethyl | $CH_3$ | H | H | n.d.; 90 |
| 220 | $CH_3$ | H | $CHF_2$ | $CH_3$ | H | H | 1.35; n.d. |
| 221 | $CH_3$ | H | $CHF_2$ | $CH_2$—CN | H | H | 1.72; n.d. |
| 222 | H | H | $CHF_2$ | $CH_3$ | H | H | 1.11; n.d. |
| 223 | H | H | $CH_3$ | $CH_2$—CN | H | H | 1.53; n.d. |
| 224 | H | H | ethyl | $CH_2$—CN | H | H | 1.34; n.d. |
| 225 | $CF_3$ | H | 4-(trifluoro-methyl)phenyl | H | H | H | 2.68; n.d. |
| 226 | $CF_3$ | H | 4-methoxy-phenyl | H | H | H | 2.25; n.d. |
| 227 | $CF_3$ | H | 4-(methyl-sulfonyl)-phenyl | H | H | H | 1.85; n.d. |
| 228 | $CF_3$ | H | 4-fluorophenyl | H | H | H | 2.26; n.d. |
| 229 | H | $CH_3$ | $CHF_2$ | $CH_3$ | H | H | 1.40; n.d. |
| 230 | H | $CH_3$ | $CHF_2$ | $CH_2$—CN | H | H | 1.76; n.d. |

TABLE II-continued

Compounds of formula I.A1

(I.A1)

[Structure of formula I.A1 showing pyrazole-carboxamide with pyridine substituent, with R$^{51}$, R$^{41}$, R$^{61}$, R$^1$, R$^2$, R$^3$ positions]

| Ex. | R$^{41}$ | R$^{51}$ | R$^{61}$ | R$^1$ | R$^2$ | R$^3$ | r.t. [min]; m.p. [° C.] |
|---|---|---|---|---|---|---|---|
| 231 | CH$_3$ | H | 4-nitrophenyl | H | H | H | 2.04; n.d. |
| 232 | H | CF$_3$ | 2,2-difluoro-ethyl | H | H | H | 1.81; n.d. |
| 233 | H | H | CF$_3$ | CH$_3$ | H | H | 1.49; n.d. |
| 234 | H | CF$_3$ | 2,2-difluoro-ethyl | CH$_3$ | H | H | 1.76; n.d. |
| 235 | H | H | 2,2-difluoro-ethyl | CH$_2$—CN | H | H | 1.40; n.d. |
| 236 | H | H | 2,2,2-trifluoro-ethyl | CH$_2$—CN | H | H | 1.76; n.d. |
| 237 | CF$_3$ | H | 2,4-difluoro-phenyl | H | H | H | 2.32; n.d. |
| 238 | CF$_3$ | H | 4-tolyl | H | H | H | 2.50; n.d. |
| 239 | CF$_3$ | H | 3,5-dichloro-phenyl | H | H | H | 2.87; n.d. |
| 240 | H | CHF$_2$ | CH$_3$ | CH$_2$—CN | H | H | 1.57; n.d. |
| 241 | H | CHF$_2$ | CH$_3$ | CH$_3$ | H | H | 1.29; n.d. | r.t. retention time
m.p. melting point
n.d. not determined

Furthermore compounds 242 and 243 have been prepared according to the methods outlined above.

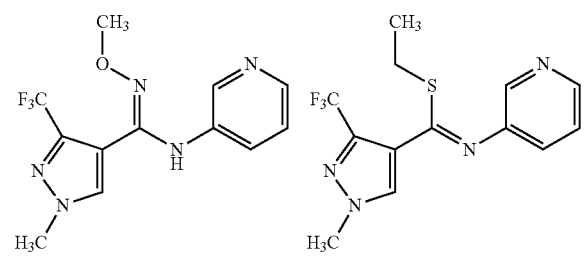

(242): r.t. = 1.77 min     (243): r.t. = 2.24 min

2. Evaluation of Pesticidal Activity:

II.1 Cotton Aphid (*Aphis Gossypii*, Mixed Life Stages)

The active compounds were formulated in 50:50 (vol:vol) acetone:water and 100 ppm Kinetica™ surfactant.

Cotton plants at the cotyledon stage (one plant per pot) were infested by placing a heavily infested leaf from the main colony on top of each cotyledon. The aphids were allowed to transfer to the host plant overnight, and the leaf used to transfer the aphids was removed. The cotyledons were dipped in the test solution and allowed to dry. After 5 days, mortality counts were made.

In this test, the compounds 1, 3, 5, 6, 10, 11, 13, 14, 15, 16, 17, 18, 19, 20, 21, 22, 23, 24, 25, 26, 28, 29, 30, 31, 32, 35, 36, 37, 38, 39, 40, 41, 43, 44, 45, 46, 47, 48, 49, 50 51, 62, 65, 66, 67, 69, 70, 71, 72, 73, 75, 80, 82, 83, 85, 86, 87, 88, 89, 91, 92, 93, 94, 95, 96. 97, 98, 99, 100, 102, 103, 104, 105, 107, 108, 109, 110, 115, 116, 118, 119, 120, 121, 122, 123, 124, 125, 126, 127, 128, 129, 130, 131, 132, 133, 134, 135, 136, 137, 138, 139, 141, 142, 143, 144, 145, 147, 148, 149, 150, 151, 154, 155, 156, 157, 158, 161, 163, 164, 165, 166, 167, 168, 169, 170, 172, 173, 174, 175, 176, 177, 178, 179, 180, 181, 182, 183, 184, 185, 186, 187, 188, 189, 190, 191, 192, 193, 194, 195, 196, 197, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 233, 242 and 243, respectively, at 300 ppm showed a mortality of at least 75% in comparison with untreated controls.

II.2 Green Peach Aphid (*Myzus persicae*, Mixed Life Stages)

The active compounds were formulated in 50:50 (vol:vol) acetone:water and 100 ppm Kinetica™ surfactant.

Pepper plants in the 2$^{nd}$ leaf-pair stage (variety 'California Wonder') were infested with approximately 40 laboratory-reared aphids by placing infested leaf sections on top of the test plants. The leaf sections were removed after 24 hr. The leaves of the intact plants were dipped into gradient solutions of the test compound and allowed to dry. Test plants were maintained under fluorescent light (24 hour photoperiod) at about 25° C. and 20-40% relative humidity. Aphid mortality on the treated plants, relative to mortality on check plants, was determined after 5 days.

In this test, compounds 1, 3, 5, 6, 10, 11, 13, 14, 15, 16, 17, 18, 19, 20, 21, 22, 23, 24, 25, 26, 27, 29, 30, 31, 32, 35, 36, 37, 39, 40, 41, 43, 45, 46, 47, 48, 49, 50, 62, 65, 66, 67, 69, 70, 71, 73, 75, 79, 80, 81, 82, 83, 85, 86, 87, 88, 89, 91, 92, 93, 94, 95, 96, 97, 98, 99, 100, 102, 103, 104, 105, 107, 108, 109, 110, 115, 116, 118, 119, 120, 121, 122, 123, 124, 125, 126, 127, 128, 129, 130, 131, 132, 133, 134, 135, 136, 137, 138, 139, 140, 141, 142, 143, 144, 145, 147, 148, 149, 150, 151, 154, 155, 156, 157, 158, 161, 163, 164, 165, 166, 167, 168, 169, 170, 172, 173, 174, 175, 176, 177, 178, 179, 180, 181, 182, 183, 184, 185, 186, 187, 188, 189, 190, 192, 193, 194, 195, 196, 197, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 233, 242 and 243, respectively, at 300 ppm showed a mortality of at least 50% in comparison with untreated controls.

II.3 Cowpea Aphid (Aphis Craccivora)

The active compounds were formulated in 50:50 (vol:vol) acetone:water. The test solution was prepared at the day of use.

Potted cowpea plants colonized with 100-150 aphids of various stages were sprayed after the pest population had been recorded. Population reduction was assesed after 24, 72, and 120 hours.

In this test, the compounds 1, 3, 5, 6, 7, 9, 10, 11, 13, 14, 15, 16, 17, 18, 19, 20, 21, 22, 23, 24, 25, 26, 28, 29, 30, 31, 33, 35, 36, 38, 39, 40, 43, 44, 45, 46, 47, 62, 65, 66, 67, 69, 70, 72, 73, 75, 79, 80, 81, 82, 83, 85, 86, 87, 88, 89, 90, 91, 92, 93, 94, 95, 97, 98, 99, 100, 102, 103, 104, 106, 107, 108, 109, 110, 113, 114, 115, 116, 117, 118, 119, 120, 121, 122, 123, 124, 132, 133, 134, 135, 136, 138, 139, 141, 142, 143, 144, 145, 147, 148, 149, 156, 157, 158, 161, 163, 164, 165, 166, 167, 168, 169, 170, 172, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 242 and 243 respectively, at 300 ppm showed a mortality of at least 75% in comparison with untreated controls.

II.4 Bean Aphid (*Aphis fabae*)

The active compounds were formulated in 50:50 (vol:vol) acetone:water and 100 ppm Kinetica™ surfactant.

Nasturtium plants grown in Metro mix in the $1^{st}$ leaf-pair stage (variety 'Mixed Jewel') were infested with approximately 2-30 laboratory-reared aphids by placing infested cut plants on top of the test plants. The cut plants were removed after 24 hr. Each plant was dipped into the test solution to provide complete coverage of the foliage, stem, protruding seed surface and surrounding cube surface and allowed to dry in the fume hood. The treated plants were kept at about 25° C. with continuous fluorescent light. Aphid mortality is determined after 3 days.

In this test, the compounds 13, 14, 18, 20, 29, 75, 80, 94, 116, 122, 123, 126, 127, 129, 135, 142, 143, 166 and 168, respectively, at 10 ppm showed a mortality of at least 90% in comparison with untreated controls.

II.5 Silverleaf Whitefly (*Bemisia argentifolii*, Adult)

The active compounds were formulated in 50:50 (vol:vol) acetone:water and 100 ppm Kinetica™ surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were colleted using an aspirator and an 0.6 cm, non-toxic Tygon® tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc). Test plants were maintained in the holding room at about 25° C. and 20-40% relative humidity for 3 days avoiding direct exposure to the fluorescent light (24 hour photoperiod) to prevent trapping of heat inside the cup. Mortality was assessed 3 days after treatment of the plants.

In this test, compounds 16, 18, 21, 26, 29, 35, 46, 48, 49, 50, 62, 73, 75, 80, 82, 83, 84, 89, 100, 102, 109, 133, 134, 163, 168, 173, 180, 212, 215 and 229, respectively, at 300 ppm showed a mortality of at least 50% in comparison with untreated controls.

II.6 Brown Planthopper (*Nilaparvata lugens*)

The active compounds were formulated as a 50:50 (vol:vol) acetone:water solution. Surfactant (Alkamuls EL 620) was added at the rate of 0.1% (vol/vol).

Rice seedlings were cleaned and washed 24 h before spraying. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds 36, 65, 176 and 195, respectively at 300 ppm showed a mortality of at least 50% in comparison with untreated controls.

II.7 Southern Armyworm (*Spodoptera eridania*, $2^{nd}$ Instar Larvae)

The active compounds were formulated in 50:50 (vol:vol) acetone:water and 100 ppm Kinetica™ surfactant.

A pair of first true leaves of Sieva lima bean was dipped in the test solution and allowed to dry. The leaf was then placed in a plastic perforated zip enclosure bag and ten $2^{nd}$ instar larvae were added. At 4 days, observations were made of mortality and reduced feeding.

In this test, compounds 48, 76, 77, 78, 79, 92, 98, 118, 155, 157, 158, 170, 173, 174, 175, 179, 189, 191, 196, 199, 201, 209, 213, 215, 218, 219, 220, 221, 223, 224, 228 and 233, respectively at 300 ppm showed a mortality of at least 50% in comparison with untreated controls.

II.8 Vetch Aphid (*Megoura viciae*)

The active compounds were formulated in 1:3 (vol:vol) DMSO:water with different concentrations of formulated compounds.

Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiterplates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds 3, 9, 11, 13, 14, 16, 17, 18, 19, 20, 21, 22, 23, 24, 25, 26, 28, 29, 62, 65, 66, 67, 69, 71, 72, 73, 75, 85, 87, 89, 91, 93, 94, 95, 96, 97, 98, 99, 100, 102, 103, 104, 107, 108, 109, 110, 112, 116, 117, 119, 120, 121, 122, 123, 124, 125, 126, 127, 128, 129, 130, 131, 132, 133, 134, 135, 136, 138, 140, 141, 142, 143, 144, 145, 147, 148, 149, 150, 152, 153, 154, 155, 156, 157, 158, 159, 161, 162, 163, 164, 165, 166, 167, 181, 182, 183, 184, 185, 186, 189, 190, 191, 193, 194, 195, 201, 202, 203, 204, 205, 206, 207, 210, 218, 220, 221, 225, 226, 227, 228, 230, 231, 232, 234, 242 and 243, respectively at a concentration of the test solution of 2500 mg/L showed a mortality of at least 80%.

11.9 Boll weevil (*Anthonomus grandis*)

The compounds were formulated in 75:25 (vol:vol) water:DMSO.

For evaluating control of boll weevil (*Anthonomus grandis*) the test unit consisted of 24-well-microtiter plates containing an insect diet and 20-30 *A. grandis* eggs. Different concentrations of formulated compounds were sprayed onto the insect diet at 20 µl, using a custom built micro atomizer, at two replications. After application, the microtiter plates were incubated at 23±1° C. and 50±5% relative humidity for 5 days. Egg and larval mortality was then visually assessed.

In this test, the compounds 19, 33, 62, 65, 66, 69, 81, 85, 86, 87, 88, 92, 93, 94, 95, 99, 101, 102, 104, 105, 106, 107, 108, 109, 110, 116, 138, 143, 145, 147, 148, 149, 150, 151, 153, 154, 155, 156, 157, 159, 160, 161, 162, 166, 167, 171, 185, 186, 188, 189, 190, 191, 192, 193, 194, 206, 207, 220, 221, 234 and 243, respectively at a concentration of the test solution of 2500 mg/L showed a mortality of 100%. In this test, the compounds 11, 13, 14, 16, 20, 22 and 30, respectively, at a concentration of the test solution of 2500 mg/L showed a mortality of at least 50%.

II.10 Activity Against Mediterranean Fruitfly (*Ceratitis capitata*)

The active compounds were formulated in 1:3 (vol:vol) DMSO:water.

For evaluating control of Mediterranean fruitfly the test unit consisted of microtiter plates containing an insect diet and 50 to 80 *C. capitata* eggs.

Different concentrations of formulated compounds were sprayed onto the insect diet at 5 µl, using a custom built micro atomizer, at two replications. After application, microtiter plates were incubated at 28±1° C. and 80±5% relative humidity for 5 days.

Egg and larval mortality was then visually assessed.

In this test the eggs which have been treated with 2500 ppm of compound 7, 21, 62, 63, 77, 79, 84, 92, 100, 101, 126, 128, 147, 166, 181, 183, 184, 231, 232, and 234, respectively showed a mortality of 50%.

The invention claimed is:

1. Pyrazole compounds of formulae I or II

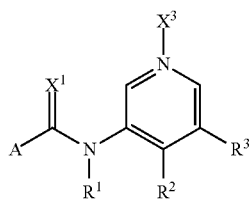

(I)

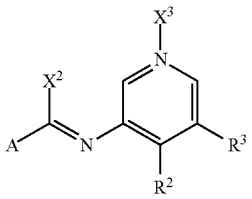

(II)

wherein

A is a pyrazole radical of the formulae A1, A2 or A3

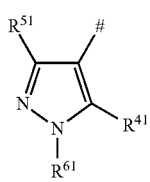

A1

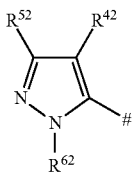

A2

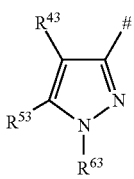

A3 denotes the binding site to the remainder of formulae I or II;

$X^1$ is S, O or $NR^{1a}$;

$X^2$ is $OR^{2a}$, $NR^{2b}R^{2c}$, $S(O)_m R^{2d}$;

$X^3$ is a lone pair or oxygen;

$R^1$ is hydrogen, CN, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_4$-alkylen-CN, $OR^a$, $C_1$-$C_4$-alkylen-$OR^a$, $C(Y)R^b$, $C_1$-$C_4$-alkylen-$C(Y)R^b$, $C(Y)OR^c$, $C_1$-$C_4$-alkylen-$C(Y)OR^c$, $S(O)_2R^d$, $NR^eR^f$, $C_1$-$C_4$-alkylen-$NR^eR^f$, $C(Y)NR^gR^h$, $C_1$-$C_4$-alkylen-$C(Y)NR^gR^h$, $S(O)_m NR^eR^f$, $C(Y)N$-$R^iNR^eR^f$, phenyl, hetaryl, phenyl-$C_1$-$C_4$-alkyl and hetaryl-$C_1$-$C_4$-alkyl wherein the aromatic ring of the four last mentioned radicals may be unsubstituted or may carry 1, 2, 3, 4 or 5 identical or different substituents $R^x$;

$R^2$ is hydrogen;

$R^3$ is hydrogen;

m is 0, 1 or 2;

$R^{41}$, $R^{42}$, $R^{43}$ are selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^{51}$ is selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$;

$R^{52}$, $R^{53}$ are selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, heterocyclyl, phenyl, phenyl-$C_1$-$C_4$-alkyl, phenoxy-$C_1$-$C_4$-alkyl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$;

$R^{61}$, $R^{63}$ are selected from the group consisting of hydrogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, heterocyclyl, phenyl, phenyl-$C_1$-$C_4$-alkyl, phenoxy-$C_1$-$C_4$-alkyl and heterocyclyl-$C_1$-$C_4$-alkyl wherein the heterocyclyl and aromatic ring of the 5 last mentioned radicals may be unsubstituted or may carry 1, 2, 3, 4 or 5 identical or different substituents $R^x$;

$R^{62}$ is selected from the group consisting of hydrogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $SR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$;

Y is O or S;

$R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2a}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2b}$, $R^{2c}$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2d}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ is selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl, $R^y$ are independently of each other selected from $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl and $C_1$-$C_{10}$-alkylcarbonyl;

or a salt or an N-oxide thereof, except for compounds of the formula I, wherein

A is of the formula A2, $X^1$ is O, $R^1$, $R^{42}$ and $R^{62}$ are each hydrogen, and $R^{53}$ is 2-hydroxyphenyl, 2-hydroxy-5-methylphenyl, 2-hydroxy-5-ethylphenyl, 2-hydroxy-5-chlorophenyl, 2-hydroxy-4,5-dimethylphenyl, 2-hydroxy-3,4-dimethylphenyl or 2-hydroxy-3,5-dimethylphenyl, A is of the formula A3, $X^1$ is O, $R^1$, $R^{43}$ and $R^{63}$ are each hydrogen, and $R^{53}$ is phenyl, 4-fluorophenyl, 4-methoxyphenyl, 3-bromophenyl, 4-bromophenyl, 4-chlorophenyl, 4-methylphenyl, 4-ethoxyphenyl, 2,4-dimethylphenyl, 2-hydroxyphenyl, 2-hydroxy-5-methylphenyl, 2-hydroxy-5-ethylphenyl, 2-hydroxy-5-chlorophenyl, 2-hydroxy-4,5-dimethylphenyl, 2-hydroxy-3,4-dimethylphenyl or 2-hydroxy-3,5-dimethylphenyl, $X^1$ is O, $R^1$ is hydrogen and A is 1-(phenylmethyl)-3-nitropyrazol-5-yl, 1-methylpyrazol-5-yl, 1-methyl-4-chloropyrazol-5-yl, 1-ethyl-4-bromopyrazol-3-yl, 1-ethyl-3-methylpyrazol-4-yl, 1-methyl-3-trifluormethylpyrazol-4-yl, 1-phenyl-5-benzoylaminopyrazol-4-yl, 1-(4-chlorophenyl)-3-phenylaminocarbonyl-5-methylpyrazol-4-yl, 1-phenyl-5-[(4-methylphenyl)carbonyl]aminopyrazol-4-yl, 4-iodopyrazol-3-yl, 1-methylpyrazol-3-yl, 5-chloro-1-methylpyrazol-3-yl, 5-nitropyrazol-3-yl, 1-(4-chlorophenyl)-5-trifluoromethylpyrazol-4-yl, 1-phenyl-3-thiophen-2-ylpyrazol-4-yl, 1-phenyl-3,5-dimethylpyrazol-4-yl, 4-bromo-5-nitropyrazol-3-yl, 5-cyclopropyl-1-(1,1-dioxotetrahydrothiophen-3-yl)-1H-pyrazol-3-yl;

and also except for the following compounds:
1-(4-chlorophenyl)-5-trifluoromethyl-1H-pyrazole-4-carboxylic acid pyridin-3-ylamide,
1-phenyl-3-thiophen-2-yl-1H-pyrazole-4-carboxylic acid pyridin-3-ylamide,
3,5-dimethyl-1-phenyl-1H-pyrazole-4-carboxylic acid pyridin-3-ylamide,
5-(4-chlorophenyl)-1-(2,4-dichlorophenyl)-4(2H-tetrazol-5-ylmethyl)-1H-pyrazole-3-carboxylic acid pyridin-3-ylamide, further except for the following compounds:
the compounds of the formula I, wherein A is of the formula A3, $X^1$ is O, $R^1$, and $R^{43}$ are each hydrogen, $R^{53}$ is 4-pyridyl and $R^{63}$ is 3-fluorophenyl or 3-chlorophenyl;

the compounds of the formula I, wherein A is of the formula A3, $X^1$ is O, $R^1$ is hydrogen, $C_1$-$C_6$-alkyl or $C_1$-$C_6$-haloalkyl, $R^{43}$ and $R^{53}$ are each hydrogen and $R^{63}$ is $C(Y)R^b$, $C(Y)OR^c$, $S(O)_2R^d$, $C(Y)NR^gR^h$ or $S(O)_mNR^eR^f$, wherein m is 2, Y is O or S, and wherein $R^c$, $R^d$, $R^e$, $R^f$, $R^g$ and $R^h$ are as previously defined;

the compound of the formula I, wherein A is of the formula A3, $X^1$ is O, $R^1$, $R^2$ and $R^3$ are each hydrogen, $R^{43}$ is methoxy, $R^{53}$ is 4-chlorophenyl and $R^{63}$ is 2-chlorophenyl; and the compounds of the formula I, wherein A is of the formula A2, $X^1$ is O, $R^1$ and $R^{42}$ are each hydrogen, $R^3$ is trifluoromethyl, $R^{52}$ is tert.-butyl and $R^{62}$ is benzyl.

2. The compound as claimed in claim 1 of the formula I.

3. The compound as claimed in claim 1 of the formula I, wherein $X^1$ is oxygen.

4. The compound as claimed in claim 1 of the formula I, wherein $R^1$ is hydrogen, $C_1$-$C_{10}$-alkyl, CN, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_4$-alkoxy-$C_1$-$C_{10}$-alkyl, $C_1$-$C_4$-alkylene-CN, $OR^a$, $C(Y)R^b$, $C(Y)OR^c$ or $S(O)_2R^d$.

5. The compound as claimed in claim 4, wherein $R^1$ is hydrogen, $C_1$-$C_3$-alkyl or $C_1$-$C_4$-alkylene-CN.

6. The compound as claimed in claim 1, wherein A is a radical A1.

7. The compound as claimed in claim 6, wherein $R^{41}$ and $R^{51}$ are independently selected from the group consisting of hydrogen, halogen, CN, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$.

8. The compound as claimed in claim 6, wherein $R^{41}$ and $R^{51}$ are selected, independently of each other, from the group consisting of hydrogen, halogen, CN, $C_1$-$C_4$-alkyl, $C_1$-$C_4$-haloalkyl, $C_3$-$C_6$-cycloalkyl and $C_3$-$C_6$-halocycloalkyl.

9. The compound as claimed in claim 8, wherein $R^{41}$ and $R^{51}$ are selected, independently of each other, from the group consisting of hydrogen, halogen, CN, $CH_3$, $CH_2F$, $CHF_2$ and $CF_3$.

10. The compound as claimed in claim 6, wherein either $R^{41}$ or $R^{51}$ is hydrogen or both $R^{41}$ and $R^{51}$ are hydrogen.

11. The compound as claimed in claim 6, wherein $R^{61}$ is selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-memberered hetarylmethyl wherein the (hetero)aromatic ring of the 5 last mentioned radicals may be unsubstituted or may carry 1, 2, 3, 4 or 5 identical or different substituents $R^x$ which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

12. The compound as claimed in claim 11, wherein $R^{61}$ is $C_1$-$C_4$-alkyl or $C_1$-$C_4$-haloalkyl.

13. The compound as claimed in claim 6, wherein the pyrazole compound is a compound of the formula I.

14. The compound as claimed in claim 13, wherein $X^1$ is oxygen.

15. The compound as claimed in claim 1, wherein A is a radical A2.

16. The compound as claimed in claim 15, wherein $R^{42}$ is selected from the group consisting of hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$ alkylsulfonyl, and $C_1$-$C_4$-haloalkylsulfonyl.

17. The compound as claimed in claim 16, wherein $R^{42}$ is selected from the group consisting of hydrogen, halogen, CN, $C_1$-$C_4$-alkyl, $C_1$-$C_4$-haloalkyl, $C_3$-$C_6$-cycloalkyl and $C_3$-$C_6$-halocycloalkyl.

18. The compound as claimed in claim 15, wherein $R^{52}$ is selected from the group consisting of hydrogen, halogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-memberered hetarylmethyl wherein the (hetero)aromatic ring of the 5 last mentioned radicals may be unsubstituted or may carry 1, 2, 3, 4 or 5 identical or different substituents which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

19. The compound as claimed in claim 15, wherein $R^{62}$ is selected from the group consisting of hydrogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, 5-membered hetaryl, benzyl and phenoxymethyl wherein the aromatic ring of the 4 last mentioned radicals may be unsubstituted or may carry 1, 2, 3, 4 or 5 identical or different substituents $R^x$ which is selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

20. The compound as claimed in claim 19, wherein $R^{62}$ is hydrogen, $C_1$-$C_4$-alkyl, $C_1$-$C_4$-haloalkyl, $C_3$-$C_6$-cycloalkyl or $C_3$-$C_6$-halocycloalkyl.

21. The compound as claimed in claim 15, wherein the pyrazole compound is a compound of the formula I.

22. The compound as claimed in claim 21, wherein $X^1$ is oxygen.

23. The compound as claimed in claim 1, wherein A is a radical A3.

24. The compound as claimed in claim 23, wherein $R^{43}$ is selected from the group consisting of hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

25. The compound as claimed in claim 24, wherein $R^{43}$ is selected from the group consisting of hydrogen, halogen, CN, $C_1$-$C_4$-alkyl, $C_1$-$C_4$-haloalkyl, $C_3$-$C_6$-cycloalkyl and $C_3$-$C_6$-halocycloalkyl.

26. The compound as claimed claim 23, wherein $R^{53}$ is selected from the group consisting of hydrogen, halogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-memberered hetarylmethyl wherein the (hetero)aromatic ring of the 5 last mentioned radicals may be unsubstituted or may carry 1, 2, 3, 4 or 5 identical or different substituents which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

27. The compound as claimed in claim 23, wherein $R^{63}$ is selected from the group consisting of hydrogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-memberered hetarylmethyl wherein the (hetero)aromatic ring of the 5 last mentioned radicals may be unsubstituted or may carry 1, 2, 3, 4 or 5 identical or different substituents $R^x$ which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl.

28. The compound as claimed in claim 27, wherein either $R^{53}$ or $R^{63}$ is hydrogen, CN, $C_1$-$C_4$-alkyl or $C_1$-$C_4$-haloalkyl, while the other radical $R^{53}$, $R^{63}$ is selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-memberered hetarylmethyl wherein the (hetero)aromatic ring of the 5 last mentioned radicals may be unsubstituted or may carry 1, 2, 3, 4 or 5 identical or different substituents $R^x$ which are selected from the group consisting of halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl, where $R^{53}$ may also be halogen.

29. The compound as claimed in claim 23, wherein the pyrazole compound is a compound of the formula I.

30. The compound as claimed in claim 29, wherein $X^1$ is oxygen.

31. An agricultural composition containing at least one compound of the formulae I or II as defined in claim 1 and/or an agriculturally acceptable salt or N-oxide thereof and at least one liquid or solid carrier.

32. Plant propagation material treated with at least one compound of formulae I or II as defined in claim 1 and/or an agriculturally acceptable salt or an N-oxide thereof.

* * * * *